(12) United States Patent
Baerson et al.

(10) Patent No.: US 10,000,762 B2
(45) Date of Patent: Jun. 19, 2018

(54) SORGHUM-DERIVED TRANSCRIPTION REGULATORY ELEMENTS PREDOMINANTLY ACTIVE IN ROOT HAIR CELLS AND USES THEREOF

(71) Applicant: The United States of America, as represented by the Secretary of Agriculture, Washington, DC (US)

(72) Inventors: Scott R. Baerson, Oxford, MS (US); Zhiqiang Pan, Oxford, MS (US); James J Polashock, Hainesport, NJ (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 156 days.

(21) Appl. No.: 14/717,477

(22) Filed: May 20, 2015

(65) Prior Publication Data
US 2016/0340685 A1 Nov. 24, 2016

(51) Int. Cl.
*C12N 15/82* (2006.01)
(52) U.S. Cl.
CPC .............................. *C12N 15/8227* (2013.01)
(58) Field of Classification Search
None
See application file for complete search history.

(56) References Cited

U.S. PATENT DOCUMENTS

| | | | |
|---|---|---|---|
| 7,132,528 B2 | 11/2006 | Heck et al. | |
| 2008/0196125 A1* | 8/2008 | Papes ................. | C12N 15/8223 800/298 |
| 2010/0011470 A1* | 1/2010 | Wan .................... | C12N 9/1205 800/287 |

OTHER PUBLICATIONS

Donald & Cashmore, EMBO J 9:1717-26 (1990).*
Kim et al., Plant Mol Biol 24:105-17 (1994).*
Dolferus et al., Plant Physiol 105:1075-87 (1994).*
Saha et al., In Silico Biol 7(1):7-19, 12 (2007).*
Baerson, Scott R.et al.,"Detoxification and Transcripome Response in *Arabidopsis* Seedlings Exposed to the Allelochemical Benzoxazdlin-2(3H)-one" (2005) Journal of Biological Chemistry 280: 21867-21581.
Baerson, Scott R. et al., "A Function Genomics Investigation of Allelochemical Biosynthesis in Sorghum bicolor Root Hairs" (2008) Journal of Biological Chemistry 283(6): 3231-3247.
Bertin, Cecile et al., "The Role of Root Exudates and Allelochemicals in the Rhizosphere" (2003) Plant and Soil 256: 67-83.
Bucher, Marcel et al., "Two Genes Encoding Extension-like Proteins are Predominantly Expressed in Tomato Root Hair Cells" (1997) Plant Molecular Biology 35: 497-508.
Cutter, Elizabeth G., "The Epidermis", (1978) Plant Anatomy, Chap 7, pp. 94-106, Clowes & Sons.
Czarnota, Mark A. et al., "Anatomy of Sorgoleone-Secreting Root Hairs of Sorghum Speices" (2003) Int. J. Plant Sci. 164(6): 861-866.
Czarnota, Mark A. et al., "Mode of Action, Localization of Production, Chemical Nature, and Activity of Sorgoleone: Sorgoleone: A Potent PSII Inhibitor in *Sorghum* spp. Root Exudates", (2001) Weed Technology 15(4): 813-825.
Duke, Stephen O., "Weeding With Transgenes", (2003) Trends in Biotechnology 21(5):192-195.
Grierson, Claire et al., "Root Hairs", The Arabidopsis Book, (2002) pp. 1-22; (2002) American Society of Plant Biologists.
Huang, Guozhong et al., "Engineering Broad Root-Knot Resistance in Transgenic Plants by RNAi Silencing of a Conserved and Essential Root-Knot Nematode Parsitism Gene", PNAS, (2006) 103 (39):14302-14306.
Kim, Dong W. et al., "Functional Conservation of a Root Hair Cell-Specific cis-Element in Angiosperms With Different Root Hair Distribution Patterns" (2006) Plant Cell, 18: 2958-2970.
Libault, Mark et al., "Root Hair Systems Biology" (2010) Trends in Plant Science 15(11): 641-650.
Parker, Jill S. et al., "Genetic Interactions During Root Hair Morphogenesis in *Arabodopsis*" (2000) The Plant Cell 12:1961-1974.
Pratt, Lee H. et al., "Sorghum Expressed Sequence Tags Identify Signature Genes for Drought, Pathogenesis, and Skotomorphogenesis From a Milestone Set of 16,801 Unique Transcripts" (2005) Plant Physiology, 139: 869-884
Wang, Guo-Dong et al., "Ex Planta Phytoremediation of Trichlorophenol and Phenolic Allelochemicals Via an Engineered Secretory Laccase" (2004) Nature Biotechnology 22(7): 893-897.
Weston, Leslie A. et al., "Sorghum Allelopathy—From Ecosystem to Molocule" (2013) J. Chem Ecol 39: 142-153.
Won, Su-Kyung et al., "cis-Element- and Transcriptome-Based Screening of Root Hair-Specific Genes and Their Functional Characterization in *Arabidopsis*" (2009) Plant Physiology 150: 1459-1473.
Zhiming, Yu et al., "Root Hair-Specific Expansins Modulate Root Hair Elongation in Rice" (2011) The Plant Journal 66:725-734.

* cited by examiner

*Primary Examiner* — Cathy Kingdon Worley
*Assistant Examiner* — Russell T Boggs
(74) *Attorney, Agent, or Firm* — David L. Marks; John D. Fado; Gail E. Poulos

(57) ABSTRACT

Transcription regulatory elements, namely promoter and terminator sequences, obtained from *Sorghum bicolor* that drive RNA transcription predominately in root hair cells are described, as well as cassettes, expression vectors, and genetically modified plants containing these transcription regulatory elements. The genetically modified plants can be gymnosperms, dicots, or monocots. Methods of directing transcription of a heterologous polynucleotide under control of these transcription regulatory elements in a genetically modified plant's root hair cells are also provided.

46 Claims, 8 Drawing Sheets

FIG. 6A   FIG. 6B   FIG. 6C   FIG. 6D
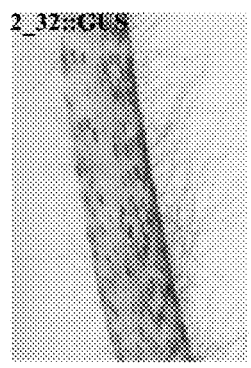 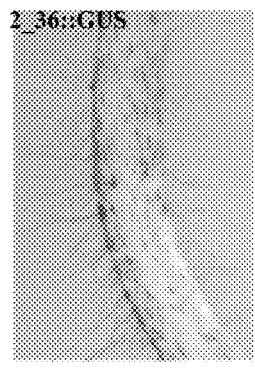 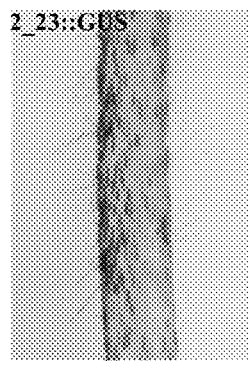 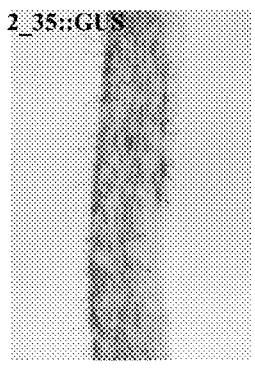
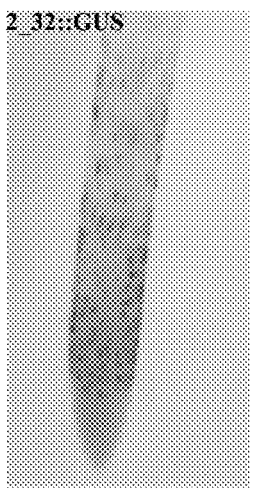 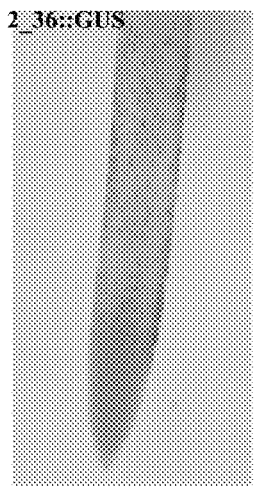 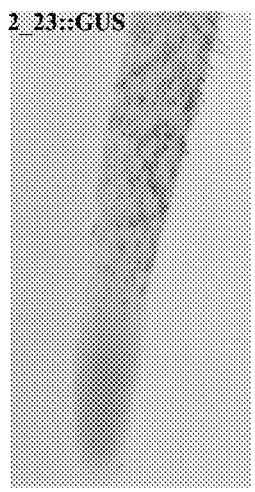 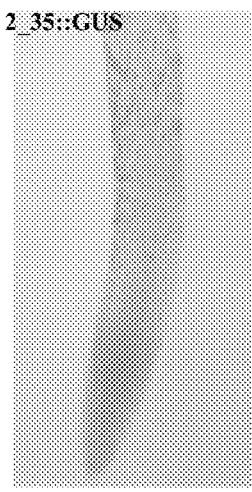
FIG. 6E   FIG. 6F   FIG. 6G   FIG. 6H

US 10,000,762 B2

SORGHUM-DERIVED TRANSCRIPTION REGULATORY ELEMENTS PREDOMINANTLY ACTIVE IN ROOT HAIR CELLS AND USES THEREOF

BACKGROUND OF THE INVENTION

Field of the Invention

This invention relates to expression vectors containing transcription regulatory elements are active in root hair cells in gymnosperms, dicots, and monocots. This invention also relates to genetically altered plants that contain an expression vector containing a heterologous polynucleotide operably linked at the 3' end and 5' end to these transcription regulatory elements.

Description of Related Art

Genetically altered plants are being used to solve various agricultural problems, environmental, pest infestation, low yield, etc. One method of generating genetically altered plants, one operably links a promoter with a polynucleotide encoding the gene of interest and introduces the heterologous DNA into a wild-type plant to generate the desired genetically altered plant. Of course one may need to screen the transformed plants to select the genetically altered plant, and the genetically altered plant's progeny, for the desired trait/gene product.

A variety of different types or classes of promoters can be used in genetically altered plants. Promoters can be classified on the basis of characteristics, such as temporal or developmental range, levels of transgene expression, or tissue specificity. For example, a constitutive promoter continuously expresses a gene with minimal regulation. Therefore, promoters referred to as constitutive promoters are capable of transcribing operably linked polynucleotides efficiently and expressing those polynucleotides in multiple tissues.

Numerous promoters, which are active in plant cells, have been described in the literature. Non-exhaustive examples include the nopaline synthase (nos) promoter and octopine synthase (ocs) promoter which are carried on tumor-inducing plasmids of *Agrobacterium tumefaciens* (also known as *Rhizobium radiobacter*), and the caulimovirus promoters such as the Cauliflower Mosaic Virus (CaMV) 19S or 35S promoter (U.S. Pat. No. 5,352,605), CaMV 35S promoter with a duplicated enhancer (CaMVE35S, U.S. Pat. Nos. 5,164,316; 5,196,525; 5,322,938; 5,359,142; and 5,424,200), and the Figwort Mosaic Virus (FMV) 35S promoter (U.S. Pat. No. 5,378,619). These promoters and numerous others have been used in the creation of constructs for transgene expression (expression of heterologous DNA) in plants. Other useful promoters for expression of heterologous DNA are described, for example, in U.S. Pat. Nos. 5,391,725; 5,428,147; 5,447,858; 5,608,144; 5,614,399; 5,633,441; 6,232,526; and 5,633,435.

While previous work has provided a number of promoters useful to direct transcription in genetically altered plants, there is still a great need for novel promoters with beneficial expression characteristics. In particular, there is a need for promoters that are capable of directing expression of heterologous genes or polynucleotides in the root hair cells of genetically altered plants.

Plant technologies which target the root-soil interface or surrounding rhizosphere via genetic engineering require transcription regulatory elements capable of directing accurate and high-level expression of heterologous polynucleotides within root hair cells. Moreover, the use of root hair-specific transcription elements could circumvent adverse effects, such as, but not limited to, potential reductions in crop yield resulting from non-cell type-specific expression of inhibitory gene products.

A plant's root hairs account for a majority of the total surface area of the plant's root systems, and represent the primary sites for nutrient (including mineral) and water uptake, interactions with soil microbes, as well as infection by nitrogen-fixing *rhizobia* leading to nodulation in legumes. See, e.g., Grierson and Schiefelbein, *Root Hairs* pp. 1-22 in *The Arabidopsis Book*, Somerville and Meyerowitz (eds.), American Society of Plant Biologists, Rockville, Md. (2002) (doi/10.1199/tab.0032; www.aspb.org/publications/*arabidopsis*); and Libault, et al., *Trends Plant Sci.* 15:641-650 (2010). Thus, numerous biotechnological applications exist for highly active root hair-specific gene promoters, and other polynucleotide sequences influencing steady-state transcript levels within these cells.

A number of studies have involved functional characterization of root hair promoters using promoter:reporter gene fusion constructs (cassettes or expression vectors). See, e.g., Kim, et al., *Plant Cell.* 18:2958-2970 (2006); Won, et al., *Plant Physiol.* 150:1459-1473 (2009); and Zhiming, et al., *Plant J.* February 11. doi:10.1111/j. (2011). However, these studies' goal was the elucidation of regulatory networks involved in root hair transcription, or the physiological role of the associated gene product, rather than identifying highly active promoters for driving heterologous DNA expression.

The root hairs of *Sorghum* spp. represent a particularly intriguing experimental system, which, to all appearances, serve as high-throughput production "facilities" for allelochemical biosynthesis and rhizosecretion, in addition to the above-mentioned functions (Weston, et al., *J. Chem. Ecol.* 39:142-153 (2013); Baerson, et al., *J. Biol. Chem.* 283:3231-3247 (2008)). A prior gene ontology analysis of genes expressed in *Sorghum bicolor* genotype BTx623 root hair cells revealed that a major proportion of transcriptional activity was associated with "metabolism" (approximately 11.2% of all functions assigned), consistent with previous ultrastructural studies suggesting a high level of metabolic activity for this cell type, likely associated with exudate production and membrane biogenesis (Parker, et al., *Plant Cell* 12:1961-1974 (2000); Czarnota, et al., *Weed Technol.* 15:813-825 (2001); Czarnota, et al., *Int. J. Plant Sci.* 164: 861-866 (2003); Baerson, et al. (2008)). Not surprisingly "cellular transport, transport mechanisms, and transport facilitation" was also identified as one of the major functional categories (approximately 7.9% of all functions assigned), given the pivotal role played by root hair cells in soil mineral and organic nutrient uptake (Cutter, *The Epidermis in Plant Anatomy* pp. 94-106, Clowes & Sons (London, England) (1978); Grierson and Schiefelbein (2002); Libault, et al. (2010)), and the additional specialization required of root hair cells of *Sorghum* spp. which synthesize and secrete large quantities of the allelochemical sorgoleone into the surrounding rhizosphere (Bertin, et al., *Plant Soil* 256:67-83 (2003); Weston, et al. (2013)).

As more genetically altered plants are developed in response to diseases and the need to increase yield for food products, a need exists for transcription regulatory elements capable of directing strong root hair-specific transgene expression. This invention is directed at promoters, used with or without specific 3' flanking regions (terminators), which direct high-level root hair-specific expression of heterologous DNA in both monocotyledonous plants and dicotyledonous plants and the methods of using the same. The regulatory elements described herein deliver recombinant gene products to root hairs at significantly higher levels than is possible using prior art promoters. See, e.g., Kim, et al. (2006); Won, et al. (2009); and Zhiming, et al. (2011).

BRIEF DESCRIPTION OF THE INVENTION

It is an object of this invention to provide transcription regulatory elements (promoters and terminators) that are predominantly active in plant root hair cells. It is a further object of this invention that these transcription regulatory elements, and in particular, the promoters, are selectively active or selectively direct transcription only in root hair cells of a plant. It is a further object of this invention to have DNA that contain one or more of the promoters and that the promoters have a polynucleotide sequence of SEQ ID NO: 1, 3, 5, 7, 12, 16, 20, and 24, or a sequence that is at least 95% identical to SEQ ID NO: 1, 3, 5, 7, 12, 16, 20, and 24. It is another object of this invention to have DNA that contain one or more of the terminators (or 3' flanking sequences) and that the terminators have a polynucleotide sequence of SEQ ID NO: 2, 4, 6, 8, 13, 17, 21, and 25, or a sequence that is at least 95% identical to SEQ ID NO: 2, 4, 6, 8, 13, 17, 21, and 25.

It is another object of this invention to have expression vectors and/or cassettes that contain one or more of the promoters described herein (SEQ ID NO: 1, 3, 5, 7, 12, 16, 20, and 24, or a sequence at least 95% identical to SEQ ID NO: 1, 3, 5, 7, 12, 16, 20, and 24) operably linked to a heterologous polynucleotide which encodes a gene of interest. Such an expression vector and/or cassette will predominantly express or selectively direct transcription of the gene of interest in a genetically altered plant's root hair cells. It is an optional object of this invention that the expression vector and/or cassette also contains one or more terminators described herein (SEQ ID NO: 2, 4, 6, 8, 13, 17, 21, and 25, or a sequence that is at least 95% identical to SEQ ID NO: 2, 4, 6, 8, 13, 17, 21, and 25) operably linked to the 3' end of the heterologous polynucleotide. It is an optional object of this invention that the expression vector and/or cassette contains a prior art terminator instead of the terminators described herein. It is a further object of this invention that the heterologous polynucleotide (or gene of interest) improves disease resistance, enhances nutrient uptake, improves resistance to colonization by soil-borne parasites, enhances colonization of beneficial rhizosphere-associated microorganisms, improves stress tolerance, enhances water uptake, promotes bioremediation, reduces competition from neighboring plants via allelochemical production, enhances nitrogen fixation (increased efficacy of nitrogen fixation), or imparts any other desired phenotypic traits to the root hair cells in a genetically altered plant containing the expression vector and/or cassette. Also, the expression of the gene of interest predominantly in the root hair cells can affect the entire genetically altered plant.

It is an object of this invention to have a genetically altered plant, parts of the genetically altered plant, and progeny of the genetically altered plant that contain an expression vector or a cassette that contains one or more of the promoters described herein (SEQ ID NO: 1, 3, 5, 7, 12, 16, 20, and 24, or a sequence at least 95% identical to SEQ ID NO: 1, 3, 5, 7, 12, 16, 20, and 24) operably linked to a heterologous polynucleotide which encodes a gene of interest. It is an optional object of this invention that the expression vector and/or cassette also contains one or more of terminators described herein (SEQ ID NO: 2, 4, 6, 8, 13, 17, 21, and 25, or a sequence that is at least 95% identical to SEQ ID NO: 2, 4, 6, 8, 13, 17, 21, and 25) operably linked to the 3' end of the heterologous polynucleotide. It is an optional object of this invention that the expression vector and/or cassette contains a prior art terminator instead of the terminators described herein. It is a further object of this invention that the heterologous polynucleotide (or gene of interest) improves disease resistance, enhances nutrient uptake, improves resistance to colonization by soil-borne parasites, enhances colonization of beneficial rhizosphere-associated microorganisms, improves stress tolerance, enhances water uptake, promotes bioremediation, reduces competition from neighboring plants via allelochemical production, enhances nitrogen fixation (increased efficacy of nitrogen fixation), or otherwise imparts any other desired phenotypic traits to the root hair cells in a genetically altered plant, parts thereof and progeny. It is another object of this invention that the plant can be a gymnosperm plant, monocot plant or a dicot plant. It is a further object of this invention that the part of the genetically altered plant can be a cell, tissue culture of the cells, pollen, seed, leaf, stem, etc.

It is an object of this invention to selectively direct transcription of a heterologous polynucleotide in the root hair cells of a genetically altered plant, or parts thereof, or its progeny, by (i) introducing an expression vector or a cassette into a wild-type plant, where the expression vector or cassette contains one or more of the promoters described herein (SEQ ID NO: 1, 3, 5, 7, 12, 16, 20, and 24, or a sequence at least 95% identical to SEQ ID NO: 1, 3, 5, 7, 12, 16, 20, and 24) operably linked to a heterologous polynucleotide which encodes a gene of interest, and (ii) selecting a genetically altered plant or part thereof that contains the expression vector or cassette, such that the heterologous polynucleotide is transcribed predominantly in the root hair cells of said genetically altered plant. It is an optional object of this invention that the expression vector or cassette contains one or more of the terminators described herein (SEQ ID NO: 2, 4, 6, 8, 13, 17, 21, and 25, or a sequence that is at least 95% identical to SEQ ID NO: 2, 4, 6, 8, 13, 17, 21, and 25) operably linked at the 3' end of the heterologous polynucleotide. It is an optional object of this invention that the expression vector and/or cassette contains a prior art terminator instead of the terminators described herein. It is a further object of this invention that the promoter selectively directs transcription of the heterologous polynucleotide in a plant's root hair cell. It is a further object of this invention that the first step of "introducing" is performed by introgression or transformation of a wild-type plant with the expression vector or cassette. It is another object of the invention that the genetically altered plant is a gymnosperm plant, dicot plant, or monocot plant. It is a further object of this invention that the heterologous polynucleotide (or gene of interest) improves disease resistance, enhances nutrient uptake, improves resistance to colonization by soil-borne parasites, enhances colonization of beneficial rhizosphere-associated microorganisms, improves stress tolerance, enhances water uptake, promotes bioremediation, reduces competition from neighboring plants via allelochemical production, enhances nitrogen fixation (increases efficacy of nitrogen fixation), or imparts any other desired phenotypic traits to the root hair cells in the genetically altered plant, parts thereof and progeny.

It is another object of this invention to have a method for producing a gene of interest predominantly in the root hair cells of a genetically altered plant by (i) introducing an expression vector or a cassette into a wild-type plant such that the expression vector or cassette contains at least one of the promoters described herein (SEQ ID NO: 1, 3, 5, 7, 12, 16, 20, and 24, or a sequence at least 95% identical to SEQ ID NO: 1, 3, 5, 7, 12, 16, 20, and 24) operably linked to a polynucleotide encoding the gene of interest, (ii) selecting a genetically altered plant or part thereof that contains the expression vector or cassette, and (iii) allowing the genetically altered plant or part thereof to grow root hair cells so that the gene of interest is produced in the root hair cells of the genetically altered plant because the promoter predominantly transcribes the polynucleotide encoding the gene of interest in a plant's root hair cell. It is an optional object of this invention that the expression vector or cassette contains one or more of the terminators described herein (SEQ ID NO: 2, 4, 6, 8, 13, 17, 21, and 25, or a sequence that is at least 95% identical to SEQ ID NO: 2, 4, 6, 8, 13, 17, 21, and 25) operably linked at the 3' end of the polynucleotide encoding the gene of interest. It is a further object of this invention that the first step of "introducing" is performed by introgression or transformation of a wild-type plant with the expression vector or cassette. It is another object of the invention that the genetically altered plant is a gymnosperm, dicot or monocot plant. It is an optional object of this invention that the expression vector or cassette contains one or more of the terminators described herein (SEQ ID NO: 2, 4, 6, 8, 13, 17, 21, and 25, or a sequence that is at least 95% identical to SEQ ID NO: 2, 4, 6, 8, 13, 17, 21, and 25) operably linked at the 3' end of the heterologous polynucleotide. It is an optional object of this invention that the expression vector and/or cassette contains a prior art terminator instead of the terminators described herein. It is a further object of this invention that the heterologous polynucleotide (or gene of interest) improves disease resistance, enhances nutrient uptake, improves resistance to colonization by soil-borne parasites, enhances colonization of beneficial rhizosphere-associated microorganisms, improves stress tolerance, enhances water uptake, promotes bioremediation, reduces competition from neighboring plants via allelochemical production, enhances nitrogen fixation (increases efficacy of nitrogen fixation), or imparts any other desired phenotypic traits to the root hair cells in the genetically altered plant, parts thereof and progeny.

BRIEF DESCRIPTION OF THE DRAWINGS

FIG. 6A through FIG. 6H show the expression patterns of GUSPlus in roots of genetically altered Oryza sativa (cv. Nipponbare) containing 2_32 promoter and 3' sequences (FIG. 6A and FIG. 6E), 2_36 promoter and 3' sequences (FIG. 6B and FIG. 6F), 2_23 promoter and 3' sequences (FIG. 6C and FIG. 6G), 2_35 promoter and 3' sequences (FIG. 6D and FIG. 6H). FIG. 6A through FIG. 6D are root segments of the 2-week-old genetically altered rice plants containing root hair-bearing trichoblasts; FIG. 6E though FIG. 6H are root apices of the 2-week-old genetically altered rice plants containing showing immature trichoblasts prior to root hair initiation.

FIG. 7A shows root hair-bearing trichoblasts, and FIG. 7B shows root apices containing immature trichoblasts prior to root hair initiation. FIG. 7C shows root hair-bearing trichoblasts, and FIG. 7D shows root apices containing immature trichoblasts prior to root hair initiation.

DETAILED DESCRIPTION OF THE INVENTION

Figures 1A, 1B, 1C, 1D:
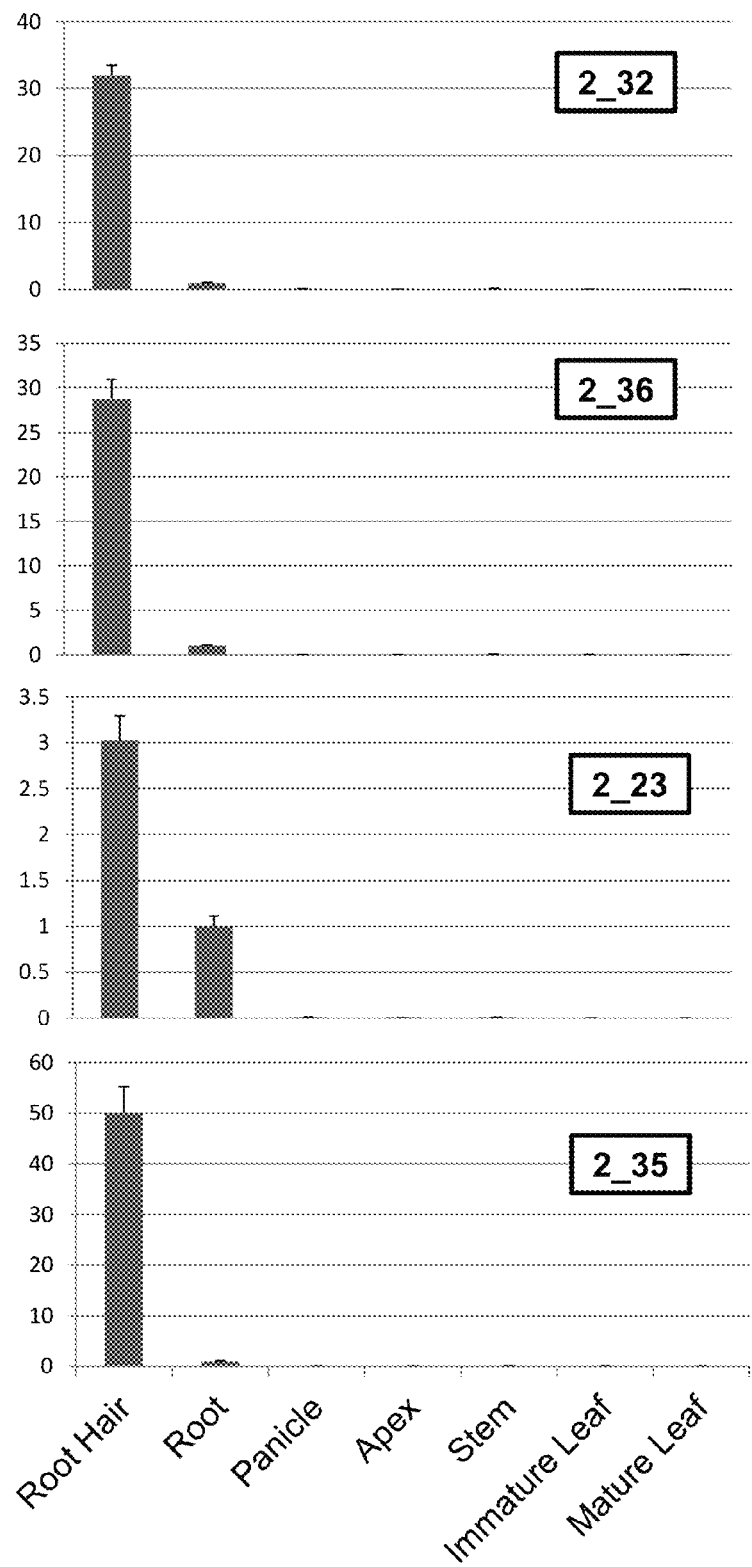
FIG. 1A through FIG. 1D shows the relative expression determined by quantitative real-time RT-PCR of the 2_32 candidate sequences (FIG. 1A), the 2_36 candidate sequences (FIG. 1B), the 2_23 candidate sequences (FIG. 1C), and the 2_35 candidate sequences (FIG. 1D) in S. bicolor root hair, root, panicle, apex, stem, immature leaf, and mature leaf.

One of the goals of generating genetically altered plants is to produce plants with agronomically desirable characteristics or traits. Advances in genetic engineering have provided the requisite tools to transform plants to contain and express genes of interest. The technological advances in plant transformation and regeneration have enabled researchers to take an exogenous polynucleotide, such as a gene from a heterologous or native source, and incorporate that polynucleotide into a plant genome. The gene can then be expressed in a plant cell to exhibit the added characteristic or trait. In one approach, expression of a gene in a plant cell or a plant tissue that does not normally express such a gene may confer a desirable phenotypic effect. In another approach, transcription of a gene or part of a gene in an antisense orientation may produce a desirable effect by preventing or inhibiting expression of an endogenous gene.

The regulatory elements described herein are useful for selectively directing the expression of a heterologous polynucleotide in root hair cells; in particular they cause a heterologous polynucleotide to be transcribed into RNA in root hair cells in gymnosperm, monocot, and dicot plants. The regulatory elements are predominately active in root hair cells. The promoters described herein can be used individually, or in combination with the terminator (or 3' flank region) sequences described herein or in combination with other terminator sequences. Further, this invention include promoters having a nucleotide sequence that is at least 95%, or at least 96%, or at least 97%, or at least 98%, or at least 99% identical to the promoter sequences described herein and which still are active predominantly in root hair cells. This invention also includes terminators having a nucleotide sequence that is at least 95%, or at least 96%, or at least 97%, or at least 98%, or at least 99% identical to the terminator sequences described herein.

The polynucleotide sequences of the promoters and terminators are as follows:
promoter sequence from 2_23 contig (Sb04g032670) is SEQ ID NO: 1;
3' sequence (terminator) from 2_23 contig (Sb04g032670) is SEQ ID NO: 2;
promoter sequence from 2_32 contig (Sb05g000390) is SEQ ID NO: 3;
3' sequence (terminator) from 2_32 contig (Sb05g000390) is SEQ ID NO: 4;
promoter sequence from 2_35 contig (Sb08g001960) is SEQ ID NO: 5;
3' sequence (terminator) from 2_35 contig (Sb08g001960) is SEQ ID NO: 6;
promoter sequence from 2_36 contig (Sb01g027620) is SEQ ID NO: 7;
3' sequence (terminator) from 2_36 contig (Sb01g027620) is SEQ ID NO: 8. In addition, the polynucleotide sequence of GUSPlus is SEQ ID NO: 9. See Table 2 for additional information about the contigs discussed herein.

The promoters and 3' flanking regions (terminator) sequences in the present invention are selected using the steady-state transcript levels of their corresponding genes as a primary criterion, it is hypothesized these transcription regulatory elements are capable of driving significantly higher heterologous gene expression levels in root hair cells than previously characterized transcription regulatory elements. The transcription regulatory elements of this invention have a wide range of biotechnological applications, because they are an important tool for manipulating or regulating heterologous polynucleotide expression within a cell type critical to plant growth and optimal crop yields. Root hair cells are the majority of a plant's interface with its surrounding soil environment. Thus, numerous applications for these transcription regulatory elements exist, such as, but not limited to, expression of heterologous DNA in genetically altered plant for which the gene product (also called "gene of interest") (i) promotes colonization of beneficial rhizosphere-associated microbes, (ii) is a transporter, channel, or other protein that facilitates more efficient water or nutrient uptake by the genetically altered plant compared to non-genetically altered plant, (iii) increases efficiency of nitrogen fixation in leguminous crops, (iv) is a protein useful in bioremediation (Wang, et al., *Nature Biotechnology*, 22:893-897 (2004)), (v) inhibits colonization by soil-borne pests such as parasitic nematodes (Huang, et al., *Proc. Natl. Acad. Sci. USA* 103(39):14302-14306 (2006)), (vi) inhibits competition from neighboring plants by facilitating allelochemical production (Duke, S. O., *Trends in Biotechnology* 21(5):192-195 (2003); Baerson, et al., *Journal of Biological Chemistry*, 283:3231-3247 (2008)).

One embodiment of this invention is a cassette containing one of the promoter sequences described herein (SEQ ID NO: 1, 3, 5, or 7); or containing a promoter sequence that are at least 95% identical to SEQ ID NO: 1, 3, 5, or 7; operably linked to a desired polynucleotide encoding a product of interest. Another embodiment of this invention is a cassette containing one of the promoter sequences described herein (SEQ ID NO: 1, 3, 5, 7); or containing a promoter sequence that are at least 95% identical to SEQ ID NO: 1, 3, 5, or 7; operably linked to a desired polynucleotide encoding a product of interest which, in turn, is operably linked to one of the terminator sequences described herein (SEQ ID NO: 2, 4, 6, or 8); or to a terminator sequence which is at least 95% identical to SEQ ID NO: 2, 4, 6, or 8; such that the promoter sequence is upstream of the desired polynucleotide and such that the terminator sequence is downstream of the desired polynucleotide. Another embodiment of this invention is one or more expression vectors or plasmids that contain such a cassette. Another embodiment of this invention is a genetically altered plant, parts thereof or progeny thereof, and/or a genetically altered plant cell that contains one or more of these cassettes or contains one or more expression vectors containing one or more of these cassettes. The genetically altered plant, parts thereof, or progeny; or genetically altered plant cell will preferentially transcribe the desired polynucleotide and produce the desired product in the genetically altered plant's root hair cells.

The promoter sequence(s) and the terminator sequence(s) of this invention are also referred to as transcription regulatory element(s). Further, a "3'" and "3' flanking" sequence are also referred to as a "terminator" sequence. A "desired polynucleotide" is "heterologous" polynucleotide to the genetically altered plant (parts thereof, and/or cell); that is, the polynucleotide is not normally present in the non-genetically altered plant (wild-type plant), or, the polynucleotide is present in higher amount in the genetically altered plant (parts thereof, and/or cell) compared to the non-genetically altered plant (wild-type plant), or, the polynucleotide is transcribed in the genetically altered plant's root hair cells in a higher amount compared to the amount transcribed in the non-genetically altered plant (wild-type plant). Thus, the "desired polynucleotide" is also referred to as "heterologous polynucleotide" or "heterologous DNA" or "heterologous gene" or "heterologous gene polynucleotide" or "transcribable polynucleotide". In one embodiment of this invention, the polynucleotide sequences that are operably linked to these transcription regulatory elements in wild-type, non-genetically altered plants and/or plant cells (and which are discussed in Table 2 below) are not considered "heterologous polynucleotides".

In one embodiment, this invention involves using the transcription regulatory elements (promoter only or a promoter and terminator) described herein and/or cassettes containing these transcription regulatory elements in expression vectors to drive transcription of a heterologous polynucleotide in a genetically altered plant's root hair cells. In another embodiment, this invention also involves making genetically altered plants, parts thereof, and/or cell that contain an expression vector or cassette containing one or more of the transcription regulatory elements described herein operably linked to a heterologous polynucleotide and which will preferentially produce the encoded gene product in the genetically altered plant's root hair cells. A further embodiment of this invention involves genetically altered dicot plants containing a cassette which contains one of the promoters described herein operably linked to a heterologous polynucleotide and which is, in turn, operably linked to one of the terminators described herein or to a different terminator. Another embodiment of this invention involves genetically altered monocot plants containing a cassette which contains one of the promoters described herein operably linked to a heterologous polynucleotide and which is, in turn, operably linked to one of the terminators described herein or to a different terminator. Another embodiment of this invention involves genetically altered gymnosperm plants containing a cassette which contains one of the promoters described herein operably linked to a heterologous polynucleotide and which is, in turn, operably linked to one of the terminators described herein or to a different terminator. The cassette containing the promoter and heterologous polynucleotide and terminator can be located in a genetically altered plant cell's nucleus.

The polynucleotide sequences of the cassettes described in the examples below are as follows: 2_23 promoten:GUSPlus::2_23-3' cassette is SEQ ID NO: 10; 2_32 promoten:GUSPlus::2_32-3' cassette is SEQ ID NO: 14; 2_35 promoten:GUSPlus::2_35-3' cassette is SEQ ID NO: 18; and 2_36 promoten:GUSPlus::2_36-3' cassette is SEQ ID NO: 22. However, one of ordinary skill in the art understands that one can substitute a polynucleotide sequence encoding a desired protein, RNAi, rRNA, or other product for GUSPlus' polynucleotide sequence in these cassettes (i.e., a heterologous polynucleotide). In fact, it is highly likely that one of ordinary skill in the art would want to exchange GUSPlus' polynucleotide sequence for a heterologous polynucleotide sequence, and one of ordinary skill in the art would have the knowledge of how to construct such a cassette using information contained in the examples below or information that is well-known to one of ordinary skill in the art field.

Furthermore, one of ordinary skill in the art has the knowledge to construct a cassette containing a heterologous polynucleotide which is operably linked to a promoter sequence from one contig described herein (SEQ ID NO: 1, 3, 5, or 7), or a sequence that is at least 95% identical to SEQ ID NO: 1, 3, 5, or 7, and also operably linked to a terminator sequence from a different contig described herein (SEQ ID NO: 2, 4, 6, or 8), or a sequence that is at least 95% identical to SEQ ID NO: 2, 4, 6, or 8, or with a different terminator. Thus, as an example, one could pair the promoter sequence from contig 2_23 with the terminator sequence from contig 2_32, contig 2_35, or contig 2_36 with the desired heterologous polynucleotide sequence. Again, one of ordinary skill in the art would have the knowledge of how to construct such a cassette.

Finally, one of ordinary skill in the art has the knowledge to insert a cassette containing a promoter sequence described herein operably linked to a heterologous polynucleotide sequence operably linked to a terminator sequence described herein into a different expression vector than the plasmid described in Example 1 and then transformed the desired plant or plant cell with the new expression vector and generate a genetically altered plant containing the expression vector containing the desired cassette.

Because this invention involves production of genetically altered plants and involves recombinant DNA techniques, the following definitions are provided to assist in describing this invention. The terms "isolated", "purified", or "biologically pure" as used herein, refer to material that is substantially or essentially free from components that normally accompany the material in its native state or when the material is produced. In an exemplary embodiment, purity and homogeneity are determined using analytical chemistry techniques such as polyacrylamide gel electrophoresis or high performance liquid chromatography. A nucleic acid or particular bacteria that are the predominant species present in a preparation is substantially purified. In an exemplary embodiment, the term "purified" denotes that a nucleic acid or protein that gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, and peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides and polynucleotides that are not commercially available can be chemically synthesized e.g., according to the solid phase phosphoramidite triester method first described by Beaucage and Caruthers, *Tetrahedron Letts.* 22:1859-1862 (1981), or using an automated synthesizer, as described in Van Devanter et al., *Nucleic Acids Res.* 12:6159-6168 (1984). Other methods for synthesizing oligonucleotides and polynucleotides are known in the art. Purification of oligonucleotides is by either native acrylamide gel electrophoresis or by anion-exchange HPLC as described in Pearson & Reanier, *J. Chrom.* 255:137-149 (1983).

The terms "identical" or percent "identity", in the context of two or more nucleic acids or polypeptide sequences, refer to two or more sequences or subsequences that are the same or have a specified percentage of amino acid residues or nucleotides that are the same (e.g., 80%, 85% identity, 90% identity, 99%, or 100% identity), when compared and aligned for maximum correspondence over a designated region as measured using a sequence comparison algorithm or by manual alignment and visual inspection.

The phrase "high percent identical" or "high percent identity", in the context of two polynucleotides or polypeptides, refers to two or more sequences or subsequences that have at least about 80%, identity, at least about 81%, 82%, 83%, 84%, 85%, 86%, 87%, 88%, 89%, 90%, 91%, 92%, 93%, 94%, 95%, 96%, 97%, 98%, 99%, or 100% nucleotide or amino acid residue identity, when compared and aligned for maximum correspondence, as measured using a sequence comparison algorithm or by visual inspection. In an exemplary embodiment, a high percent identity exists over a region of the sequences that is at least about 50 residues in length. In another exemplary embodiment, a high percent identity exists over a region of the sequences that is at least about 100 residues in length. In still another exemplary embodiment, a high percent identity exists over a region of the sequences that is at least about 150 residues or more in length. In one exemplary embodiment, the sequences are high percent identical over the entire length of the nucleic acid or protein sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al. (eds.), *Current Protocols in Molecular Biology*, 1995 supplement).

The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant cells may express genes/polynucleotides that are not found within the native (non-recombinant or wild-type) form of the cell or express native genes in an otherwise abnormal amount—over-expressed, under-expressed or not expressed at all—compared to the non-recombinant or wild-type cell or organism. In particular, one can alter the genomic DNA of a wild-type plant by molecular biology techniques that are well-known to one of ordinary skill in the art and generate a recombinant plant.

The terms "transgenic", "transformed", "transformation", and "transfection" are similar in meaning to "recombinant". "Transformation", "transgenic", and "transfection" refer to the transfer of a polynucleotide into a host organism or into a cell. Such a transfer of polynucleotides can result in genetically stable inheritance of the polynucleotides or in the polynucleotides remaining extra-chromosomally (not integrated into the chromosome of the cell). Genetically stable inheritance may potentially require the transgenic organism or cell to be subjected for a period of time to one or more conditions which require the transcription of some or all of the transferred polynucleotide in order for the transgenic organism or cell to live and/or grow. Polynucleotides that are transformed into a cell but are not integrated into the host's chromosome remain as an expression vector within the cell. One may need to grow the cell under certain growth or environmental conditions in order for the expression vector to remain in the cell or the cell's progeny. Further, for expression to occur the organism or cell may need to be kept under certain conditions. Genetically altered organisms or cells containing the recombinant polynucleotide can be referred to as "transgenic" or "transformed" organisms or cells or simply as "transformants", as well as recombinant organisms or cells.

A genetically altered organism is any organism with any changes to its genetic material, whether in the nucleus or cytoplasm (organelle). As such, a genetically altered organism can be a recombinant or transformed organism. A genetically altered organism can also be an organism that was subjected to one or more mutagens or the progeny of an organism that was subjected to one or more mutagens and has mutations in its DNA caused by the one or more mutagens, as compared to the wild-type organism (i.e, organism not subjected to the mutagens). Also, an organism that has been bred to incorporate a mutation into its genetic material is a genetically altered organism. For the purposes of this invention, the organism is a plant.

As used herein, the term "promoter" refers to a polynucleotide that in its native state is located upstream or 5' to a translational start codon of an open reading frame (or protein-coding region) and that is involved in recognition and binding of RNA polymerase and other proteins (trans-acting transcription factors) to initiate transcription. A "plant promoter" is a native or non-native promoter that is functional in plant cells. The promoters described herein are predominately functional in root hair cells and thus are considered "tissue-specific promoters". A plant promoter can be used as a 5' regulatory element for modulating expression of a particular desired polynucleotide (heterologous polynucleotide) operably linked thereto. When operably linked to a transcribeable polynucleotide, a promoter typically causes the transcribable polynucleotide to be transcribed in a manner that is similar to that of which the promoter is normally associated. In one embodiment, a promoter having the sequence of SEQ ID NO: 1, 3, 5, or 7, or a sequence which is at least 95% identical thereto, is operably linked to a transcribable polynucleotide (a gene or polynucleotide of interest). This polynucleotide of interest, when transcribed, provides a desirable characteristic associated with plant morphology, physiology, growth and development, yield, nutritional enhancement, disease or pest resistance, or environmental or chemical tolerance.

Plant promoters can include promoters produced through the manipulation of known promoters to produce artificial, chimeric, or hybrid promoters. Such promoters can also combine cis-elements from one or more promoters, for example, by adding a heterologous regulatory element to an active promoter with its own partial or complete regulatory elements. Thus, the design, construction, and use of chimeric or hybrid promoters containing at least one cis-element of SEQ ID NO: 1, 3, 5, or 7 for modulating the expression of operably linked polynucleotide sequences is encompassed by the present invention. The term "cis-element" refers to a cis-acting transcriptional regulatory element that confers an aspect of the overall control of gene expression. A cis-element may function to bind transcription factors, trans-acting protein factors that regulate transcription. Some cis-elements bind more than one transcription factor, and transcription factors may interact with different affinities with more than one cis-element. The promoters of the present invention desirably contain cis-elements that can confer or modulate gene expression.

The term "vector" refers to DNA, RNA, a protein, or polypeptide that was be introduced into a host cell or organism. The polynucleotides, protein, and polypeptide which are to be introduced into a host can be therapeutic or prophylactic in nature; can encode or be an antigen; can be regulatory in nature; etc. There are various types of vectors including virus, plasmid, bacteriophages, cosmids, and bacteria.

An expression vector is nucleic acid capable of replicating in a selected host cell or organism. An expression vector can replicate as an autonomous structure, or alternatively can integrate, in whole or in part, into the host cell chromosomes or the nucleic acids of an organelle, or it is used as a shuttle for delivering foreign DNA to cells, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an "expression cassette". In contrast, as described in the examples herein, a "cassette" is a polynucleotide containing a section of an expression vector. The use of the cassettes assists in the assembly of the expression vectors. An expression vector is a replicon, such as plasmid, phage, virus, chimeric virus, or cosmid, and which contains the desired polynucleotide sequence operably linked to the expression control sequence(s).

A heterologous polynucleotide sequence is operably linked to one or more transcription regulatory elements (e.g., promoter, terminator and, optionally, enhancer) such that the transcription regulatory elements control and regulate the transcription and/or translation of that heterologous polynucleotide sequence. A cassette can have the heterologous polynucleotide operably linked to one or more transcription regulatory elements. As used herein, the term "operably linked" refers to a first polynucleotide, such as a promoter, connected with a second transcribable polynucleotide, such as a gene of interest, where the polynucleotides are arranged such that the first polynucleotide affects the transcription of the second polynucleotide. In some embodiments, the two polynucleotide molecules are part of a single contiguous polynucleotide. In other embodiments, the two polynucleotides are adjacent. For example, a promoter is operably linked to a gene of interest if the promoter regulates or mediates transcription of the gene of interest in a cell. Similarly a terminator is operably linked to the polynucleotide of interest if the terminator regulates or mediates transcription of the polynucleotide of interest, and in particular, the termination of transcription. Constructs of the present invention would typically contain a promoter operably linked to a transcribable polynucleotide operably linked to a terminator.

Thus, constructs (cassette or expression vector) of the present invention contain one or more of the promoters described herein (having the sequence of SEQ ID NOs: 1, 3, 5, and/or 7, or a sequence that is at least 95% identical thereto), operably linked to a transcribable polynucleotide and, optionally, operably linked to one or more of the terminators described herein (have the sequence of SEQ ID NOs: 2, 4, 6, and/or 8, or a sequence that is at least 95% identical thereto) or to a heterologous terminator, so as to direct transcription of the transcribable polynucleotide in a root hair cell upon introduction of the construct into a plant cell. In some cases, the transcribable polynucleotide encodes a protein-coding region of a gene, and the promoter provides for transcription of a functional mRNA molecule that is translated and expressed as a protein product. Constructs may also transcribe antisense RNA or other similar inhibitory RNA in order to inhibit expression of a specific RNA molecule of interest in a root hair cell.

Exemplary heterologous polynucleotide for incorporation into constructs of the present invention include, for example, desired polynucleotides from a species other than the target plant's species, or even desired polynucleotides that originate with or are present in the same plant species, but are incorporated into the genetically altered plant cells by genetic engineering methods rather than classical reproduction or breeding techniques or by a combination of genetic engineering methods followed by breeding techniques. Heterologous polynucleotides refer to any polynucleotide molecule that is introduced into a recipient cell and is transcribed at levels that differ from the wild-type cell. A heterologous polynucleotide can include a polynucleotide that is already present in the plant cell, polynucleotide from another plant, polynucleotide from a different organism, or a polynucleotide generated externally, such as a polynucleotide containing an antisense message of a gene, or a polynucleotide encoding an artificial or modified version of a gene.

In one embodiment, the heterologous polynucleotide which is operably linked to a promoter and, optionally, to a terminator described herein encodes a gene of interest. As used herein, "gene of interest" refers to any heterologous polynucleotide that, upon transcription and, optionally, translation, imparts a desirable characteristic associated with plant morphology, physiology, growth and development, yield, nutritional enhancement, disease or pest resistance, or environmental or chemical tolerance. The expression of a gene of interest is desirable in order to confer an important trait to the genetically altered plant cell, plant, parts thereof and/or progeny. A gene of interest that provides a beneficial agronomic trait to crop plants includes, but is not limited to, polynucleotides that encode herbicide resistance (U.S. Pat. Nos. 5,633,435 and 5,463,175), increased yield (U.S. Pat. No. 5,716,837), insect control (U.S. Pat. Nos. 6,063,597; 6,063,756; 6,093,695; 5,942,664; and 6,110,464), fungal disease resistance (U.S. Pat. Nos. 5,516,671; 5,773,696; 6,121,436; 6,316,407, and 6,506,962), virus resistance (U.S. Pat. Nos. 5,304,730 and 6,013,864), nematode resistance (U.S. Pat. No. 6,228,992), bacterial disease resistance (U.S. Pat. No. 5,516,671), starch production (U.S. Pat. Nos. 5,750, 876 and 6,476,295), modified oils production (U.S. Pat. No. 6,444,876), high oil production (U.S. Pat. Nos. 5,608,149 and 6,476,295), modified fatty acid content (U.S. Pat. No. 6,537,750), high protein production (U.S. Pat. No. 6,380,466), fruit ripening (U.S. Pat. No. 5,512,466), enhanced animal and human nutrition (U.S. Pat. Nos. 5,985,605 and 6,171,640), biopolymers (U.S. Pat. Nos. 5,958,745 and 6,946,588), environmental stress resistance (U.S. Pat. No. 6,072,103), pharmaceutical peptides (U.S. Pat. No. 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), and biofuel production (U.S. Pat. No. 5,998,700). For the purposes of this invention, plant "nutrients" include minerals and organic compounds that plants need. It is understood that the expression of the gene of interest predominately in the root hair cells of a genetically altered plant can affect the entire genetically altered plant. For example, the predominant expression in root hair cells of certain protein(s) may enhance the genetically altered plant's resistance to environmental stress; the impact is not limited to simply the root hair cells.

Alternatively, a heterologous polynucleotide can affect the plant's phenotype by encoding a non-translated RNA that causes targeted inhibition of expression of an endogenous gene, for example, by antisense and inhibitory RNA, or RNA interference-mediated mechanisms. The non-translated RNA could also be a catalytic RNA molecule (i.e., a ribozyme) engineered to cleave a desired endogenous mRNA product. For the purposes of this invention, the gene of interest includes within its definition a non-translated RNA because such a non-translated RNA affects the characteristics of the genetically altered plant cell, plant, parts thereof, and/or progeny containing the construct described herein. Thus, any heterologous polynucleotide that encodes a protein or mRNA that expresses a phenotype or morphology change of interest is useful for the practice of the present invention.

Transformation and generation of genetically altered monocotyledonous and dicotyledonous plant cells is well known in the art. See, e.g., Weising, et al., *Ann. Rev. Genet.* 22:421-477 (1988); U.S. Pat. No. 5,679,558; *Agrobacterium Protocols*, ed: Gartland, Humana Press Inc. (1995); and Wang, et al. *Acta Hort.* 461:401-408 (1998). The choice of method varies with the type of plant to be transformed, the particular application and/or the desired result. The appropriate transformation technique is readily chosen by the skilled practitioner.

Exemplary transformation/transfection methods available to those skilled in the art include, but are not limited to: direct uptake of foreign DNA constructs (see, e.g., EP 295959); techniques of electroporation (see, e.g., Fromm et al., *Nature* 319:791 (1986)); and high-velocity ballistic bombardment with metal particles coated with the nucleic acid constructs (see, e.g., Kline, et al., *Nature* 327:70 (1987) and U.S. Pat. No. 4,945,050). Specific methods to transform heterologous genes into commercially important crops (to make genetically altered plants) are published for rapeseed (De Block, et al., *Plant Physiol.* 91:694-701 (1989)); sunflower (Everett, et al., *Bio/Technology* 5:1201 (1987)); soybean (McCabe, et al., *Bio/Technology* 6:923 (1988), Hinchee, et al., *Bio/Technology* 6:915 (1988), Chee, et al., *Plant Physiol.* 91:1212-1218 (1989), and Christou, et al., *Proc. Natl. Acad. Sci USA* 86:7500-7504 (1989)); rice (Hiei, et al., *Plant J.* 6:271-282 (1994)), and corn (Gordon-Kamm, et al., *Plant Cell* 2:603-618 (1990), and Fromm, et al., *Biotechnology* 8:833-839 (1990)). Other known methods are disclosed in U.S. Pat. Nos. 5,597,945; 5,589,615; 5,750,871; 5,268,526; 5,262,316; and 5,569,831.

One exemplary method includes employing *Agrobacterium tumefaciens* (*Rhizobium radiobacter*) or *Agrobacterium rhizogenes* as the transforming agent to transfer heterologous DNA into the plant. *Agrobacterium tumefaciens*-meditated transformation techniques are well described in the scientific literature. See, e.g., Horsch, et al. *Science* 233:496-498 (1984), and Fraley, et al. *Proc. Natl. Acad. Sci. USA* 80:4803 (1983). Typically, a plant cell, an explant, a meristem or a seed is infected with *Agrobacterium tumefaciens* transformed with the expression vector/construct which contains the heterologous nucleic acid operably linked to a promoter. Under appropriate conditions known in the art, the transformed plant cells are grown to form shoots, roots, and develop further into genetically altered plants. In some embodiments, the heterologous nucleic acid can be introduced into plant cells, by means of the Ti plasmid of *Agrobacterium tumefaciens*. The Ti plasmid is transmitted to plant cells upon infection by *Agrobacterium tumefaciens*, and is stably integrated into the plant genome. See, e.g., Horsch, et al. (1984), and Fraley, et al. (1983).

Transformed plant cells which are derived by any of the above transformation techniques can be cultured to regenerate a whole plant which possesses the desired transformed phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture*, in *Handbook of Plant Cell Culture*, pp. 124-176, MacMillan Publishing Company, New York, 1983; and Binding, *Regeneration of Plants*, in *Plant Protoplasts*, pp. 21-73, CRC Press, Boca Raton, 1985. Regeneration can also be obtained from plant callus, explants, organs, or parts thereof. Such regeneration techniques are described generally in Klee, et al., *Ann. Rev. of Plant Phys.* 38:467-486 (1987).

Once a genetically altered plant has been generated, one can breed it with a wild-type plant and screen for heterozygous F1 generation plants containing the genetic change present in the parent genetically altered plant. Then F2 generation plants can be generated which are homozygous for the genetic alteration. These heterozygous F1 generation plants and homozygous F2 plants, progeny of the original genetically altered plant, are considered genetically altered plants, having the altered genomic material from the genetically altered parent plant.

Marker-assisted selection is a method of selecting desirable individuals in a breeding scheme based on DNA molecular marker patterns instead of, or in addition to, their phenotypic traits. Marker-assisted selection provides a useful tool that allows for efficient selection of desirable crop traits and is well known in the art (see, e.g., Podlich, et al., *Crop Sci.* 44:1560-1571 (2004); Ribaut and Hoisington, *Trends in Plant Science* 3:236-238 (1998); Knapp, S., *Crop Science* 38:1164-1174 (1998); Hospital, F., *Marker-assisted breeding*, pp 30-59, in *Plant molecular breeding*, H. J. Newbury (ed.), Blackwell Publishing and CRC Press (Oxford and Boca Raton).

After one obtains a genetically altered plant containing a heterologous polynucleotide operably linked to a promoter described herein and a terminator described herein, one can efficiently breed the genetically altered plant with other plants containing desired traits. One can use molecular markers (i.e., polynucleotide probes) based on the sequence of the promoter described herein, terminator described herein, heterologous polynucleotide, and/or another sequence in the expression vector to determine which offspring of crosses between the genetically altered plant and the other plant possess the expression vector containing the desired cassette. This process is known as Marker Assisted Rapid Trait Introgression (MARTI). Briefly, MARTI involves (1) crossing the genetically altered plant (containing the expression vector containing the cassette described herein) with a plant line having desired phenotype/genotype ("elite parent") for introgression to obtain F1 offspring. The F1 generation is heterozygous for cassette. (2) Next, an F1 plant is be backcrossed to the elite parent, producing BC1F1 which genetically produces 50% wild-type and 50% heterozygote for the cassette. (3) PCR using the polynucleotide probe is performed to select the heterozygote genetically altered plants containing the cassette. (4) Selected heterozygotes are then backcrossed to the elite parent to perform further introgression. (5) This process of MARTI is performed for several more cycles. (6) Next, the heterozygote genetically altered plant is self-pollinated to produce BC6F2 generation. The BC6F2 generation produces a phenotypic segregation ratio of 3 wild-type parent plants to 1 genetically altered plant. (7) One selects the genetically altered plants at the BC6F2 generation at the seedling stage using PCR with the polynucleotide probe and can optionally be combined with phenotypic selection at maturity. These cycles of crossing and selection can be achieved in a span of 2 to 2.5 years (depending on the plant), as compared to many more years for conventional backcrossing introgression method now in use. Thus, the application of MARTI using PCR with a polynucleotide probe significantly reduces the time to introgress the desired genetic alteration into elite lines for producing commercial hybrids. The final product is an inbred plant line almost identical (99%) to the original elite in-bred parent plant that is the homozygous for the heterologous polynucleotide encoding the desired product.

Many techniques involving molecular biology discussed herein are well-known to one of ordinary skill in the art and are described in, e.g., Green and Sambrook, *Molecular Cloning, A Laboratory Manual* 4th ed. 2012, Cold Spring Harbor Laboratory; Ausubel et al. (eds.), *Current Protocols in Molecular Biology*, 1994—current, John Wiley & Sons; and Kriegler, *Gene Transfer and Expression: A Laboratory Manual* (1993). Unless otherwise noted, technical terms are used according to conventional usage. Definitions of common terms in molecular biology maybe found in e.g., Benjamin Lewin, *Genes IX*, Oxford University Press, 2007 (ISBN 0763740632); Krebs, et al. (eds.), *The Encyclopedia of Molecular Biology*, Blackwell Science Ltd., 1994 (ISBN 0-632-02182-9); and Robert A. Meyers (ed.), *Molecular Biology and Biotechnology: a Comprehensive Desk Reference*, VCH Publishers, Inc., 1995 (ISBN 1-56081-569-8).

The term "plant" includes whole plants, plant organs, progeny of whole plants or plant organs, embryos, somatic embryos, embryo-like structures, protocorms, protocorm-like bodies (PLBs), and suspensions of plant cells. Plant organs comprise, e.g., shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like).

The class of plants that can be used in the method of the invention is generally as broad as the class of higher and lower plants amenable to the molecular biology and plant breeding techniques described herein, specifically gymnosperms and angiosperms (monocotyledonous (monocots) and dicotyledonous (dicots) plants). It includes plants of a variety of ploidy levels, including aneuploid, polyploid, diploid, haploid and hemizygous. The genetically altered plants described herein can be monocot plant, and more particularly, monocot crops, such as, but not limited to, *sorghum*, maize, wheat, rice, barley, oats, rye, millet, and triticale. The genetically altered plants described herein can also be dicot plants, and more particularly, dicot crops, such as apple, pear, peach, plum, orange, lemon, lime, grapefruit, pomegranate, olive, peanut, cotton, tobacco, cucumber, carrot, potato, celery, tomato, legume (beans), raspberry, blackberry, blackberry, strawberry, blueberry, etc. Also, the genetically altered plants (or plants with altered genomic DNA) can be horticultural plants such as rose, marigold, primrose, dogwood, pansy, geranium, etc. Other plants include, but are not limited to, grasses, oak, walnut, pecan, poplar, etc. The genetically altered plants described herein can also be gymnosperms, such as but not limited to cycads, conifers (redwoods, sequoias, pines, fir and hemlock), and ginkgo.

The terms "approximately" and "about" refer to a quantity, level, value or amount that varies by as much as 30%, or in another embodiment by as much as 20%, and in a third embodiment by as much as 10% to a reference quantity, level, value or amount. As used herein, the singular form "a", "an", and "the" include plural references unless the context clearly dictates otherwise. For example, the term "a bacterium" includes both a single bacterium and a plurality of bacteria.

Having now generally described this invention, the same will be better understood by reference to certain specific examples and the accompanying drawings, which are included herein only to further illustrate the invention and are not intended to limit the scope of the invention as defined by the claims. The examples and drawings describe at least one, but not all embodiments, of the inventions claimed. Indeed, these inventions may be embodied in many different forms and should not be construed as limited to the embodiments set forth herein; rather, these embodiments are provided so that this disclosure will satisfy applicable legal requirements.

Example 1. High-Throughput Sequence Analysis of *S. bicolor* Transcripts

Seeds of *S. bicolor* genotype BTx623 are purchased from Crosbyton Seed Company (Crosbyton, Tex.). Seeds are germinated and grown for eight days in the dark under soil-free conditions using a capillary mat system devised by Czarnota, et al. (2001). Root hairs are isolated from dark-grown 8-day-old seedling root systems using the method devised by Bucher, et al., *Plant Mol. Biol.* 35:497-508 (1997), involving immersion in liquid nitrogen with gentle stirring, followed by filtration through a 250 µM aluminum mesh to remove root system debris. Purity of the root hair preparations is assessed by bright-field microscopy, and only highly enriched preparations are retained for subsequent RNA extraction and sequence analysis. Root hair preparations are stored at −80° C. prior to RNA extraction. Total RNAs are isolated from root hairs using TRIzol® Reagent (Invitrogen Corp., Carlsbad, Calif.) per manufacturer's recommended protocol, with an additional homogenization step of 30 seconds at 25,000 rpm using a hand-held homogenizer. RNAs are then re-purified using RNeasy Plant Mini-Kit (Qiagen, Inc., Germantown, Md.), including an "on column" DNase I treatment using a RNase-Free DNase kit (Qiagen, Inc., Germantown, Md.) according to manufacturer's recommended protocol, to remove residual DNA contamination. RNA purity is determined spectrophotometrically, and integrity is assessed by agarose gel electrophoresis.

For Sanger EST analysis, polyA+ mRNA is prepared from root hair total RNA using an Oligotex mRNA Midi Kit (Qiagen, Inc., Germantown, Md.), and used for construction of a directional cDNA library with the Uni-Zap XR cDNA library construction kit (Stratagene, Santa Clara, Calif.), per manufacturer's recommended protocol. 5' DNA sequencing reactions are performed using ABI BigDye Terminator Cycle Sequence Ready Reaction kits (Applied Biosystems, Foster City, Calif.) as previously described (Pratt, et al., *Plant Physiol.* 139:869-884 (2005)). High throughput sequence data are also generated using total RNAs prepared as described above for Sanger EST analysis, and strand-specific libraries are constructed for 3 biological replicate root hair samples using the procedure described by Zhong and coworkers (High-Throughput Illumina Strand-Specific RNA Sequencing Library Preparation. Cold Spring Harb. Protoc. doi:10.1101/pdb.prot5652 (2011)). Library aliquots are analyzed using an Illumina HiSeq 2500 System (Illumina Inc., San Diego, Calif.) as single-end reads for 150 cycles and are mapped to the *S. bicolor* genotype BTx623 genome v1.4 (www.phytozome.org). The EST analysis indicated that over 10,000 different mRNAs are present in the *sorghum* root hair cells.

In an expressed sequence tag study, the number of sequence tags corresponding to a particular sequence is directly proportional to how highly expressed that sequence is. Thus, to identify highly expressed root hair-specific gene candidates for follow-up promoter:reporter studies, all expressed sequences identified are first ranked by sequence count. The top 100 of these sequences (out of the more than 10,000 sequences expressed in the *sorghum* root hair cells) are then used for BLASTN analyses against all other publicly-available *S. bicolor* EST libraries. From these efforts, eight sequences are identified as exhibiting a highly root hair-preferential expression.

Out of these eight sequences, steady-state transcript accumulation levels for four of the sequences (see Table 2, infra) are assessed to confirm that these sequences are expressed primarily in *S. bicolor* root hair cells using quantitative real-time RT-PCR using the protocol previously described Baerson, et al. (*J. Biol. Chem.* 280:21867-21881 (2005)). The steady-state levels of the endogenous transcripts corresponding to contigs 2_36, 2_35, 2_32, and 2_23 (loci nos. Sb01g027620, Sb08g001960, Sb05g000390, Sb04g032670, respectively; see Table 2) are determined in various *S. bicolor* tissues via qRT-PCR using gene-specific primers (see FIG. 1A though FIG. 1D). Immature leaves and shoot apices from *S. bicolor* genotype BTx623 are isolated from seedlings maintained in a growth chamber at 28° C. for 8 days in standard (approximately 20×40 cm) nursery flats using Premier Pro Mix PGX potting media (Hummert International, Earth City, Mo.) under a combination of cool-white fluorescent and incandescent lighting at an intensity of approximately 400 µmol $m^{-2}$ $s^{-1}$ and a 16-hour photoperiod. Developing panicles, mature leaves, and culm (stem) tissues are isolated from 10-week-old greenhouse-grown plants. At the time of harvest, panicles are partially exerted from flag leaf sheaths, just prior to anthesis. All harvested *S. bicolor* tissues are directly flash-frozen in liquid nitrogen and stored at −80° C. prior to analysis.

Total RNAs are isolated from 0.5 g aliquots of flash-frozen *S. bicolor* genotype BTx623 tissues using the above described protocol. Quantitative real-time PCR reactions are performed in triplicate using the GenAmp® 7300 Sequence Detection System (Life Technologies, Carlsbad, Calif.) as previously described in Baerson, et al. (2005). First strand cDNAs are synthesized from 2 µg of total RNA in a 100 µL reaction volume using the TaqMan Reverse Transcription Reagents Kit (Life Technologies, Carlsbad, Calif.) per manufacturer's recommended protocol. Independent PCR reactions are performed using the same cDNA for both the gene of interest (loci nos. Sb01g027620, Sb08g001960, Sb05g000390, or Sb04g032670), and 18S rRNA as an internal control, using the SYBR® Green PCR Master Mix (Life Technologies, Carlsbad, Calif.). Gene-specific primer pairs are designed for all sequences using Primer Express v.3.0.1 software (Life Technologies, Carlsbad, Calif.). See Table 1 for primer information and Table 2 for more information about the genes.

TABLE 1

| Gene & Primer | Sequence |
|---|---|
| Sb01g027620; forward primer | 5'-TTGCCGATTCAGTGCTCCTGTTCGT-3' (SEQ ID NO: 26) |
| Sb01g027620; reverse primer | 5'-CGTGCAACAACATCGCACCAAGGA-3' (SEQ ID NO: 27) |
| Sb08g001960; forward primer | 5'-ATCCAGGGCTACAAGAAGGG-3' (SEQ ID NO: 28) |
| Sb08g001960; reverse primer | 5'-CGACAGGTGATGATGGCGAA-3' (SEQ ID NO: 29) |
| Sb05g000390; forward primer | 5'-ATACTACCGGGAGCCACACAAG-3' (SEQ ID NO: 30) |
| Sb05g000390; reverse primer | 5'-CCAAGGAGGTGAAGTGGCAG-3' (SEQ ID NO: 31) |
| Sb04g032670; forward primer | 5'-AATGATGCGTTGTTATTTGATTGCTT-3' (SEQ ID NO: 32) |

TABLE 1-continued

| Gene & Primer | Sequence |
|---|---|
| Sb04g032670; reverse primer | 5'-TGGTGACTGCTGTACTATGTGG-3' (SEQ ID NO: 33) |
| 18S rRNA; forward primer | 5'-GGCTCGAAGACGATCAGATACC-3' (SEQ ID NO: 34) |
| 18S rRNA; reverse primer | 5'-TCGGCATCGTTTATGGTT-3' (SEQ ID NO: 35) |

A dissociation curve is generated at the end of each PCR cycle to verify that a single product is amplified using software provided with the GeneAmp® 7300 sequence detection system. A negative control reaction in the absence of template (no template control) is also routinely performed in triplicate for each primer pair. The change in fluorescence of SYBR® Green I dye in every cycle is monitored by the GenAmp® 7300 system software, and the threshold cycle ($C_T$) above background for each reaction is calculated. The $C_T$ value of 18S rRNA is subtracted from that of the gene of interest to obtain a $\Delta C_T$ value. The $C_T$ value of an arbitrary calibrator (e.g., the tissue sample from which the largest $\Delta C_T$ values are obtained) is subtracted from the $\Delta C_T$ value to obtain a $\Delta \Delta C_T$ value. The fold-changes in expression level relative to the calibrator are calculated as $2^{-\Delta \Delta C_T}$. The value provides the relative expression levels for each sequence, and is expressed as mean±S.D. from assays performed in triplicate.

The steady-state levels of the endogenous transcripts corresponding to contigs 2_36 (FIG. 1A), 2_35 (FIG. 1B), 2_32 (FIG. 1C), and 2_23 (FIG. 1D) (loci nos. Sb01g027620, Sb08g001960, Sb05g000390, Sb04g032670, respectively, in Table 2), the highest steady-state transcript levels occurred in root hairs. For each contig gene, some transcriptional expression is also detected in whole seedling roots which is expected given the presence of root hairs cells in those samples. Thus, the results of the qRT-PCR analyses (FIG. 1A though FIG. 1D) are consistent with the root hair-preferential expression patterns for contigs 2_36, 2_35, 2_32, and 2_23 inferred from the initial transcriptome studies.

Information regarding these four contigs is located in Table 2, infra. Interestingly, the sequence for contig ID no. 2_32, which is found to be the most highly expressed root-hair specific sequence (FIG. 1A), corresponds to fatty acid desaturase (SbDES3) which generates the unusual 16:3$\Delta^{9,12,15}$ fatty acid required for biosynthesis of the allelochemical sorgoleone (Pan, et al., *J. Biol. Chem.* 282:4326-4335 (2007)).

Example 2. Cassette and Expression Vector Construction

Figure 2:
FIG. 2 shows a binary expression vector (p7N-2_32-GUS) constructed for evaluation of the 2_32 promoten:GUSPlus::2_32-3' cassette, where "2_32 Pro" is promoter, "GUSPlus" is 0-glucuronidase, "bar" is neomycin phosphotransferase plant-selectable marker, "2_32 Ter" is 3' flanking region, "NOS pro" is nopaline synthase promoter, "T35S" is CaMV 35S terminator, "pVS1 ORI" and "ColE1" are replication origins, "Sm/Sp" is streptomycin/spectinomycin bacterial-selectable marker, "LB" is left border, and "RB" is right border.
Figure 5:
FIG. 5 shows a binary expression vector (p7N-2_35-GUS) constructed for evaluation of the 2_35 promoten:GUSPlus::2_35-3' cassette, where "2_35 Pro" is promoter, "GUSPlus" is 0-glucuronidase, "bar" is neomycin phosphotransferase plant-selectable marker, "2_35 Ter" is 3' flanking region, "NOS pro" is nopaline synthase promoter, "T35S" is CaMV 35S terminator, "pVS1 ORI" and "ColE1" are replication origins, "Sm/Sp" is streptomycin/spectinomycin bacterial-selectable marker, "LB" is left border, and "RB" is right border.

The sequences corresponding to contig ID numbers 2_36, 2_35, 2_32, and 2_23 (Table 2) are chosen for further evaluation in promoter::reporter gene::terminator experiments using the models *Arabidopsis* and rice. Approximately 2.5 kb of 5' flanking sequence (promoter), and 1.5 kb of 3' flanking sequence (terminator) (both relative to the predicted start and stop codons, respectively) are identified by alignment with the *S. bicolor* genotype BTx623 genomic sequence (www.phytozome.org), and used for the construction of binary vectors containing promoter::reporter gene::3' sequence cassettes using β-glucuronidase (GUSPlus, also referred to herein as "GUS") as the reporter gene (Jefferson, et al., *EMBO J.* 6:3901-3907 (1987)). The promoter::GUSPlus::3'-flanking region (terminator) cassettes are assembled by overlap-extension PCR or fusion PCR (see, Shevchuk, et al., *Nucleic Acids Res.* 32:e19 (2004)) to avoid inclusion of extraneous sequences. This method can be used to operably link any gene of interest to any of the promoters and terminator sequences described herein. The enhanced 'GUSPlus' coding sequence used for all promoter::reporter gene:: terminator cassettes is amplified from pCAMBIA1305.1 (CAMBIA, Canberra, Australia), and the assembled cassettes are cloned into the binary vector p7P-Nos (DNA Cloning Service, Hamburg, Germany). p7P-Nos contains the bar gene as the plant selectable marker driven by the relatively weak *A. tumefaciens* nopaline synthase (NOS) promoter, which reduces the possibility of cross-activation of adjacent root hair-specific promoters within the same T-DNA (see FIG. 2 though FIG. 5).

The promoter and 3' flanking sequence (terminator) regions of selected putative root hair-specific genes (contig ID numbers 2_36, 2_35, 2_32, and 2_23) are initially obtained via PCR amplification using *S. bicolor* genotype BTx623 genomic DNA as template. The forward and reverse PCR primer sequences used for amplification of all promoter and terminator regions from genomic DNA are shown in

TABLE 2

| Contig ID | Locus ID | %, Total Sanger ESTs | FPKM, RH-a | FPKM, RH-b | FPKM, RH-c | FPKM, mean | Putative Function | E-value | Source |
|---|---|---|---|---|---|---|---|---|---|
| 2_32 | Sb05g000390 | 0.4572 | 1.68E+04 | 1.33E+04 | 1.60E+04 | 1.54E+04 | Fatty acid desaturase DES3 | 0.0 | ABN49521 (*S. bicolor*) |
| 2_35 | Sb08g001960 | 0.4572 | 3.74E+03 | 2.23E+03 | 3.74E+03 | 3.23E+03 | γ-tocopherol methyltransferase | 4E−123 | ABE41797 (*Z. mays*) |
| 2_36 | Sb01g027620 | 0.4389 | 1.03E+04 | 1.17E+04 | 1.25E+04 | 1.15E+04 | Glutathione S-transferase | 9E−71 | AAM94545 (*O. sativa*) |
| 2_23 | Sb04g032670 | 0.3658 | 2.57E+03 | 2.67E+03 | 2.07E+03 | 2.44E+03 | Root-specific protein RCc3 | 1E−36 | BAD25630 (*O. sativa*) |

Table 3. All PCR reactions are performed using PfuUltra High-Fidelity DNA Polymerase (Stratagene, Santa Clara, Calif.) per manufacturer's recommended protocol. The PCR products obtained are gel purified using a QIAquick Gel Extraction Kit (Qiagen Inc., Valencia, Calif.) according to the manufacturer's recommended protocol, then used as templates for a second round of PCR amplifications leading to the assembly of GUSPlus expression cassettes (described below).

Clara, Calif.), followed by gel purification of the resulting PCR products using a QIAquick Gel Extraction Kit, per manufacturer's instructions. The forward and reverse PCR primer sequences used for generation of these second round promoter, terminator, and GUSPlus-containing fragment are shown in Table 4 below.

Fusion PCR (see, e.g., Shevchuk, et al. (2004)) is next performed using the gel-purified promoter-, GUSPlus-, and terminator-containing fragments generated in the second

TABLE 3

Primers used for initial amplification of fragments from *S. bicolor* BTx623 genomic DNA

| Primer | Description | Primer sequence (5' -> 3') |
|---|---|---|
| 2_32_pF | 2_32 promoter 5' (forward) | GCCGGAGCCACCCGTCATGGAGC (SEQ ID NO: 36) |
| 2_32_pR | 2_32 promoter 3 (reverse) | GGCTGGCGGTTGTGGTGGTGAACAAGC (SEQ ID NO: 37) |
| 2_32_tF | 2_32 terminator 5' (forward) | TGACTTGCATCATTGCTGGGAGG (SEQ ID NO: 38) |
| 2_32_tR | 2_32 terminator 3' (reverse) | AAGAGGACGACGTCGGCGGCGT (SEQ ID NO: 39) |
| 2_35_pF | 2_35 promoter 5' (forward) | CCTCTACCTTTCATCAAGCTTCC (SEQ ID NO: 40) |
| 2_35_pR | 2_35 promoter 3' (reverse) | GCCCGATGAAGTATATGTAGACG (SEQ ID NO: 41) |
| 2_35_tF | 2_35 terminator 5' (forward) | TAGCAGAGGAACTTACTGTCACAACG (SEQ ID NO: 42) |
| 2_35_tR | 2_35 terminator 3' (reverse) | AAGTTGCAACTCATCTCCAACT (SEQ ID NO: 43) |
| 2_36_pF | 2_36 promoter 5' (forward) | ACAGTCTGATCTGACCTTCCTGA (SEQ ID NO: 44) |
| 2_36_pR | 2_36 promoter 3' (reverse) | CATTTCCTCCTCCCTAGCTTCTA (SEQ ID NO: 45) |
| 2_36_tF | 2_36 terminator 5' (forward) | TGAACCAACATACTCGATCGGTTCCT (SEQ ID NO: 46) |
| 2_36_tR | 2_36 terminator 3' (reverse) | CCATGCAACCTTAGCACCACGTCA (SEQ ID NO: 47) |
| 2_23_pF | 2_23 promoter 5' (forward) | GTATGGCGAATGCAAACCAC (SEQ ID NO: 48) |
| 2_23_pR | 2_23 promoter 3' (reverse) | TATTGCTCGATCACACCAGCTC (SEQ ID NO: 49) |
| 2_23_tF | 2_23 terminator 5' (forward) | GATCTCAGCCTCATCCTCAACTAC (SEQ ID NO: 50) |
| 2_23_tR | 2_23 terminator 3' (reverse) | CTGGCTGATATTGGGCTATGTG (SEQ ID NO: 51) |

In the second round of PCR, the various terminator/promoter-containing PCR fragments obtained from genomic DNA templates (described above) are re-amplified (used as templates) in PCR reactions using primers which add flanking restriction enzyme sites to the 5' ends of promoter fragments and 3' ends of terminator fragments, facilitating ligation of the final transgene cassettes with appropriately-digested transformation vector DNA. In addition, a fragment containing the GUSPlus coding sequence is generated via PCR using plasmid pCAMBIA1305.1 as template. All of these second round PCR reactions are performed using PfuUltra High-Fidelity DNA Polymerase (Stratagene, Santa PCR round (described above) as so-called "megaprimers" (Shevchuk, et al. (2004)), to obtain the final promoter::GUSPlus::terminator cassettes containing flanking restriction enzyme sites. The use of this approach enables the attachment of the promoters and terminators to the GUSPlus coding sequences without the addition of extraneous sequences, thus preserving the original sequence context present within the endogenous *S. bicolor* genes. The previously made second round PCR-generated promoter, GUSPlus, and terminator fragments are combined in equimolar quantities such that the total DNA amounts are 400 ng. The PCR reaction mixtures (25 μl final volume) consist of the three fragments, 1× reaction buffer, 0.2 mM dNTPs and 1 unit of PfuUltra High-fidelity DNA Polymerase (Stratagene, Santa Clara, Calif.). The thermal profile used for these reactions consist of 15 seconds at 95° C., 15 seconds at 65° C., followed by 5 minutes at 72° C. for 15 cycles. Next, 5 µl of each (unpurified) PCR reaction are then used as template in a final round of PCR, and these (50 µl final volume) PCR reactions contain 1× reaction buffer, 0.2 mM dNTPs, 2 units of PfuUltra High-fidelity DNA Polymerase, and 5 pM each of forward and reverse primer appropriate for the cassette being generated (see Table 4). The thermal profile used for these final round PCR reactions consists of 15 seconds at 95° C., 15 seconds at 65° C., followed by 8 minutes at 72° C. for 25 cycles. The forward and reverse primers used in this final PCR amplification step are complementary to the 5' and 3' promoter::GUSPlus::terminator cassettes, and are identical to the primer sequences used for the second round PCR reactions (described above) but, here, restriction enzyme sites have already been introduced into the 5' ends of promoter sequences, and 3' ends of the terminator sequences. For example, the forward and reverse primers used in this final PCR step for assembly of the 2_36 promoter::GUSPlus::2_36 terminator cassette are 2_36_pFA and 2_36_tRB, respectively, and the primers for assembly of the 2_32 promoten:GUSPlus::2_26 terminator cassette are 2_32_pFH and 2_32_tRE, respectively (Table 4). The nucleotide sequences of the final assembled cassettes are confirmed by DNA sequence analysis.

The DNA sequence for 2_23 promoten:GUSPlus::2_23-3' cassette is SEQ ID NO: 10. The sequence for the SfiI-2_23 promoter::GUS-plus::2_23 terminator—SfiI cassette is in SEQ ID NO: 11. The DNA sequence for SfiI—2_23 promoter is in SEQ ID NO: 12. The DNA sequence for 2_23 terminator—SfiI is in SEQ ID NO: 13.

The DNA sequence for 2_32 promoten:GUSPlus::2_32-3' cassette is SEQ ID NO: 14. The sequence for the HindIII—2_32 promoten:GUSPlus::2_32 terminator—EcoRI cassette is in SEQ ID NO: 15. The sequence for the HindIII—2_32 promoter is SEQ ID NO: 16. The sequence for 2_32 terminator—EcoRI is SEQ ID NO: 17.

The DNA sequence for 2_35 promoten:GUSPlus::2_35-3' cassette is SEQ ID NO: 18. The sequence for the SfiI—2_35 promoter::GUS-plus::2_35 terminator—SfiI cassette is in SEQ ID NO: 19. The DNA sequence for SfiI—2_35 promoter is SEQ ID NO: 20. The DNA sequence for 2_35 terminator—SfiI is SEQ ID NO: 21.

The DNA sequence for 2_36 promoten:GUSPlus::2_36-3' cassette is SEQ ID NO: 22. The sequence for the SfiI-2_36 promoter::GUS-plus::2_36 terminator—SfiI cassette is in SEQ ID NO: 23. The sequence of SfiI-2_36 promoter is in SEQ ID NO: 24. The sequence of 2_36 terminator—SfiI is in SEQ ID NO: 25.

TABLE 4

Primers used for generation of Fusion PCR templates and amplification of final assembled transgene cassettes

| Primer Description | Primer sequence (5' -> 3') |
| --- | --- |
| 2_32_pFH HindIII-2_32 promoter 5' (forward) | cgcaagcTTAGCTAGATCGGATGGTTAAGA (SEQ ID NO: 52) |
| 2_32_pgR 2_32 promoter 3' (reverse) | TTACCCTCAGATCTACCATGGCTGGCGGTTGTGGTGGTG (SEQ ID NO: 53) |
| 2_32_pgF GUSPlus-5' fusion w/2_32 (forward) | CACCACCACAACCGCCAGCC<u>ATG</u>GTAGATCTGAGGGTAA (SEQ ID NO: 54) |
| 2_32_gtR GUSPlus-3' fusion w/2_32 (reverse) | CCTCCCAGCAATGATGCAAGTCACACGTGATGGTGATGG (SEQ ID NO: 55) |
| 2_32_gtF 2_32 terminator 5' (forward) | CCATCACCATCACGTG<u>TGA</u>CTTGCATCATTGCTGGGAGG (SEQ ID NO: 56) |
| 2_32_tRE 2_32 terminator-EcoRI 3' (reverse) | ccgaattcTCGAGATTTTATTCTCGCAGGTAGAGGCAG (SEQ ID NO: 57) |
| 2_35_pFA SfiI-2_35 promoter 5' (forward) | gcggcccttaaGGCCTCTGGGTACTGCTATTGAG (SEQ ID NO: 58) |
| 2_35_pgR 2_35 promoter 3' (reverse) | GAAATTTACCCTCAGATCTACCATCGACGACGACGCACGACGTAC (SEQ ID NO: 59) |
| 2_35_pgF GUSPlus-5' fusion w/2_35 (forward) | GTACGTCGTGCGTCGTCGTCG<u>ATG</u>GTAGATCTGAGGGTAAATTTC (SEQ ID NO: 60) |
| 2_35_gtR GUSPlus-3' fusion w/2_35 (reverse) | CGTTGTGACAGTAAGTTCCTCTGCTATCACACGTGATGGTGATGG (SEQ ID NO: 61) |
| 2_35_gtF 2_35 terminator 5' (forward) | CCATCACCATCACGTG<u>TGATAG</u>CAGAGGAACTTACTGTCACAACG (SEQ ID NO: 62) |
| 2_35_tRB 2_35 terminator-SfiI 3' (reverse) | gcggccatggcGGCCAAGTTGCAACTCATCTCCAACTC (SEQ ID NO: 63) |
| 2_36_pFA SifI-2_36 promoter 5' (forward) | gcggcccttaaggccCAATATGCATCGGCATCTTG (SEQ ID NO: 64) |
| 2_36_pgR 2_36 promoter 3' (reverse) | TTTACCCTCAGATCTACCATTTCCTCCTCCCTAGCTTCTATTCTT (SEQ ID NO: 65) |

TABLE 4-continued

Primers used for generation of Fusion PCR templates and amplification of final assembled transgene cassettes

| Primer Description | Primer sequence (5' -> 3') |
|---|---|
| 2_36_pgF GUSPlus-5' fusion w/2_36 (forward) | AAGAATAGAAGCTAGGGAGGAGGAAATGGTAGATCTGAGGGTAAA (SEQ ID NO: 66) |
| 2_36_gtR GUSPlus-3' fusion w/w_36 (reverse) | AGGAACCGATCGAGTATGTTGGTTCACACGTGATGGTGATGGTGA (SEQ ID NO: 67) |
| 2_36_gtF 2_36 terminator 5' (forward) | TCACCATCACCATCACGTGTGAACCAACATACTCGATCGGTTCCT (SEQ ID NO: 68) |
| 2_36_tRB 2_36 terminator-SfiI 3' (reverse) | gcggccatggcggccATGCAACCTTAGCACCACGTCA (SEQ ID NO: 69) |
| 2_23_pFA SfiI-2_23 promoter 5' (forward) | gcggcccttaaggccACACTAGAATCACTCTCCCACTC (SEQ ID NO: 70) |
| 2_23_pgR 2_23 promoter 3' (reverse) | AAATTTACCCTCAGATCTACCATTATTGCTCGATCACACCAGCTC (SEQ ID NO: 71) |
| 2_23_pgF GUSPlus-5' fusion w/2_23 (forward) | GAGCTGGTGTGATCGAGCAATAATGGTAGATCTGAGGGTAAATTT (SEQ ID NO: 72) |
| 2_23_gtR GUSPlus-3' fusion w/2_23 (reverse) | GCGCTGAGATCCAGGCGCTCATCACACGTGATGGTGATGGTGATG (SEQ ID NO: 73) |
| 2_23_gtF 2_23 terminator 5' (forward) | CATCACCATCACCATCACGTGTGATGAGCGCCTGGATCTCAGCGC (SEQ ID NO: 74) |
| 2_23_tRB SfiI-2_23 terminator 3' (reverse) | gcggccatggcggccGGGGTGCGAATACCATAGAAAC (SEQ ID NO: 75) |

*start and stop codons are underlined; and added nucleotides introducing flanking restriction enzymes sites are shown in lowercase The resulting cassettes are then gel-purified, digested with SfiI, and ligated to SfiI-digested binary vector p7N (DNA Cloning Service, Hamburg, Germany). In the case of sequence 2_32, the promoter::GUSPlus::terminator cassette is subcloned into p7N using flanking HindIII and EcoRI restriction sites (see Table 4). p7N, in which the plant selection marker phosphinothricin acetyl transferase (bar) is driven by the relatively weak *A. tumefaciens* nopaline synthase promoter, is chosen as the backbone for these constructs to avoid potential cross-activation from the CAMV 35S promoter typically used to drive plant-selectable marker expression.

Figure 3:
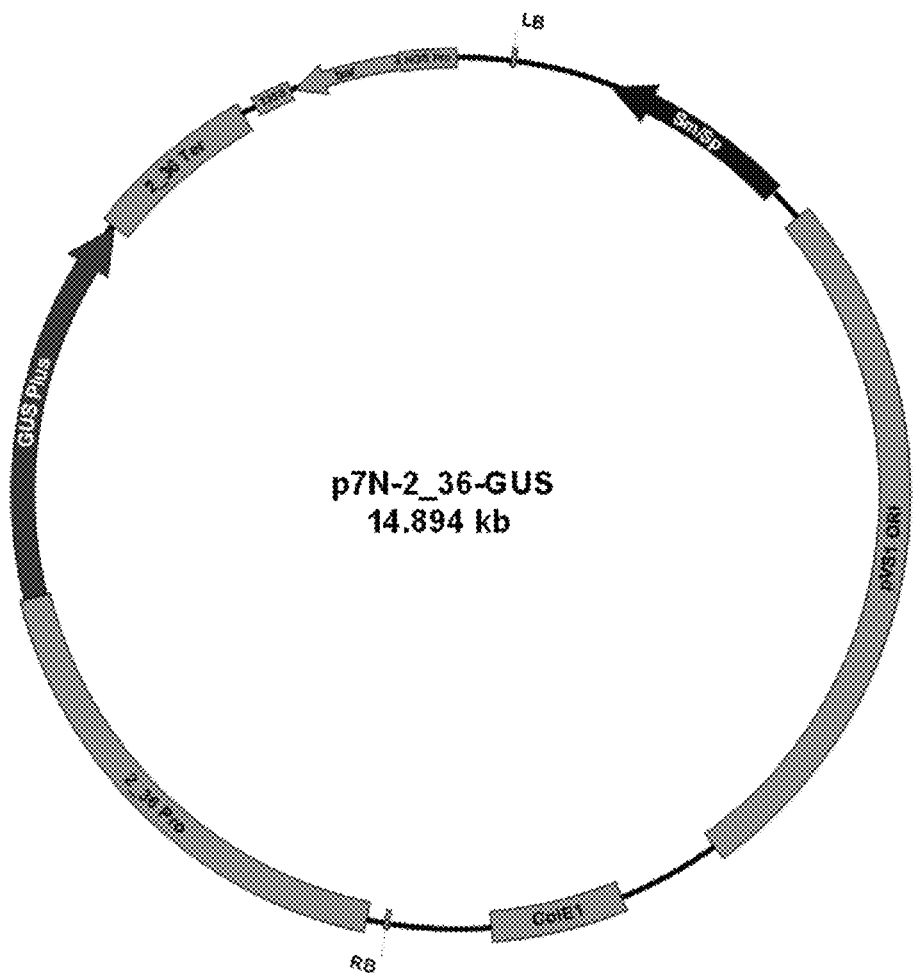
FIG. 3 shows a binary expression vector (p7N-2_36-GUS) constructed for evaluation of the 2_36 promoten:GUSPlus::2_36-3' cassette, where "2_36 Pro" is promoter, "GUSPlus" is 0-glucuronidase, "bar" is neomycin phosphotransferase plant-selectable marker, "2_36 Ter" is 3' flanking region, "NOS pro" is nopaline synthase promoter, "T35S" is CaMV 35S terminator, "pVS1 ORI" and "ColE1" are replication origins, "Sm/Sp" is streptomycin/spectinomycin bacterial-selectable marker, "LB" is left border, and "RB" is right border.
Figure 4:
FIG. 4 shows a binary expression vector (p7N-2_23-GUS) constructed for evaluation of the of 2_23 promoten:GUSPlus::2_23-3' cassette, where "2_23 Pro" is promoter, "GUSPlus" is β-glucuronidase, "bar" is neomycin phosphotransferase plant-selectable marker, "2_23 Ter" is 3' flanking region, "NOS pro" is nopaline synthase promoter, "T35S" is CaMV 35S terminator, "pVS1 ORI" and "ColE1" are replication origins, "Sm/Sp" is streptomycin/spectinomycin bacterial-selectable marker, "LB" is left border, and "RB" is right border.

The four binary vectors, p7N-2_32-GUS (FIG. 2), p7N-2_36-GUS (FIG. 3), p7N-2_23-GUS (FIG. 4), and p7N-2_35-GUS (FIG. 5) are made. In all binary vectors, "bar" is neomycin phosphotransferase plant-selectable marker, "NOS pro" is nopaline synthase promoter, "T35S" is CaMV 35S terminator, "pVS1 ORI" and "ColE1" are replication origins, "Sm/Sp" is streptomycin/spectinomycin bacterial-selectable marker, "LB" is left border, and "RB" is right border. For each binary vector, the promoter region and terminator region are obtained from the indicated contig (Table 2); 2_32 (FIG. 2), 2_36 (FIG. 3), 2_23 (FIG. 4), and 2_35 (FIG. 5), respectively.

Example 3. Generation of Genetically Altered Plants

The four binary vectors made in Example 2, supra, are used to transform *Arabidopsis thaliana* (ecotype Col-0) and *Oryza sativa* (cv. Nipponbare) to assess trangene expression in both a dicotyledonous and monocotyledonous host plant. *Arabidopsis* transformants are generated using the 'floral dip' method (Clough and Bent, *Plant J.* 16:735-743 (1998)) with individual genetically altered *A. tumefaciens* LBA4404 strains harboring one of each of the binary vectors described in Example 2. For generation of rice transformants, *Agrobacterium*-mediated transformation of embryogenic calli is performed as previously described (agron-www.agron.iastate.edu/ptf/protocol/Rice.PDF; updated Jun. 26, 2006) with recombinant *A. tumefaciens* EHA101 strains harboring one of each of the four binary vectors described in Example 2, supra.

Example 4. Assessment of Root Hair-Specific Promoter and Terminator Sequences in Genetically Altered Plants The spatio-temporal expression patterns and expression levels for each of the genetically altered plants are analyzed by histochemical localization and quantitative fluorimetric assays, using well-known in the art procedures (Jefferson, et al. (1987)). For both genetically altered *A. thaliana* and genetically altered *O. sativa*, a minimum of ten independent events are analyzed for each binary vector construct.

*O. sativa* (cv. Nipponbare) seedlings are maintained in growth chambers for 2 weeks at 25° C. under a combination of cool-white fluorescent and incandescent lighting at an intensity of approximately 400 μmol m$^{-2}$ s$^{-1}$ and a 16-hour photoperiod. To facilitate root system harvests, rice seedlings are grown using the synthetic medium Profile Greens (Profile Products LLC, Buffalo Grove, Ill.) and are fertilized twice weekly using Peters Excel 15-5-15 Cal-Mag (J.R. Peters, Inc., Allentown, Pa.) at 200 ppm nitrogen adjusted to pH 5.7. For harvests, pots containing genetically altered seedlings are briefly submerged in distilled, deionized water to remove all synthetic media from root systems, which are then excised, gently blotted on Kimwipes, and then either directly submerged in X-Gluc solution (Sigma-Aldrich Co., St. Louis, Mo.) for histochemical analyses, or flash-frozen in liquid nitrogen and stored at −80° C. prior to use in β-glucuronidase enzyme assays.

For all experiments, aseptically germinated *Arabidopsis thaliana* (Col-0) seedlings are maintained in a growth chamber at 21° C. under a 16-hour photoperiod and light intensity of 150 µmol m$^{-2}$ s$^{-1}$. Seeds are first surface-sterilized in 70% ethanol for 5 minutes, then rinsed 2 times in sterile, distilled water, followed by treatment with 0.5× bleach (3% sodium hypochlorite) and 0.05% Tween-20 for 10 minutes, then finally rinsed 4 times in sterile, distilled water. Following surface-sterilization, seeds are placed on top of an approximately 2.0 cm-high stack of 9.0 cm #4 Whatman filter discs and allowed to air dry in a sterile hood. Approximately 40 seeds are distributed evenly over the surface of a sterile 0.3 inn microporous membrane raft supported by a buoyant float (Osmotek Ltd., Rehovat, Israel). Seeded floats are then placed on liquid Germination Media (0.5× Murashige and Skoog salts, 1× Gamborg's B5 vitamin, and 1.0% sucrose (w/v), adjusted to pH 5.7 with KOH) in Lifeguard™ tissue culture vessels with 4.0 cm vented lids (Osmotek Ltd., Rehovat, Israel), cold-treated for three days, then transferred to growth chambers. After ten days, total seedling root systems are briefly washed in distilled, deionized water, gently blotted on Kimwipes, and then either directly submerged in X-Gluc solution (for histochemical analyses), or flash-frozen in liquid nitrogen and stored at −80° C. prior to use in β-glucuronidase enzyme assays.

Fluorometric quantitation and histochemical localization of β-glucuronidase (GUS) activity in genetically altered *A. thaliana* or *O. sativa* tissue isolated above are determined as follows. Extracts prepared from root systems of either 10-day-old genetically altered *A. thaliana* or 2-week-old genetically altered *O. sativa* transformed seedlings are fluorometrically assayed for GUS activity using the protocol described previously by Jefferson, et al. (1987). Fluorometric measurements are made using a Tecan SpectraFluor Plus microplate reader (Tecan Systems, Inc., San Jose, Calif.) calibrated with freshly prepared 4-methylumbelliferone standards dissolved in 0.2 M Na$_2$CO$_3$. The protein concentrations of extracts are determined using a Bio-Rad protein assay kit (Bio-Rad Laboratories, Inc., Hercules, Calif.) with bovine serum albumin standards. Histochemical localization of GUS activity is performed in overnight incubations at 37° C. in a humidified chamber, as described by Jefferson, et al. (1987). Following incubation in X-Gluc solution, tissues are cleared with 70% ethanol overnight with gentle shaking at room temperature, and stored in 70% ethanol at 4° C. prior to photomicroscopy.

For genetically altered *O. sativa* plants, two week old roots containing 2_32 promoter and 3' sequences (FIG. 6A and FIG. E), 2_36 promoter and 3' sequences (FIG. 6B and FIG. 6F), 2_23 promoter and 3' sequences (FIG. 6C and FIG. G), 2_35 promoter and 3' sequences (FIG. 6D and FIG. 6H) clearly have GUS activity within root hairs (FIG. 6A through FIG. 6D), and within developing trichoblasts proximal to the root apices (FIG. 6E through FIG. 6H). Significantly, the observation that all four expression vectors encoding GUS-Plus operably linked to the specific promoter and 3' flanking sequences are active in both immature and mature, root hair-bearing trichoblasts indicates that transcription activity is not restricted to specific developmental stages in this cell type.

Figure 7A:
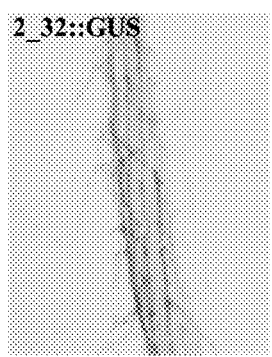
FIG. 7A and FIG. 7B show histochemical localization of GUSPlus reporter gene activity in 10-day-old genetically altered A. thaliana seedlings containing the 2_32 promoter:GUSPlus::2_32-3' cassette.
Figure 7B:
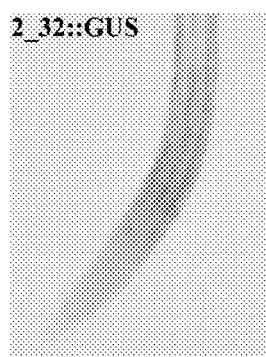
Figure 7C:
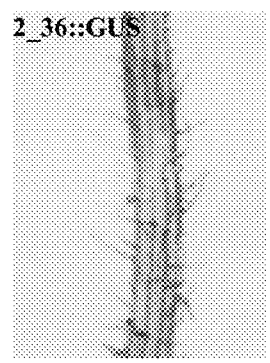
FIG. 7C and FIG. 7D show histochemical localization of GUSPlus reporter gene activity in 10-day-old genetically altered A. thaliana seedlings containing the 2_36 promoter::GUSPlus::2_36-3' cassette.
Figure 7D:
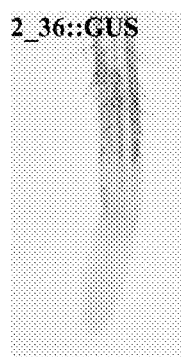

A similar analysis performed using 10-day old seedlings' roots from genetically altered *A. thaliana* containing either 2_32 promoten:GUSPlus::2_32-3' cassette (FIG. 7A and FIG. 7B) or 2_36 promoter::GUSPlus::2_36-3' cassette (FIG. 7C and FIG. 7D) indicates that these two promoter/terminator combinations accurately directed root hair-specific expression in a dicotyledonous plant. FIG. 7A and FIG. 7C show genetically altered *A. thaliana* root segments containing root hair-bearing trichoblasts transformed with 2_32 promoter:GUSPlus::2_32-3' cassette (FIG. 7A) or 2_36 promoten:GUSPlus::2_36-3' cassette (FIG. 7C). FIG. 7B and FIG. 7D show genetically altered *A. thaliana* root apices showing immature trichoblasts prior to root hair initiation transformed with 2_32 promoter::GUSPlus::2_32-3' cassette (FIG. 7B) or 2_36 promoten:GUSPlus::2_36-3' cassette (FIG. 7D). This transcription expression in a dicot suggests evolutionary conservation of the regulatory mechanisms controlling the expression of at least two genes investigated.

For 10-day old seedlings' roots from genetically altered *A. thaliana* containing either 2_35 promoten:GUSPlus::2_35-3' cassette or 2_23 promoten:GUSPlus::2_23-3' cassette, very faint staining is, however, inconsistently observed following overnight incubations, suggesting that these promoter/3' flanking sequence combinations might accurately direct expression in *Arabidopsis* at levels below the limit of detection of the histochemical assay employed.

Figure 8A:
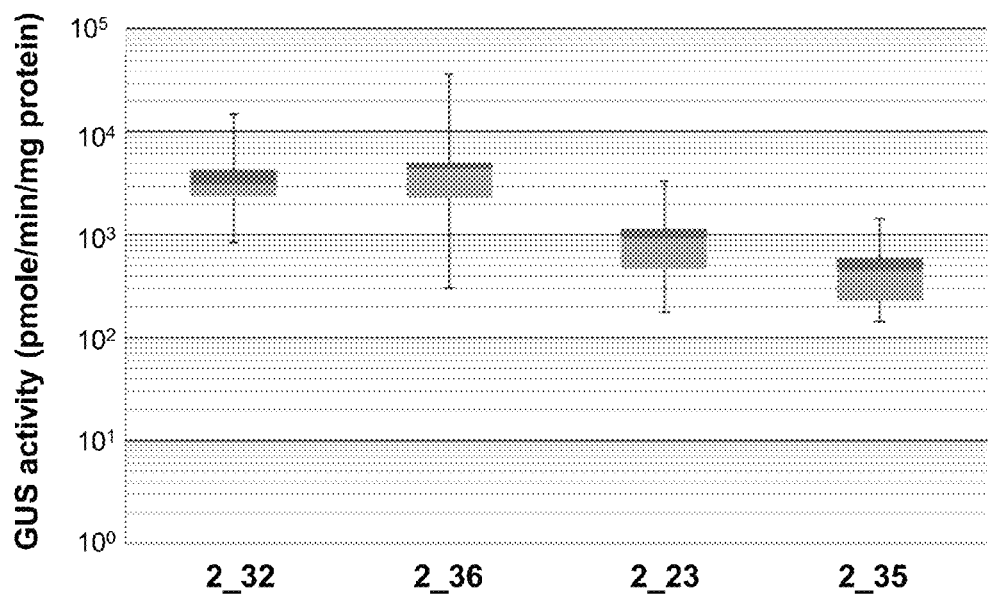
FIG. 8A and FIG. 8B illustrate the level of β-glucuronidase (GUS) activity in the root system of 2-week-old genetically altered rice seedlings (FIG. 8A) and 10-day-old genetically altered Arabidopsis seedlings (FIG. 8B). The rice and Arabidopsis are individually transformed with either the 2_32 promoten:GUSPlus::2_32-3' cassette, 2_36 promoten:GUSPlus::2_36-3' cassette, 2_23 promoten:GUSPlus::2_23-3' cassette, or 2_35 promoten:GUSPlus::2_35-3' cassette. GUS activity is measured fluorometrically, and specific activities are calculated based on extract protein concentrations. Box-whisker plots for each genetically altered plant indicate the minimum, first quantile, median, third quantile, and maximum GUS activities observed in populations representing multiple independent transformant lines.
Figure 8B:
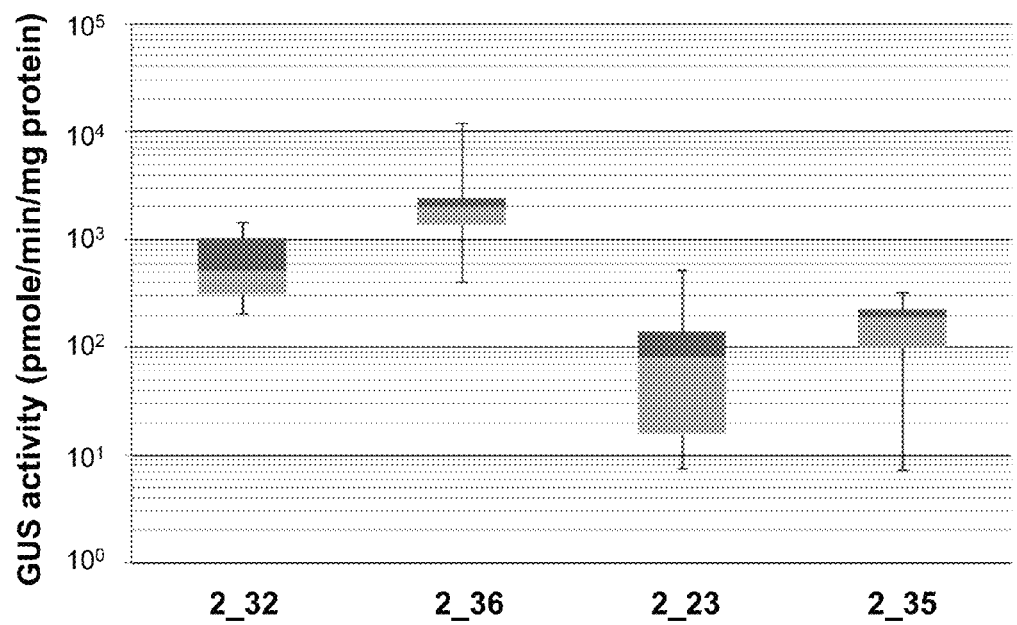

In contrast to rice, *Arabidopsis* trichoblasts develop in columns along the root axis and undergo extensive cell elongation (Dolan and Costa, *J. Experimental Botany* 52:413-417 (2001)), hence GUS histochemical staining appears as stripes along the surfaces of *Arabidopsis* roots (see FIG. 7A though FIG. 7D). As is observed in the genetically altered rice, in genetically altered *Arabidopsis* containing the 2_32 promoten:GUSPlus::2_32-3' cassette or the 2_36 promoten:GUSPlus::2_36-3' cassette, staining is clearly visible in mature, root hair-bearing trichoblasts as well as immature trichoblast cells in proximity to root apices.

β-Glucuronidase (GUS) activity levels in roots of the genetically altered plants are also determined for experimental groups comprised of multiple, independent transgenic events harboring each promoter::GUSPlus::3' region expression vectors in both rice and *Arabidopsis*, to examine the relative strength of each root hair-specific promoter/3' flanking region combination (see FIG. 8A and FIG. 8B). For these experiments, quantitative fluorometric assays are performed to determine GUS activity levels in genetically altered seedlings grown either in synthetic media (rice) or aeroponically (*Arabidopsis*) as described above to circumvent the potential loss of root hair cells during root system harvests. Significant differences in GUS activity levels directed by each promoter::GUSPlus::3' region cassette are then identified via non-parametric analysis of variance using the Kruskal-Wallis test (for overall significance) and the Mann-Whitney U test (for performing pairwise comparisons; p<0.05). As seen in FIG. 8A and FIG. 8B, box-whisker plots of GUS activity for each genetically altered plant indicate the minimum, first quantile, median, third quantile, and maximum GUS activities observed in populations representing multiple independent transformant lines.

As shown in FIG. 8A, the highest median GUS specific activity levels are found in populations of genetically altered rice seedlings containing the 2_32 promoten:GUSPlus::2_32-3' and 2_36 promoten:GUSPlus::2_36-3' cassettes, which are both significantly more active than populations of genetically altered rice seedlings containing either the 2_23 promoten:GUSPlus::2_23-3' or 2_35 promoten:GUSPlus::2_35-3' cassettes. Although median GUS activity values are higher for 2_32 promoten:GUSPlus::2_32-3' cassette transformed rice relative to 2_36 promoten:GUSPlus::2_36-3' transformed rice, these differences are determined to be insignificant (p>0.05). Additionally, median GUS activity levels determined for 2_23 promoten:GUSPlus::2_23-3' cassette transformed rice are significantly higher than those levels observed with 2_35 promoter::GUSPlus::2_35-3' cassette transformed rice. Taken together, the data indicate a hierarchy of 2_32 promoten:GUSPlus::2_32-3' cassette=2_36 promoten:GUSPlus::2_36-3' cassette>2_23 promoten:GUSPlus::2_23-3' cassette>2_35 promoten:GUSPlus::2_35-3' cassette for relative promoter/3' flanking combination activity in genetically altered rice plants. Of further significance, these results are in general agreement with the RNA-seq mean FPKM values determined for the respective endogenous transcripts (see Table 2), indicating that the use of the approximately 2.5 kb promoter and 1.5 kb 3'-flanking sequence in the transgene cassettes accurately confer the transcriptional activities of the endogenous S. bicolor genes.

As seen within the genetically altered rice transformant populations, genetically altered Arabidopsis plant seedlings harboring either the 2_32 promoten:GUSPlus::2_32-3' and 2_36 promoten:GUSPlus::2_36-3' cassettes exhibit significantly higher median GUS activity levels in roots than the roots of the genetically altered Arabidopsis plant seedlings carrying the 2_23 promoten:GUSPlus::2_23-3' or 2_35 promoten:GUSPlus::2_35-3' cassettes. See FIG. 8B. However, the roots of genetically altered Arabidopsis plant seedlings containing 2_36 promoten:GUSPlus::2_36-3' cassette also exhibit significantly higher median GUS activity levels than the roots of genetically altered Arabidopsis plant seedlings containing 2_32 promoten:GUSPlus::2_32-3' cassette (FIG. 8B). In contrast with the results obtained from genetically altered rice (FIG. 8A), the median GUS activity levels in roots for 2_35 promoter::GUSPlus::2_35-3' cassette transformed Arabidopsis plant seedlings are higher than 2_23 promoter::GUSPlus::2_23-3' cassette transformed Arabidopsis seedling roots, however these differences are determined to be statistically insignificant (FIG. 8B). Additionally, the data indicate a hierarchy of 2_36 promoten:GUSPlus::2_36-3'>2_32 promoten:GUSPlus::2_32-3'>2_35 promoten:GUSPlus::2_35-3'=2_23 promoten:GUSPlus::2_23-3' for relative promoter/3' flanking combination activity in the dicotyledonous model Arabidopsis. Taken together, the data clearly indicate that both the 2_32 promoter:GUSPlus::2_32-3' and 2_36 promoter:GUSPlus::2_36-3' cassettes exhibit the highest root hair-specific activity in both a representative monocot and dicot host among the four expression vector constructs, and the 2_23 promoten:GUSPlus::2_23-3' and 2_35 promoten:GUSPlus::2_35-3' cassettes would, perhaps, be more suitable for situations when lower levels of heterologous gene expression is required or desired.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. All documents cited herein are incorporated by reference.

We, the inventors, claim as follows:

1. A cassette comprising a promoter operably linked to a heterologous polynucleotide; wherein said promoter comprises SEQ ID NO: 7; wherein said promoter is capable of regulating transcription of said heterologous polynucleotide in a plant cell; and wherein said heterologous polynucleotide encodes a protein or RNA.

2. The cassette of claim 1, wherein said promoter is active predominantly in a plant's root hair cells.

3. The cassette of claim 1, wherein said protein or RNA confers improved disease resistance to a genetically altered plant comprising said cassette and producing said protein or RNA.

4. The cassette of claim 1, wherein said protein or RNA confers enhanced nutrient uptake into root hair cells of a genetically altered plant comprising said cassette and producing said protein or RNA.

5. The cassette of claim 1, wherein said protein or RNA confers improved resistance to colonization by soil-borne parasites to a genetically altered plant comprising said cassette and producing said protein or RNA.

6. The cassette of claim 1, wherein said protein or RNA promotes colonization of beneficial rhizosphere-associated microorganisms to the root system of a genetically altered plant comprising said cassette and producing said protein or RNA.

7. The cassette of claim 1, wherein said protein or RNA confers improved stress tolerance to a genetically altered plant comprising said cassette and producing said protein or RNA.

8. The cassette of claim 1, wherein said protein or RNA confers enhanced water uptake into root hair cells of a genetically altered plant comprising said cassette and producing said protein or RNA.

9. The cassette of claim 1, wherein said protein or RNA is useful in bioremediation mediated by root hair cells of a genetically altered plant comprising said cassette and producing said protein or RNA.

10. The cassette of claim 1, wherein said protein or RNA promotes allelochemical production by root hair cells of a genetically altered plant comprising said cassette and producing said protein or RNA.

11. The cassette of claim 1, wherein said protein or RNA increases nitrogen fixation mediated by root hair cells of a genetically altered plant comprising said cassette and producing said protein or RNA.

12. The cassette of claim 1, further comprising a terminator operably linked to the 3' end of said heterologous polynucleotide; wherein said terminator has a DNA sequence selected from the group consisting of SEQ ID NO: 2, 4, 6, and 8 or a sequence that is at least 95% identical to SEQ ID NO: 2, 4, 6, and 8.

13. The cassette of claim 12, wherein said promoter is active predominantly in a plant's root hair cells.

14. The cassette of claim 12, wherein said protein or RNA confers improved disease resistance to a genetically altered plant comprising said cassette and producing said protein or RNA.

15. The cassette of claim 12, wherein said protein or RNA confers enhanced nutrient uptake into root hair cells of a genetically altered plant comprising said cassette and producing said protein or RNA.

16. The cassette of claim 12, wherein said protein or RNA confers improved resistance to colonization by soil-borne parasites to the root system of a genetically altered plant comprising said cassette and producing said protein or RNA.

17. The cassette of claim 12, wherein said protein or RNA promotes colonization of rhizosphere-associated microorganisms to the root system of a genetically altered plant comprising said cassette and producing said protein or RNA.

18. The cassette of claim 12, wherein said protein or RNA confers improved stress tolerance to a genetically altered plant comprising said cassette and producing said protein or RNA.

19. The cassette of claim 12, wherein said protein or RNA confers enhanced water uptake into root hair cells of a genetically altered plant comprising said cassette and producing said protein or RNA.

20. The cassette of claim 12, wherein said protein or RNA is useful in bioremediation mediated by root hair cells of a genetically altered plant comprising said cassette and producing said protein or RNA.

21. The cassette of claim 12, wherein said protein or RNA promotes allelochemical production by root hair cells of a genetically altered plant comprising said cassette and producing said protein or RNA.

22. The cassette of claim 12, wherein said protein or RNA increases nitrogen fixation mediated by root hair cells of a genetically altered plant comprising said cassette and producing said protein or RNA.

23. A genetically altered plant, part thereof, or its progeny comprising a cassette, wherein said cassette comprises a promoter operably linked to a heterologous polynucleotide; wherein said promoter comprises SEQ ID NO: 7; wherein said promoter is capable of regulating transcription of said heterologous polynucleotide in a plant cell; and wherein said heterologous polynucleotide encodes a protein or RNA.

24. The genetically altered plant, part thereof, or its progeny of claim 23 wherein said plant is selected from the group consisting of a gymnosperm, monocot, and dicot; and wherein said genetically altered plant, plant part or progeny comprises the cassette.

25. A genetically altered seed of said genetically altered plant or its progeny of claim 23; wherein said genetically altered seed comprises the cassette.

26. A genetically altered pollen of said genetically altered plant or its progeny of claim 23; wherein said genetically altered pollen comprises the cassette.

27. A genetically altered cell of said genetically altered plant or its progeny of claim 23; wherein said genetically altered cell comprises the cassette.

28. A genetically altered tissue culture comprising a plurality of said genetically altered cells of claim 27.

29. A genetically altered plant, part thereof, or its progeny comprising a cassette wherein said cassette comprises a promoter, a heterologous polynucleotide, and a terminator, wherein said promoter is operably linked to the 5' end of said heterologous polynucleotide; wherein said terminator is operably linked to the 3' end of said heterologous polynucleotide; wherein said promoter comprises SEQ ID NO: 7; wherein said terminator has a sequence selected from the group consisting of SEQ ID NO: 2, 4, 6, 8, and a sequence that is at least 95% identical thereof; and wherein said heterologous polynucleotide encodes a protein or RNA.

30. The genetically altered plant, part thereof, or its progeny of claim 29 wherein said plant is selected from the group consisting of a gymnosperm, monocot, and dicot; and wherein said genetically altered plant, plant part or progeny comprises the cassette.

31. A genetically altered cell from the genetically altered plant of claim 29; wherein said genetically altered cell comprises the cassette of claim 29.

32. A genetically altered tissue culture comprising a plurality of said genetically altered cells of claim 31.

33. A genetically altered seed from the genetically altered plant or its progeny of claim 29; wherein said genetically altered seed comprises the cassette.

34. A genetically altered pollen from the genetically altered plant or its progeny of claim 29; wherein said genetically altered pollen comprises the cassette.

35. A method of selectively directing transcription of a heterologous polynucleotide in root hair cells of a genetically altered plant and its progeny, said method comprising:
  (i) introducing a cassette into a wild-type plant cell to produce a genetically altered plant cell; wherein said cassette comprises a promoter and a heterologous polynucleotide; wherein said promoter is operably linked to the 5' end of said heterologous polynucleotide; wherein said promoter comprises SEQ ID NO: 7; and wherein said promoter selectively directs transcription of said heterologous polynucleotide in said genetically altered plant's root hair cell; and
  (ii) selecting a genetically altered plant cell that contains said cassette;
  (iii) growing said genetically altered plant cell into said genetically altered plant; wherein said heterologous polynucleotide is transcribed predominantly in said root hair cells of said genetically altered plant.

36. The method of claim 35; wherein said introducing said cassette occurs via transforming said wild-type plant cell with said cassette.

37. The method of claim 35; wherein said wild-type plant is selected from the group consisting of a gymnosperm, monocot, and dicot.

38. The method of claim 35; wherein said cassette further comprises a terminator operably linked to the 3' end of said heterologous polynucleotide, and wherein said terminator has a polynucleotide sequence selected from the group consisting of SEQ ID NO: 2, 4, 6, 8, and a sequence that is at least 95% identical thereto.

39. The method of claim 38; wherein said introducing said cassette occurs via transforming said wild-type plant cell with said cassette.

40. The method of claim 38; wherein said genetically altered plant is selected from the group of a gymnosperm, monocot, and dicot.

41. A method of producing a protein or RNA of interest predominantly in root hair cells of a genetically altered plant, said method comprising
  (i) introducing a cassette into a wild-type plant cell to produce a genetically altered plant cell; wherein said cassette comprises a promoter and a heterologous polynucleotide encoding said protein or RNA of interest; wherein said promoter is operably linked to said heterologous polynucleotide encoding said protein or RNA of interest; wherein said promoter comprises SEQ ID NO: 7; and wherein said promoter predominantly transcribes said heterologous polynucleotide encoding said protein or RNA of interest in a plant's root hair cell;
  (ii) selecting a genetically altered plant cell that contains said cassette; and
  (iii) allowing said genetically altered plant cell to grow into a genetically altered plant that produces said protein or RNA of interest in said genetically altered plant's root hair cells.

42. The method of claim 41, wherein said introducing said cassette occurs via transforming said wild-type plant cell with said cassette.

43. The method of claim 41 wherein said genetically altered plant is selected from the group of a gymnosperm, monocot, and dicot.

44. The method of claim 41; wherein said cassette further comprises a terminator operably linked to the 3' end of said heterologous polynucleotide, and wherein said terminator has a polynucleotide sequence selected from the group consisting of SEQ ID NO: 2, 4, 6, 8, and a sequence that is at least 95% identical thereto.

45. The method of claim 44; wherein said introducing said cassette occurs via transforming said wild-type plant cell with said cassette.

46. The method of claim 44; wherein said genetically altered plant is selected from the group consisting of a gymnosperm, monocot, and dicot.

* * * * *

SEQUENCE LISTING

<160> NUMBER OF SEQ ID NOS: 75

<210> SEQ ID NO 1
<211> LENGTH: 2500
<212> TYPE: DNA
<213> ORGANISM: Sorghum bicolor

<400> SEQUENCE: 1

```
acactagaat cactctccca ctcaatcaga tgatcactat caagcataag tgagttagag     60
ggctcccaag cgccaccaca taagccacca aggccctagt gggctcagca actagccaaa    120
gggcggccac acttctattt atagccacaa gggctaaaca agccgttgcc ccttcactag    180
gcaaaacgcg ggggcgtcgg acgcaccacc ccagtgtccg tagctcatga agcagccacg    240
tgctactagt cgtttgaact taaccgttgc cgccaacggc taactcacac gtgccgaggg    300
ataggacgtt ctggcacaac ttgtcggacg ctagcacctc acgtccgacg ctgcttagag    360
agttcccaaa cttggttaca caccatcgga cgtgtctgac gggtgatcat cggacgcgtg    420
ccagcgtcct acacgtacac ctcgcaaaac gttgcgtgcg ttggacactc attagtactc    480
ggtcagcatc cgacacaaaa ccttcggaca tgccaatgca cagtgcaact ctatcacaca    540
ttgtcgaacg caggtctagc gtccaacgct gccaagtctt gctcaagctt agctgtcaca    600
cgcggtctct cgcttcaaag cctccgactt gcccttcaca catgcaatca gtccgtcaag    660
ccaagcctta tctagatctt ctccatcttg gtcacatgac tccatgtcat gtctcatatg    720
caatgagctc ctccatcatt acatattcac ctatagacta atctcctgtg tatctcacat    780
aaaaactatt agtccaccta agttattcaa ttaccaaaac caaacaagaa ccttttagcg    840
```

```
ggtaactttg acaaaaagtt tgaagacaca acagatgtca atgatgtgca tgatccggat      900
gactttggcc atgattttca gtgaggaaga gaaaggctat agaacataga taaggcatga      960
ctgtgtttgt gatcgaggga ggtagtttag taaagaattt ttggtgtata ttataaagaa     1020
agtagtgata aaaaggatag ttttggtgt ctacactaat aaattaatca agcatgcatg      1080
gacccaacta tatatcctaa tcctaatggt ataatggtaa ataatccatt catggtccat     1140
gatccttgga tttgggtcca tggcaattca aaaactagct atctctctct ctctctctta     1200
gtctctctgc caaagatatt tgaagcacat tctgacggca ataaaaaaag acgtaaaact     1260
agcgggcgat gaactcattc accattacaa ccattaaatt taatgcaaat taagtaccgg     1320
tttaatatag aaaattatga ataacatgtt ttgtgacatc tgacatgtgc atgtgtgtac     1380
atgtttctaa ttatcatgat tttaatcata gaaaacaaag gacggtttgc aacaacatac     1440
ccaacgacac taaagctgac gctagttgcc atagaggttg tctatgtagc acaaccaagc     1500
taggatttag tgaggggtct acctagaagg cgcatccgac aaagaagacg agaaagacga     1560
tgtggtggca agggagcccc tcctcggatg gctgcatggg aaggcgctca acaaggat      1620 ggtggtggat ggagacgagg aaaaaggtcg agccagggaa aagaacgga gatggtgcca      1680 gacctcgact gtgaaatcta ggaccagtgc ctcttgtgaa atcatttgtg cagcagtgtt     1740
acttttccga gctaagaagg ttggtccatg tggctcaaat taaagttgat ggataggcca     1800
gtgatcaagc aatgtagacc caaaggttgt gtccgaaatt ttcatttacg tttcaatgtg     1860
gtttctaaaa aaataatttc aatgctacac caaaacataa gaattataga gttttgtcgt     1920
ggctttgaaa cttcttccaa tcgtgctagt ttaatttgta tatcaggacc atgctattcc     1980
tctggccttg gttcttgcgc atccattcta aatgagcacg cgccacgcca cacattcctt     2040
cttaatcacc agctgcttcg ctagcttgac atccaatgtc ctgggcacca ctccgtcgga     2100
tccgccagga tgcccagctg aaatgatgcc taatgatcat atgaaaacaa atattagtat     2160
acgagctggc catttgcgga gccaaccgaa gtcgtcgtgc acaaaatatt tgataccgta     2220
tcacggaaaa cactaaatat acgatgtagg caataatcta gaacggactc ttcctcaccg     2280
gtcgggttca cctgtatata tttgaatatg atgactcggt tcatttgaac actatcgtgc     2340
ctagtagtgc accgatttct taatcctaag gctggactat aagtatccct ggtaacaccc     2400
cgtgatcaaa gcatcgcaaa ctagctgcta atcacttgtc aagagctctc tgaccatatt     2460
agctctagag tgatccgcga gctggtgtga tcgagcaata                           2500

<210> SEQ ID NO 2
<211> LENGTH: 1660
<212> TYPE: DNA
<213> ORGANISM: Sorghum bicolor

<400> SEQUENCE: 2
tgagcgcctg gatctcagcg ccttgagaca tcttgtcttt taatttcagc tcggttttaa       60
tgatgcgttg ttatttgatt gcttttccac gtagtatgat gtacgactag tcagcataca      120
tgcatgcacg catggccggc cgtgctgtca aattgtatt ttttcatttg ttgaaaaaaa       180
gccggcgatc acttgtatgc cggtgctaag ttccaatcaa gttggtttg cgatttattt       240 cacagtttcg catgcatgtt ctggttatat tctagtcgta cttgagcata tgaaaacgta      300
ctgtctacca cgtacttatt ctcttgagtg tcactgagaa ggaatgtgtg ttggtaagct      360
ttcttgaatc tgacaaatta tgtaaaataa atattatcaa tatttacatc ttcacgtagt      420
```

-continued

| | |
|---|---|
| ttataataaa aatatattta ccgatctatc taatgatact aatttacac cataaatact | 480 |
| aatatttctg tatatatatt tagtcaaaat ttaaaatgtt taacttctca gaaggtgaga | 540 |
| atgatactat ttgtcagacg gtggtgcggg gtgtcggaca aaaatcagac ggtggcgcag | 600 |
| tgcatgcggc cactagcagc ggtgcgcgat ccacacttcc tccagcgcag cgtttggggc | 660 |
| aatcggcgat ggcacgcagg ccctatgtcg gtagtacgct gctcccttcc tctagtgagc | 720 |
| gtggatccga cgagcggatc cagcgacaat ggcagcacgt gaatgggctc ggcgggcctt | 780 |
| gtggataggc ttggagggcc tcatcgatgc gcatgccatt tcttattttg ttaacacaga | 840 |
| tgagcaagtg tccgcctgca taaatcttga tttatactgg tgttgaagga gaggcagacg | 900 |
| tactggctgc ccgactccaa aaccaatta tggtcaccta ggaaaattgc tattgtggtg | 960 |
| gtgttaaccg ataaaacatc taaagctatt tttttagaag ctactgcttt cacagtataa | 1020 |
| ttttcacacc ttgaacccta cttcttgctt tcagttattc caacttccaa atgggtggaa | 1080 |
| atatagcaac atttcataat catttcaaga gagattagat tggataggta tgaggggctc | 1140 |
| atcctcctta tcttttgcat ttagcaattt cttttaaact ttaatagcta caaacttata | 1200 |
| ggagaggctt tacatttcca atggcagtaa gaggggctcg acgccgctcg actacgtgct | 1260 |
| agatccaccc ctaataggtt ttgtagttgc tttaaccaaa caacttataa tttttctaga | 1320 |
| gcgcatagct cacatgagct ttttcatagt tatctggtga cagttgaact atacagaccc | 1380 |
| ggagttaagt cgtctgcgaa ctaagagcca ctcaactgcc tcctctcttc ctcatccatg | 1440 |
| catgagccac taatgcatca ctcttccgtc cccatggatg atgcacaccg cttcgccgcc | 1500 |
| tctgtccctc agccatgctt gtcttgcttt gccacctgtg tcttttctcc atgtgcgtta | 1560 |
| tacatgggcg gatccatata ggatctactg ggtgcggcca cacccagaca aaaatacaaa | 1620 |
| atatgctata ctttgcatgt ttctatggta ttcgcacccc | 1660 |

<210> SEQ ID NO 3
<211> LENGTH: 2543
<212> TYPE: DNA
<213> ORGANISM: Sorghum bicolor

<400> SEQUENCE: 3

| | |
|---|---|
| ttagctagat cggatggtta agaacctagt aagaggaact taagttgtag gctagaacca | 60 |
| aaatttagta gacctagagc cagctctagt taaattgtaa gggtgcgcat aactccataa | 120 |
| tccataattc tagccaccca ttgtgtcgcc gacccagagt cccagactag gaatcgacgc | 180 |
| ggacaggcag gcagccctct ccgactccgt gggcaccgtc gtcgcagcta ctcgttgctc | 240 |
| cgtctacgaa agaatcaatt tttaaagttg ttctaagtca aacttttaa actttaacca | 300 |
| aatttctaga aaaaaatact aagatttatg gtatcaaatt agtatcatta gattcactat | 360 |
| agaatatatt ttcatatgat acgtatttta tatcatagat ttgttaccat tttctataaa | 420 |
| attagtcaaa cttaaaaaag tttgacggat acggattcta agaattgatt cttttatgga | 480 |
| cagagggagt acatacagca ggctgtgtct gtgcaaacgt ccggcttcta cgacgggcgg | 540 |
| ccaggttgag gtcttgttta gatccaaaaa gttttggat tttaacactc actttcattt | 600 |
| ttatttgaca acattgtcc aatcatagag taactagact aaaagattc gtctcgcaat | 660 |
| ttacagacaa attgtgcaat tagttttttt tatcatattt aatgctctat gaatatacca | 720 |
| taagattcga tgtgataaaa aatcttaaaa aaattgtttt tttagtaaac taaacaatgc | 780 |
| cgtgccgtgg gcgtgggcgt ggagaacatg caatgcattg catggggaac atcgatgaac | 840 |
| caaagttaat gggcacacta aactgcatgc cccagacaca gttttaaaat ttatttacta | 900 |

```
atatagcaac aaaaaaaaac aaatatatgc acgcccgcac gcacgtcctg tgcatatata      960
tatgcacgga cgctattcaa atcaacaggg agaggacagt ttggtcggtg gagtatctat     1020
ctacactaaa aaataccgcc ctcctctact cagctcgtcc ccgatttttt taactcctcc     1080
tccaaatcac aatcagatat caaatcaaat caaatcattc taaatcgaaa aaaaagaaa      1140 atattaaatc aaatcaagaa aaaatataag tcaaatacac agaatatccc atcatgctca     1200
tcttgtcctt ggatattttg actctctcct ccaaatcaga atcggatatc aaatcaaatc     1260
aaatcgttct aaaaccgaat aaaaaaaaga aaatatcaaa ccaaatgaaa tgaaatcgag     1320
aaaaaaaaaa tcaaatatgc agggtatcgt agtaccatcc tactctgttc agctcatccc     1380
caaatttttt ttgccttgct cctcgaaatc agaatcgaat atcaaatcat tctaaatcca     1440
aatcagaaaa agaaatatca aaccaaatta atgaaatca taaaaaaata taagtcaaat     1500
atgcaaagta tcattttgac tcgctcctcc aaatgagatc gaatatcaaa atcgaatcaa     1560
attgtttgaa atctgaattt taaaaaataa aatatcaaac caaatcaaat gaaatcggaa     1620
aaaaatacaa gtaaaataca cagggtattg tcgtaccacc ctgctttact caacttgtcc     1680
ttggattttt ttgcatgtct cctccaaatc agaatcggat atcaaatcat atcgttccaa     1740
atccgaattg gaaagaagaa aatatcaaac caaatcaaat gaaatagaaa aaaaatacaa     1800
gttagtgtgt tgttgcaact gtattgaaac ttgacctctt gccgcctgcg cgagggctcg     1860
tgaactagca ggctgtcact gtaaaaataa tagtatcagg tacaataaca gtgtgattcg     1920
actgttatat cattcatata cacgtaaaag cggagagaga aagcaatgct tttgttgatg     1980
agcttgtgac gcatgtcaag acgcttttc taagcagagg ttaactcttc ccatcctatc      2040
cttgtatatt gaataagaaa acaatattta gactatagaa agggactaat tgttgtatgt     2100
gctagactct aaataaactt gtctaataat gacttggctt ggcttataga taaattttat     2160
taggcttgct ctaaaacctg ccctcacaca tgatccgaaa cttgtggggc aataaaaagc     2220
gaaactattc tgtatattaa gctcgtgctt tgtgctacct gaaaaaaat acaaacaggt      2280 aagccattgc gtaacaaaaa aaaaatgaaa agaacaaaga aacaattaag aaatccgcct     2340
acctgatcgt gcattgtgct cggttactaa tgtactttt aaaaattgga atggatggat      2400
ggttttcctc tgactggctg gctggctgcc tgctgcttat aggagtacta tataagtaga     2460
cgcatgcagt acccaaacga cgacgccgcc accaccgcaa aagcagcaaa accttagctt     2520
gttcaccacc acaaccgcca gcc                                            2543
```

<210> SEQ ID NO 4
<211> LENGTH: 901
<212> TYPE: DNA
<213> ORGANISM: Sorghum bicolor

<400> SEQUENCE: 4

```
cttgcatcat tgctgggagg gatccattcc atgcctgcgc tttgccagct gggaataatg       60
atagatgccc gtacgtacgt ctcgatatgc atacggttga tgttggtgtt gaataccctcg     120 cgctctcgta ttcgtatacg gagtagtagg tgaagtcagt tggtgcaatg tattccatct      180
gttcgtggcc tatatattat gcaaaaaaat aatgtcagaa taattaaatc acatgtgtga     240
gattgaataa ataaccaatt tctccgcatc gtttatatat taattgtaca gtatatatag     300
taggatcagg agtaatgcat gcttagctac tctatatacc tctcaaaaac gattgtgtac     360
tataaattca taataggcga aggacctgct gtataaacgc tgctggggtt accggccggg     420
```

```
catatacata tcctcctttc ttatcagcaa ggcctgctgt actaaattca taataaggac    480
cccagcagcg tttcgatcgt cgacatacat atctcctacc tacagcttct tcgacggaca    540
aaacttggtg tcttgctgtg gatttataat gggcttggcc catatacatt tagtaaatca    600
ataaactcgg tgtataatta atacaatacg ggatatattg ataaaacatt aactagactt    660
atatggttgg attttatcct tctatattga aagttgaga  aaagtacaaa ggcgtgccac    720
acgtgcgcgc actgccgccg cccaggccgt gccgccaatc aaaactcata taacgtgag    780 tttcttcttt tgtattatca cgattaatct ttgtctgtta cgaactcttt gcttgtttgt    840
ctgtctcttg agttgactgc gatcccttct cctgcctcta cctgcgagaa taaaatctcg    900
a                                                                    901

<210> SEQ ID NO 5
<211> LENGTH: 2521
<212> TYPE: DNA
<213> ORGANISM: Sorghum bicolor

<400> SEQUENCE: 5
tctgggtact gctattgagg ccttgtctcc caaaatgggg cttgaatatg catgagtata     60
agaagacaga taacttgaa  cacatgtcaa caagggacca caatcaaag  tattatattg    120 tattcaagta ctttgcta   ttatatctta tagaatatat tatatattct ccaacgccat    180
aatttcataa tagatgggta gccacggttc atcctgggct aagtttcaac ccaactggaa    240
caatttgtaa ctttattgtg tcgtaattgt atcagcttat ggggttagcc attctaccct    300
atgtaataat atatgtttat atgttgcaat gcttatggtc ctaaggtttc actaagtgct    360
tatcattgtt ggctgcatca ccgccagtct gttagaaaaa aggacatcac gccaggttta    420
taaaccaact gtagtgaata tagcgacata atttgagata tcattgggat ttacatatcg    480
tttctttttt ttttcttttc acaaagcact tagccactta ggacacttcc tttcttcctt    540
ccttccttta agctggacta ggaaacacaa agagtctggg ccttgacgat agcatggatt    600
gggacgactt tgtcttttgg gcttcttggt catcatcgtc tccatgcgtg tgccaccagc    660
gttcccgttg ccctcctcat cctttctgac agatgccccc ttggtaccgt gacatttctc    720
tcttcttgag aaccggcttg acccaagcca gtgccaccgg aaaaatgagc ttcagcacgt    780
gctcattctc ctaggttgac gtacacaagt gcacgggcca ttctgaccaa tgaacaagaa    840
cttgattgaa acagaaactt catcattgcg tctacacact tagcataatg attagtccta    900
agatttcatt aattattaaa atcaaactag gctttcata  tgggtacgta ccctatgtct    960
acttgaagca ggccttgaca caagagtcca agaaggcata ttccatagtt ctacgattgt   1020
cgtcggtgtc ctcttggtaa cagcgattcc ctccttggtc aatctgctgg tgatcgcgat   1080
gaccctgtca atgagatcgg aggagacatc gggcaacaac ctcctctta  agactcggtc   1140 acctgacctt tgttgagatc atcccaacac aaactgctaa aaatctcggt tcacgatttg   1200
atccatcatc tgaagcaagt gcaaacataa ttgctgattt tgtgtcaaat gagaaatata   1260
atgcaatagt gatgtgaagt atatacccct tcttttttt  aggaaacgct aatggtttga   1320
tgacaatttt gttgtgcttt ttactttctt ttcacattta ttttgtactt ctgattttt    1380 aaagtgtaaa acacaattac tttgaagaat tgggaaacaa tcagctcatg actccagcag   1440
taaaaaaggt taaactcgaa aaaaggggga aatgatggt  ttcatccgtg actttgaaga   1500
ttcatgaatc ggagtaaaaa aagaagaatt gtgaatcaca aacccttttgg ctcttgtatt   1560 cgaaaaagtg ggtcctgtta ctcctgtagg tgtcatatgt gacaaaaatt atcatagctc   1620
```

| | |
|---|---:|
| aaagaaaaaa aactgtaaac aaaaatggct acccacctgt ttcgtgacgt ggtggctctt | 1680 |
| gtacatatat ataggggtg tttgagattg ctctgctcca aattttttta gctccgcttt | 1740 |
| atgttttta gtcaaacagt ttcaggtcca cgcactcagt tttaaaaaaa tggtggagtt | 1800 |
| gtgagagcac ctagagaggt actctacaaa ctccggtttt tgtgaagct gtttcatggt | 1860 |
| ggagtttgtg gagcagagtt cgtgaagcaa tgccaaacac ctagtaacat ggtgttgtac | 1920 |
| gtggccgaaa ccaccgtagt tgaaaaaaca aaaccgtgg aagcaaaagc cgctataggg | 1980 |
| taacttaata agctcattaa catacggtaa cacaaacaaa gaagaagttt tcacacgtgt | 2040 |
| gtgttatatt tttctgttca gattacccaa gatcggagat acgttttga attaggattc | 2100 |
| ctttcggcgg agagacgttt ttgaattagt aaaaataaaa atataaaaga tacgctgccg | 2160 |
| atgcgttttc gatacatatt ggagaagtat cagaaaacaa aataaaaata acacaaaatc | 2220 |
| tgatagtcgt gagggggatat gtatatcagc ctggtcaact cacgccggcc ggtactactc | 2280 |
| tgtgagggct gccactactg cttatcggag aagtattcat cagaaaataa aaacaaaaaa | 2340 |
| cctgatactc gaggatatgc tacgtatcac aactcacgca gatacgacgg ctagctgaac | 2400 |
| agcccacacc cacaccctct ttataaatgc atggctcatg cggcgctgct ccatattgct | 2460 |
| cccattcatc ctcgtcctcc acgagcctgg ctcacaggct gtacgtcgtg cgtcgtcgtc | 2520 |
| g | 2521 |

<210> SEQ ID NO 6
<211> LENGTH: 1441
<212> TYPE: DNA
<213> ORGANISM: Sorghum bicolor

<400> SEQUENCE: 6

| | |
|---|---:|
| tagcagagga acttactgtc acaacgcctc tgccaagtcc aataatgtgg atccgtggcc | 60 |
| ccatggccgt ctacttatct atactgtact tgaatcaata atctccttgg acatatttgc | 120 |
| catgacatgt caaataattt ctacacgact tttgatttat ggatcaaaaa actgttgcaa | 180 |
| ccttgctctt cttgttttac tcttttttta tctttttta tttcctaagt tgttgtactg | 240 |
| tgttttcctc tttttaattt caataaatct cctatagggg ctaaggcccc tccagttctt | 300 |
| tttttaaaaa ataatttta ccacttgtgg agatattcta aattcactgt tcataggctt | 360 |
| ccatttgtat tgatcgagac attgagtgga gtgccctatc cttccacccc accctctgct | 420 |
| ggtcctcttt attaagggat ccgtctatat ttgacttgag tgatgtccgt gttttgtaaa | 480 |
| ctaaatagtg aatttatacg tatcgtgtag ctttaggaag acgacactta tagacacgag | 540 |
| ggttatactg gtcaggcggc cgcagcccta cgtctagtct caaagatggt ttaagtctgt | 600 |
| gtttctcgat tgaatgcttt gaagttctta cgataggtta agtaagctaa ggaagagagg | 660 |
| taggagggag gagtgaggtg aacgaatgat gagtacatgc ccgatcttct gagaggtaac | 720 |
| tggtaagttt gatttgtgga gatctcgacg ttggcgatcc ggcttcaaac cagacacgat | 780 |
| tcgaaccctg caaccgttac accactgatc cgttggttat caaccaagca aacttgatt | 840 |
| gacctcgcca agaaggcttt tcctgcaagc gaatcgaaga acacaagcaa gaaggtttaa | 900 |
| acatgcaatc tgaaattgca aatatgaatg acacgaatat caatagaggg ttcaagaact | 960 |
| cggtttcaaa ggactaatcg acgcagtgga ggagattaag aacgggagca ctggatcatt | 1020 |
| gtaaaaggat ttgtcaccac agttacaatg aacgattcag tttctcgatg gaaaactaaa | 1080 |
| ctctaaacaa aacccaagtc tcgacagctt gcggctgcgt ggaatataaa agagaggcgt | 1140 |

| | |
|---|---|
| cctaggattg gaaggcgacc agggatggtg cccacaactt gggcttaagg tctgactcat | 1200 |
| tacatagcca agttggctta aaatagatga cgcatcaact tatcgtagtc acacagatta | 1260 |
| atccacgtgt catctggagc tgggacaaga tccaaaacga tgacatcgtc gtccccttc | 1320 |
| caatgagtcc aagatctccc tatttcgatg tcgtatgaag aagttatgat cgaaacatta | 1380 |
| acgacgtgtc tgctgaattc gagggtgacg tgacagctga gttggagatg agttgcaact | 1440 |
| t | 1441 |

<210> SEQ ID NO 7
<211> LENGTH: 2620
<212> TYPE: DNA
<213> ORGANISM: Sorghum bicolor

<400> SEQUENCE: 7

| | |
|---|---|
| caatatgcat cggcatcttg ccgatgaggc ggctgcggat ctggcacctg atggcgaacc | 60 |
| tccacgtgtc tgttcgggac gtgatctgta cggaacattg tattgatcac ctgtcctcca | 120 |
| atctgcggac caccaaactg ctgtccaccg attggctgtc ctccgaattg ctgtccaaaa | 180 |
| ttcattggct ggttgggaat cccctgacct tggaacccgg datagacctg cccttgctgg | 240 |
| aaccctgtag tctggtaact ctgctggggc gattgtggaa aggcttgctg tccaaaccat | 300 |
| ccactattag cgttcatcgg catagatgct gccgatgatt ggtaattggg taccgtcgtt | 360 |
| gaattgacat accccgactg ggccgcagac ctctgttgta tcagcattga ctttgccgat | 420 |
| gcgttgggca tctgaacat tgaatcttga ggatttccag tgtgaggcct gcagtagtg | 480 |
| gttgtggtat accgaggact ctggttcatc ggcgcattgg gaggtgccga tgtcatagga | 540 |
| gttttgcccc tcatgtcagt tatctgtgat gttcccggtg tcacctctgg aggcataccg | 600 |
| taaccccacc agttgggagg aagagtcaac cctgacattg ccaatgccaa catatctgtt | 660 |
| gtcagtttat gctgcccaac tgaaatctgt gggttggttg ccatcggcat agatagtgca | 720 |
| ccagtagtcc ccgatgtact tggagggacg gcagattgtg cacttgcatt cgtcaaggca | 780 |
| gccgacggag ccgtgaccct ctggtgccgtt ggctgatgat gggagggggcc cacatactct | 840 |
| ggtgggattt gtccttcctt gaaagtcctt gccacggcat tgaaaaccgt attagacagt | 900 |
| acaccagctt ggttaatcaa cgctcgattg atggcattgt caaccatatc ttgaagcttg | 960 |
| ccaggattgg cgtcaaaggt aacctgccgt ggtgccggca gcgcatcttt ctgaaccact | 1020 |
| tcgccgctcc tgtttatgct gaaagacctc aggcattgct gcttgaactc ttccatggct | 1080 |
| tgggcaatag cttgcttctg ctcatccttg aggttggcct ccgtcacggg gatgacgttc | 1140 |
| tcttgatcga ggtcagagat cgacatgttg atcttgatct tgaatctgtc ccaccgggcg | 1200 |
| tgccaaaaga tgtgttgatg caaaagctga tctgcaaaca caagggcta ataccccgatt | 1260 |
| tcaacgttaa ggcgtgccag ccgatttgac cttactatcg gcaaaggtga taactcgaat | 1320 |
| actttggtcc cgacaacagc gatgcgccca gatgccacgg ccaagaggta ttcacgcgga | 1380 |
| acttgagaac acgccgagct taagtcgacg aattcctaag aactcgtaat aaaaaggaaa | 1440 |
| aagtatgaca aagtcgtcga aatagtagat gctggaatat gagtaaaaac ttgtgtttga | 1500 |
| ttgattgata gatcattaca aggccctagg gtctatattt ataccctgct caagagtta | 1560 |
| caaccagaca caattagaat tcgaattcca aattacacgg aatccgtata caaaacgatg | 1620 |
| taaataatta aggaaataac aaaactatcc cccgtgacaa actgaaactc ctccacacaa | 1680 |
| cgaccggcag cttccggact ccctctttg catcatcggc agaccctttg ccatagtcat | 1740 |
| cggcagactt tcttatctag ccatcggcac aatcacatca ctgtctgtag acttagtcac | 1800 |

-continued

```
gttcagcttc tccttcatcg gcaactatcc tcatcggcaa cccaccctgt agacagcata    1860
ctgccacctt atcctgccat cctagacaca tgcccaaaaa cggtgtcaac agtacttggt    1920
gtcttggtga ttgaatacta tcagcgaatc aggtcaacga tctactagca attaacaata    1980
tatcatttct taatcttttg ctagttccgt ttcaattaga aaactatctc taccactcat    2040
ctgcatgcta ttgttcttaa ttaattactt gatatatatg gagcatatct ctaccactct    2100
catctgcaca tgctaatata atatatagtg atttgcacga ttcacaatca ataatttgca    2160
tgataatata ctggaacacg tgaaccagag gcacttacgg ccgcgtgttt attacttaat    2220
ttgccatata agatactata tgattccttt cacagattgg cagagatatg acatgtgtta    2280
tcttattctg tgattaacta tgtatatatg cccgggattt aattttttgcc tgatccgaaa    2340 caaatgggga accactactg cgtcgcattc ctcgcataag atatattcta cagtaataaa    2400
caacgacgtc tgcccacaga acgaaatcgc tcgaagcctc aaaacgacgg acggagtaac    2460
caatgcatgc ccaagctctc tatatatatt cgcttgaacg tctctccaat cacatcacac    2520
ggcgagctag ctaggaaaca aacacacatc aacatacagc aaacattaga caagaatcaa    2580
acacgttcgc aggaaaagaa tagaagctag ggaggaggaa                         2620
```

<210> SEQ ID NO 8
<211> LENGTH: 1483
<212> TYPE: DNA
<213> ORGANISM: Sorghum bicolor

<400> SEQUENCE: 8

```
accaacatac tcgatcggtt cctatatatg ctcgatgaag gtttacgtgg tgccatatat      60
tgccgattca gtgctcctgt tcgttcgtcc ttggtgcgat gttgttgcac gtgcggtata     120
tgatctgttt agtttatttt atctactatg aggtgtgaaa aggctattat gacctatgtg     180
ttttagaaaa atatgttatg agctatgtgg tgtggaaaat aaagctcttg tgagttttgt     240
gttgtgttgt gaaaaaagct ataaactgtt tctttgtaat aaatatgaaa cctgtcccct     300 ttttatctc ctttgaaaca gctataatac aaaatgcatc tctattgcaa tgaataatcc      360
tcttcaaaga gagaggtgcc ctcaggaata caggtggtgc atggctttcg tcagctcatg     420
ccgtaaggta ttgggttaag tctcgcaacg agcgtaaccc ttgtgttgat gtctagtcca     480
gtgtagctga cattgctaaa atgcatcaac ttggtgctaa aaataggaga acatatagca     540
ttataaagac tgcttaccaa ggggtttaat ataatgtgtc caagaataaa atttacaaac     600
ctcataaatg accccggtta tggtatttgt catggcaatt gcctgttcga ggtatgcaga     660
ttttcttatg cggccagcct tgagcggtga acagtactgc gggttcgtct tcaagggaag     720
tttcatattt ggagacaata ggttggacag agacagcctg tgctttggaa ccaggctcag     780
caagttgact tgtcgccttc acttgctcaa cttgggtgat gaggacaagg ccgctataca     840
tatagccatg cttagagaat cacatgcaga ccaagtagat caacaagggg acctgaatgg     900
agaagaaggt ctaaagctta tacggtttca gtcaccggtg gaagcctaaa tcaagttcga     960
gtccacctcg gaatctagga gcagtctgta gtaaaacgga tgcccaggaa acattctgat    1020
tctgtttttg atgatccaca tatggatgaa aagataattt gataagctaa ctaatggctt    1080
tagtttcacg tcaaaattca tccgaagtca acaggaatcg tcaaaacaag ttagcatcca    1140
gaatctgcaa gggtgctgcg tcactgtttt tggtccgttg ggttgtgtat catcattgag    1200
tccattagga gaggcgtcca gagggagtga cgaccctaac accttataat cagtaaccgc    1260
```

```
caccctcatt aggatttggg ttattctatt tacaatagtt tcactatcat tggttttta     1320 gaccccaact ttgtgagatt aatcattcat ttgcaaattt agttgcattt ttttgttctt    1380
gcttgtgttc tttgatttgc aggcaaggat tagccttctt ggcgaggtcg aacgtgcagc    1440
gccggtcaat aacctgagat gacgtggtgc taaggttgca tgg                     1483
```

<210> SEQ ID NO 9
<211> LENGTH: 2053
<212> TYPE: DNA
<213> ORGANISM: Artificial Sequence
<220> FEATURE:
<223> OTHER INFORMATION: GUSPlus coding sequence

<400> SEQUENCE: 9

```
atggtagatc tgagggtaaa tttctagttt ttctccttca ttttcttggt taggacccttt     60 ttctcttttt attttttga gctttgatct ttctttaaac tgatctattt tttaattgat     120
tggttatggt gtaaatatta catagcttta actgataatc tgattacttt atttcgtgtg    180
tctatgatga tgatgatagt tacagaaccg acgaactagt ctgtacccga tcaacaccga    240
gacccgtggc gtcttcgacc tcaatggcgt ctggaacttc aagctggact acgggaaagg    300
actggaagag aagtggtacg aaagcaagct gaccgacact attagtatgg ccgtcccaag    360
cagttacaat gacattggcg tgaccaagga atccgcaac catatcggat atgtctggta    420
cgaacgtgag ttcacggtgc cggcctatct gaaggatcag cgtatcgtgc tccgcttcgg    480
ctctgcaact cacaaagcaa ttgtctatgt caatggtgag ctggtcgtgg agcacaaggg    540
cggattcctg ccattcgaag cggaaatcaa caactcgctg cgtgatggca tgaatcgcgt    600
caccgtcgcc gtggacaaca tcctcgacga tagcacccct ccggtgggc tgtacagcga    660 gcgccacgaa gagggcctcg gaaaagtcat tcgtaacaag ccgaacttcg acttcttcaa    720
ctatgcaggc ctgcaccgtc cggtgaaaat ctacacgacc ccgtttacgt acgtcgagga    780
catctcggtt gtgaccgact caatggccc aaccgggact gtgacctata cggtggactt    840
tcaaggcaaa gccgagaccg tgaaagtgtc ggtcgtggat gaggaaggca agtggtcgc    900 aagcaccgag ggcctgagcg taacgtgga gattccgaat gtcatcctct gggaaccact    960
gaacacgtat ctctaccaga tcaaagtgga actggtgaac gacggactga ccatcgatgt   1020
ctatgaagag ccgttcggcg tgcggaccgt ggaagtcaac gacggcaagt tcctcatcaa   1080
caacaaaccg ttctacttca agggctttgg caaacatgag gacactccta tcaacggccg   1140
tggctttaac gaagcgagca atgtgatgga tttcaatatc ctcaaatgga tcggcgccaa   1200
cagcttccgg accgcacact atccgtactc tgaagagttg atgcgtcttg cggatcgcga   1260
gggtctggtc gtgatcgacg agactccggc agttggcgtg cacctcaact tcatggccac   1320
cacgggactc ggcgaaggca cgagcgcgt cagtacctgg gagaagattc ggacgtttga   1380
gcaccatcaa gacgttctcc gtgaactggt gtctcgtgac aagaaccatc caagcgtcgt   1440
gatgtggagc atcgccaacg aggcggcgac tgaggaagag ggcgcgtacg agtacttcaa   1500
gccgttggtg gagctgacca aggaactcga cccacagaag cgtccggtca cgatcgtgct   1560
gtttgtgatg gctaccccgg agacggacaa agtcgccgaa ctgattgacg tcatcgcgct   1620
caatcgctat aacggatggt acttcgatgg cggtgatctc gaagcggcca agtccatct   1680 ccgccaggaa tttcacgcgt ggaacaagcg ttgcccagga agccgatca tgatcactga   1740 gtacggcgca gacaccgttg cgggctttca cgacattgat ccagtgatgt tcaccgagga   1800
atatcaagtc gagtactacc aggcgaacca cgtcgtgttc gatgagtttg agaacttcgt   1860
```

```
gggtgagcaa gcgtggaact tcgcggactt cgcgacctct cagggcgtga tgcgcgtcca   1920
aggaaacaag aagggcgtgt tcactcgtga ccgcaagccg aagctcgccg cgcacgtctt   1980
tcgcgagcgc tggaccaaca ttccagattt cggctacaag aacgctagcc atcaccatca   2040
ccatcacgtg tga                                                      2053

<210> SEQ ID NO 10
<211> LENGTH: 6213
<212> TYPE: DNA
<213> ORGANISM: Artificial Sequence
<220> FEATURE:
<223> OTHER INFORMATION: 2_23 promoter::GUSPlus::2_2-3' cassette

<400> SEQUENCE: 10
acactagaat cactctccca ctcaatcaga tgatcactat caagcataag tgagttagag     60
ggctcccaag cgccaccaca taagccacca aggccctagt gggctcagca actagccaaa    120
gggcggccac acttctattt atagccacaa gggctaaaca agccgttgcc ccttcactag    180
gcaaaacgcg ggggcgtcgg acgcaccacc ccagtgtccg tagctcatga agcagccacg    240
tgctactagt cgtttgaact taaccgttgc cgccaacggc taactcacac gtgccgaggg    300
ataggacgtt ctggcacaac ttgtcggacg ctagcacctc acgtccgacg ctgcttagag    360
agttcccaaa cttggttaca caccatcgga cgtgtctgac gggtgatcat cggacgcgtg    420
ccagcgtcct acacgtacac ctcgcaaaac gttgcgtgcg ttggacactc attagtactc    480
ggtcagcatc cgacacaaaa ccttcggaca tgccaatgca cagtgcaact ctatcacaca    540
ttgtcgaacg caggtctagc gtccaacgct gccaagtctt gctcaagctt agctgtcaca    600
cgcggtctct cgcttcaaag cctccgactt gcccttcaca catgcaatca gtccgtcaag    660
ccaagcctta tctagatctt ctccatcttg gtcacatgac tccatgtcat gtctcatatg    720
caatgagctc ctccatcatt acatattcac ctatagacta atctcctgtg tatctcacat    780
aaaaactatt agtccaccta agttattcaa ttaccaaaac caaacaagaa ccttttagcg    840
ggtaactttg acaaaaagtt tgaagacaca acagatgtca atgatgtgca tgatccggat    900
gactttggcc atgattttca gtgaggaaga gaaaggctat agaacataga taaggcatga    960
ctgtgtttgt gatcgaggga ggtagtttag taaagaattt ttggtgtata ttataaagaa   1020
agtagtgata aaaaggatag ttttttggtgt ctacactaat aaattaatca agcatgcatg   1080
gacccaacta tatatcctaa tcctaatggt ataatggtaa ataatccatt catggtccat   1140
gatccttgga tttgggtcca tggcaattca aaaactagct atctctctct ctctctctta   1200
gtctctctgc caaagatatt tgaagcacat tctgacggca ataaaaaaag acgtaaaact   1260
agcgggcgat gaactcattc accattacaa ccattaaatt taatgcaaat taagtaccgg   1320
tttaatatag aaaattatga ataacatgtt ttgtgacatc tgacatgtgc atgtgtgtac   1380
atgtttctaa ttatcatgat tttaatcata gaaaacaaag gacggtttgc aacaacatac   1440
ccaacgacac taaagctgac gctagttgcc atagaggttg tctatgtagc acaaccaagc   1500
taggatttag tgagggggtct acctagaagg cgcatccgac aaagaagacg agaaagacga   1560
tgtggtggca agggagcccc tcctcggatg gctgcatggg aaggcgctca acaacaaggat  1620 ggtggtggat ggagacgagg aaaaaggtcg agccagggaa gaagaacgga gatggtgcca   1680
gacctcgact gtgaaatcta ggaccagtgc ctccttgtgaa atcatttgtg cagcagtgtt   1740
acttttccga gctaagaagg ttggtccatg tggctcaaat taaagttgat ggataggcca   1800
```

```
gtgatcaagc aatgtagacc caaaggttgt gtccgaaatt ttcatttacg tttcaatgtg    1860
gtttctaaaa aaataatttc aatgctacac caaaacataa gaattataga gttttgtcgt    1920
ggctttgaaa cttcttccaa tcgtgctagt ttaatttgta tatcaggacc atgctattcc    1980
tctggccttg gttcttgcgc atccattcta aatgagcacg cgccacgcca cacattcctt    2040
cttaatcacc agctgcttcg ctagcttgac atccaatgtc ctgggcacca ctccgtcgga    2100
tccgccagga tgcccagctg aaatgatgcc taatgatcat atgaaaacaa atattagtat    2160
acgagctggc catttgcgga gccaaccgaa gtcgtcgtgc acaaaatatt tgataccgta    2220
tcacggaaaa cactaaatat acgatgtagg caataatcta gaacggactc ttcctcaccg    2280
gtcgggttca cctgtatata tttgaatatg atgactcggt tcatttgaac actatcgtgc    2340
ctagtagtgc accgatttct taatcctaag gctggactat aagtatccct ggtaacaccc    2400
cgtgatcaaa gcatcgcaaa ctagctgcta atcacttgtc aagagctctc tgaccatatt    2460
agctctagag tgatccgcga gctggtgtga tcgagcaata atggtagatc tgagggtaaa    2520
tttctagttt ttctccttca ttttcttggt taggacccct ttctcttttt atttttttga    2580
gctttgatct ttctttaaac tgatctattt tttaattgat tggttatggt gtaaatatta    2640
catagcttta actgataatc tgattacttt atttcgtgtg tctatgatga tgatgatagt    2700
tacagaaccg acgaactagt ctgtacccga tcaacaccga gacccgtggc gtcttcgacc    2760
tcaatggcgt ctggaacttc aagctggact acggaaaggg actggaagag aagtggtacg    2820
aaagcaagct gaccgacact attagtatgg ccgtcccaag cagttacaat gacattggcg    2880
tgaccaagga aatccgcaac catatcggat atgtctggta cgaacgtgag ttcacggtgc    2940
cggcctatct gaaggatcag cgtatcgtgc tccgcttcgg ctctgcaact cacaaagcaa    3000
ttgtctatgt caatggtgag ctggtcgtgg agcacaaggg cggattcctg ccattcgaag    3060
cggaaatcaa caactcgctg cgtgatggca tgaatcgcgt caccgtcgcc gtggacaaca    3120
tcctcgacga tagcacccctc ccggtggggc tgtacagcga gcgccacgaa gagggcctcg    3180
gaaaagtcat tcgtaacaag ccgaacttcg acttcttcaa ctatgcaggc ctgcaccgtc    3240
cggtgaaaat ctacacgacc ccgtttacgt acgtcgagga catctcggtt gtgaccgact    3300
tcaatggccc aaccgggact gtgacctata cggtggactt tcaaggcaaa gccgagaccg    3360
tgaaagtgtc ggtcgtggat gaggaaggca agtggtcgc aagcaccgag ggcctgagcg    3420
gtaacgtgga gattccgaat gtcatcctct gggaaccact gaacacgtat ctctaccaga    3480
tcaaagtgga actggtgaac gacggactga ccatcgatgt ctatgaagag ccgttcggcg    3540
tgcggaccgt ggaagtcaac gacggcaagt tcctcatcaa caacaaaccg ttctacttca    3600
agggctttgg caaacatgag gacactccta tcaacggccg tggctttaac gaagcgagca    3660
atgtgatgga tttcaatatc ctcaaatgga tcggcgccaa cagcttccgg accgcacact    3720
atccgtactc tgaagagttg atgcgtcttg cggatcgcga gggtctggtc gtgatcgacg    3780
agactccggc agttggcgtg cacctcaact tcatggccac cacgggactc ggcgaaggca    3840
gcgagcgcgt cagtacctgg gagaagattc ggacgtttga gcaccatcaa gacgttctcc    3900
gtgaactggt gtctcgtgac aagaaccatc caagcgtcgt gatgtggagc atcgccaacg    3960
aggcggcgac tgaggaagag ggcgcgtacg agtacttcaa gccgttggtg gagctgacca    4020
aggaactcga cccacagaag cgtccggtca cgatcgtgct gtttgtgatg gctaccccgg    4080
agacggacaa agtcgccgaa ctgattgacg tcatcgcgct caatcgctat aacgatggt    4140
acttcgatgg cggtgatctc gaagcggcca aagtccatct ccgccaggaa tttcacgcgt    4200
```

```
ggaacaagcg ttgcccagga aagccgatca tgatcactga gtacggcgca gacaccgttg    4260
cgggctttca cgacattgat ccagtgatgt tcaccgagga atatcaagtc gagtactacc    4320
aggcgaacca cgtcgtgttc gatgagtttg agaacttcgt gggtgagcaa gcgtggaact    4380
tcgcggactt cgcgacctct cagggcgtga tgcgcgtcca aggaaacaag aagggcgtgt    4440
tcactcgtga ccgcaagccg aagctcgccg cgcacgtctt tcgcgagcgc tggaccaaca    4500
ttccagattt cggctacaag aacgctagcc atcaccatca ccatcacgtg tgatgagcgc    4560
ctggatctca gcgccttgag acatcttgtc ttttaatttc agctcggttt taatgatgcg    4620
ttgttatttg attgcttttc cacgtagtat gatgtacgac tagtcagcat acatgcatgc    4680
acgcatggcc ggccgtgctg tcaaattgta ttttttttcat ttgttgaaaa aaagccggcg    4740
atcacttgta tgccggtgct aagttccaat caagtttggt ttgcgattta tttcacagtt    4800
tcgcatgcat gttctggtta tattctagtc gtacttgagc atatgaaaac gtactgtcta    4860
ccacgtactt attctcttga gtgtcactga aaggaatgt gtgttggtaa gctttcttga    4920
atctgacaaa ttatgtaaaa taaatattat caatatttac atcttcacgt agtttataat    4980
aaaaatatat ttaccgatct atctaatgat actaattta caccataaat actaatattt    5040
ctgtatatat atttagtcaa aatttaaaat gtttaacttc tcagaaggtg agaatgatac    5100
tatttgtcag acggtggtgc ggggtgtcgg acaaaaatca gacggtggcg cagtgcatgc    5160
ggccactagc agcggtgcgc gatccacact tcctccagcg cagcgtttgg ggcaatcggc    5220
gatggcacgc aggccctatg tcggtagtac gctgctccct tcctctagtg agcgtggatc    5280
cgacgagcgg atccagcgac aatggcagca cgtgaatggg ctcggcgggc cttgtggata    5340
ggcttggagg gcctcatcga tgcgcatgcc atttcttatt ttgttaacac agatgagcaa    5400
gtgtccgcct gcataaatct tgatttatac tggtgttgaa ggagaggcag acgtactggc    5460
tgcccgactc caaaaaccaa ttatggtcac ctaggaaaat tgctattgtg gtggtgttaa    5520
ccgataaaac atctaaagct atttttttag aagctactgc tttcacagta taatttttcac    5580 accttgaacc ctacttcttg ctttcagtta ttccaacttc caaatgggtg gaaatatagc    5640
aacatttcat aatcatttca agagagatta gattggatag gtatgagggg ctcatcctcc    5700
ttatcttttg catttagcaa tttctttttaa actttaatag ctacaaactt ataggagagg    5760
ctttacattt ccaatggcag taagagggc tcgacgccgc tcgactacgt gctagatcca    5820
cccctaatag gttttgtagt tgctttaacc aaacaactta taattttttct agagcgcata    5880 gctcacatga gcttttttcat agttatctgg tgacagttga actatacaga cccggagtta    5940
agtcgtctgc gaactaagag ccactcaact gcctcctctc ttcctcatcc atgcatgagc    6000
cactaatgca tcactcttcc gtccccatgg atgatgcaca ccgcttcgcc gcctctgtcc    6060
ctcagccatg cttgtcttgc tttgccacct gtgtcttttc tccatgtgcg ttatacatgg    6120
gcggatccat ataggatcta ctgggtgcgg ccacacccag acaaaaatac aaaatatgct    6180
atactttgca tgtttctatg gtattcgcac ccc                                6213
```

<210> SEQ ID NO 11
<211> LENGTH: 6243
<212> TYPE: DNA
<213> ORGANISM: Artificial Sequence
<220> FEATURE:
<223> OTHER INFORMATION: SfiI-2_23 promoter::GUS-plus::2_23 terminator-
      SfiI cassette

<400> SEQUENCE: 11

```
gcggcccttg aggccacact agaatcactc tcccactcaa tcagatgatc actatcaagc      60
ataagtgagt tagagggctc ccaagcgcca ccacataagc caccaaggcc ctagtgggct     120
cagcaactag ccaaagggcg gccacacttc tatttatagc cacaagggct aaacaagccg     180
ttgccccttc actaggcaaa acgcggggc gtcggacgca ccaccccagt gtccgtagct     240
catgaagcag ccacgtgcta ctagtcgttt gaacttaacc gttgccgcca acggctaact     300
cacacgtgcc gagggatagg acgttctggc acaacttgtc ggacgctagc acctcacgtc     360
cgacgctgct tagagagttc ccaaacttgg ttacacacca tcggacgtgt ctgacgggtg     420
atcatcggac gcgtgccagc gtcctacacg tacacctcgc aaaacgttgc gtgcgttgga     480
cactcattag tactcggtca gcatccgaca caaaaccttc ggacatgcca atgcacagtg     540
caactctatc acacattgtc gaacgcaggt ctagcgtcca acgctgccaa gtcttgctca     600
agcttagctg tcacacgcgg tctctcgctt caaagcctcc gacttgccct tcacacatgc     660
aatcagtccg tcaagccaag ccttatctag atcttctcca tcttggtcac atgactccat     720
gtcatgtctc atatgcaatg agctcctcca tcattacata ttcacctata gactaatctc     780
ctgtgtatct cacataaaaa ctattagtcc acctaagtta ttcaattacc aaaaccaaac     840
aagaaccttt tagcgggtaa cttttgacaaa aagtttgaag acacaacaga tgtcaatgat     900
gtgcatgatc cggatgactt tggccatgat tttcagtgag gaagagaaag gctatagaac     960
atagataagg catgactgtg tttgtgatcg agggaggtag tttagtaaag aattttttggt    1020 gtatattata aagaaagtag tgataaaaag gatagttttt ggtgtctaca ctaataaatt    1080
aatcaagcat gcatggaccc aactatatat cctaatccta atggtataat ggtaaataat    1140
ccattcatgg tccatgatcc ttggatttgg gtccatggca attcaaaaac tagctatctc    1200
tctctctctc tcttagtctc tctgccaaag atatttgaag cacattctga cggcaataaa    1260
aaaagacgta aaactagcgg gcgatgaact cattccaccat tacaaccatt aaatttaatg    1320
caaattaagt accggtttaa tatagaaaat tatgaataac atgttttgtg acatctgaca    1380
tgtgcatgtg tgtacatgtt tctaattatc atgattttaa tcatagaaaa caaggacgg    1440 tttgcaacaa cataccccaac gacactaaag ctgacgctag ttgccataga ggttgtctat    1500
gtagcacaac caagctagga tttagtgagg ggtctaccta aaggcgcat ccgacaaaga    1560 agacgagaaa gacgatgtgg tggcaaggga gcccctcctc ggatggctgc atgggaaggc    1620
gctcacaaca aggatggtgg tggatggaga cgaggaaaaa ggtcgagcca gggaagaaga    1680
acggagatgg tgccagacct cgactgtgaa atctaggacc agtgcctctt gtgaaatcat    1740
ttgtgcagca gtgttacttt tccgagctaa gaaggttggt ccatgtggct caaattaaag    1800
ttgatggata ggccagtgat caagcaatgt agacccaaag gttgtgtccg aaattttcat    1860
ttacgtttca atgtggtttc taaaaaaata atttcaatgc tacaccaaaa cataagaatt    1920 atagagttttt gtcgtggctt tgaaacttct tccaatcgtg ctagtttaat ttgtatatca    1980
ggaccatgct attcctctgg ccttggttct tgcgcatcca ttctaaatga gcacgcgcca    2040
cgccacacat tccttcttaa tcaccagctg cttcgctagc ttgacatcca atgtcctggg    2100
caccactccg tcggatccgc caggatgccc agctgaaatg atgcctaatg atcatatgaa    2160
aacaaatatt agtatacgag ctggccattt gcggagccaa ccgaagtcgt cgtgcacaaa    2220
atatttgata ccgtatcacg gaaaacacta aatatacgat gtaggcaata atctagaacg    2280
gactcttcct caccggtcgg gttcacctgt atatatttga atatgatgac tcggttcatt    2340
```

```
tgaacactat cgtgcctagt agtgcaccga tttcttaatc ctaaggctgg actataagta   2400
tccctggtaa cacccgtga tcaaagcatc gcaaactagc tgctaatcac ttgtcaagag   2460
ctctctgacc atattagctc tagagtgatc cgcgagctgg tgtgatcgag caataatggt   2520
agatctgagg gtaaatttct agttttctc cttcattttc ttggttagga ccttttctc    2580 tttttatttt tttgagcttt gatctttctt taaactgatc tattttttaa ttgattggtt   2640
atggtgtaaa tattacatag ctttaactga taatctgatt actttatttc gtgtgtctat   2700
gatgatgatg atagttacag aaccgacgaa ctagtctgta cccgatcaac accgagaccc   2760
gtggcgtctt cgacctcaat ggcgtctgga acttcaagct ggactacggg aaaggactgg   2820
aagagaagtg gtacgaaagc aagctgaccg acactattag tatggccgtc ccaagcagtt   2880
acaatgacat tggcgtgacc aaggaaatcc gcaaccatat cggatatgtc tggtacgaac   2940
gtgagttcac ggtgccggcc tatctgaagg atcagcgtat cgtgctccgc ttcggctctg   3000
caactcacaa agcaattgtc tatgtcaatg gtgagctggt cgtggagcac aagggcggat   3060
tcctgccatt cgaagcggaa atcaacaact cgctgcgtga tggcatgaat cgcgtcaccg   3120
tcgccgtgga caacatcctc gacgatagca ccctcccggt ggggctgtac agcgagcgcc   3180
acgaagaggg cctcggaaaa gtcattcgta caagccgaa cttcgacttc ttcaactatg    3240
caggcctgca ccgtccggtg aaaatctaca cgaccccgtt tacgtacgtc gaggacatct   3300
cggttgtgac cgacttcaat ggcccaaccg ggactgtgac ctatacggtg gactttcaag   3360
gcaaagccga gaccgtgaaa gtgtcggtcg tggatgagga aggcaaagtg gtcgcaagca   3420
ccgagggcct gagcggtaac gtggagattc gaatgtcat cctctgggaa ccactgaaca    3480
cgtatctcta ccagatcaaa gtggaactgg tgaacgacgg actgaccatc gatgtctatg   3540
aagagccgtt cggcgtgcgg accgtggaag tcaacgacgg caagttcctc atcaacaaca   3600
aaccgttcta cttcaagggc tttggcaaac atgaggacac tcctatcaac ggccgtggct   3660
ttaacgaagc gagcaatgtg atggatttca atatcctcaa atggatcggc ccaacagct    3720 tccggaccgc acactatccg tactctgaag agttgatgcg tcttgcggat cgcgagggtc   3780
tggtcgtgat cgacgagact ccggcagttg gcgtgcacct caacttcatg gccaccacgg   3840
gactcggcga aggcagcgag cgcgtcagta cctgggagaa gattcggacg tttgagcacc   3900
atcaagacgt tctccgtgaa ctggtgtctc gtgacaagaa ccatccaagc gtcgtgatgt   3960
ggagcatcgc caacgaggcg gcgactgagg aagagggcgc gtacgagtac ttcaagccgt   4020
tggtggagct gaccaaggaa ctcgacccac agaagcgtcc ggtcacgatc gtgctgtttg   4080
tgatggctac cccggagacg gacaaagtcg ccgaactgat tgacgtcatc gcgctcaatc   4140
gctataacgg atggtacttc gatggcggtg atctcgaagc ggccaaagtc catctccgcc   4200
aggaatttca cgcgtggaac aagcgttgcc caggaaagcc gatcatgatc actgagtacg   4260
gcgcagacac cgttgcgggc tttcacgaca ttgatccagt gatgttcacc gaggaatatc   4320
aagtcgagta ctaccaggcg aaccacgtcg tgttcgatga gtttgagaac ttcgtgggtg   4380
agcaagcgtg gaacttcgcg gacttcgcga cctctcaggg cgtgatgcgc gtccaaggaa   4440
acaagaaggg cgtgttcact cgtgaccgca agccgaagct cgccgcgcac gtctttcgcg   4500
agcgctggac caacattcca gatttcggct acaagaacgc tagccatcac catcaccatc   4560
acgtgtgatg agcgcctgga tctcagcgcc ttgagacatc ttgtctttta atttcagctc   4620
ggttttaatg atgcgttgtt atttgattgc ttttccacgt agtatgatgt acgactagtc   4680
agcatacatg catgcacgca tggccggccg tgctgtcaaa ttgtattttt ttcatttgtt   4740
```

```
gaaaaaaagc cggcgatcac ttgtatgccg gtgctaagtt ccaatcaagt ttggtttgcg    4800
atttatttca cagtttcgca tgcatgttct ggttatattc tagtcgtact tgagcatatg    4860
aaaacgtact gtctaccacg tacttattct cttgagtgtc actgagaagg aatgtgtgtt    4920
ggtaagcttt cttgaatctg acaaattatg taaaataaat attatcaata tttacatctt    4980
cacgtagttt ataataaaaa tatatttacc gatctatcta atgatactaa ttttacacca    5040
taaatactaa tatttctgta tatatattta gtcaaaattt aaaatgttta acttctcaga    5100
aggtgagaat gatactattt gtcagacggt ggtgcggggt gtcggacaaa atcagacgg     5160 tggcgcagtg catgcggcca ctagcagcgg tgcgcgatcc acacttcctc cagcgcagcg    5220 tttgggcaa tcggcgatgg cacgcaggcc ctatgtcggt agtacgctgc tcccttcctc     5280
tagtgagcgt ggatccgacg agcggatcca gcgacaatgg cagcacgtga atgggctcgg    5340
cgggccttgt ggataggctt ggagggcctc atcgatgcgc atgccatttc ttattttgtt    5400
aacacagatg agcaagtgtc cgcctgcata aatcttgatt tatactggtg ttgaaggaga    5460
ggcagacgta ctggctgccc gactccaaaa accaattatg gtcacctagg aaaattgcta    5520
ttgtggtggt gttaaccgat aaaacatcta aagctatttt tttagaagct actgctttca    5580
cagtataatt ttcacacctt gaaccctact tcttgctttc agttattcca acttccaaat    5640
gggtggaaat atagcaacat tcataatca tttcaagaga gattagattg gataggtatg     5700
aggggctcat cctccttatc ttttgcattt agcaatttct tttaaacttt aatagctaca    5760
aacttatagg agaggcttta catttccaat ggcagtaaga ggggctcgac gccgctcgac    5820
tacgtgctag atccacccct aataggtttt gtagttgctt taaccaaaca acttataatt    5880
tttctagagc gcatagctca catgagcttt ttcatagtta tctggtgaca gttgaactat    5940
acagacccgg agttaagtcg tctgcgaact aagagccact caactgcctc ctctcttcct    6000
catccatgca tgagccacta atgcatcact cttccgtccc catggatgat gcacaccgct    6060
tcgccgcctc tgtccctcag ccatgcttgt cttgctttgc cacctgtgtc ttttctccat    6120
gtgcgttata catgggcgga tccatatagg atctactggg tgcggccaca cccagacaaa    6180
aatacaaaat atgctatact ttgcatgttt ctatggtatt cgcaccccgg ccgccatggc    6240
cgc                                                                  6243
```

<210> SEQ ID NO 12
<211> LENGTH: 2513
<212> TYPE: DNA
<213> ORGANISM: Artificial Sequence
<220> FEATURE:
<223> OTHER INFORMATION: SfiI-2_23 promoter

<400> SEQUENCE: 12

```
ggcccttaag gccacactag aatcactctc ccactcaatc agatgatcac tatcaagcat      60
aagtgagtta gagggctccc aagcgccacc acataagcca ccaaggccct agtgggctca     120
gcaactagcc aaagggcggc cacacttcta tttatagcca caagggctaa acaagccgtt     180
gccccttcac taggcaaaac gcgggggcgt cggacgcacc accccagtgt ccgtagctca     240
tgaagcagcc acgtgctact agtcgtttga acttaaccgt tgccgccaac ggctaactca     300
cacgtgccga gggataggac gttctggcac aacttgtcgg acgctagcac ctcacgtccg     360
acgctgctta gagagttccc aaacttggtt acacaccatc ggacgtgtct gacgggtgat     420
catcggacgc gtgccagcgt cctacacgta cacctcgcaa aacgttgcgt gcgttggaca     480
```

```
ctcattagta ctcggtcagc atccgacaca aaaccttcgg acatgccaat gcacagtgca      540
actctatcac acattgtcga acgcaggtct agcgtccaac gctgccaagt cttgctcaag      600
cttagctgtc acacgcggtc tctcgcttca agcctccga cttgcccttc acacatgcaa       660
tcagtccgtc aagccaagcc ttatctagat cttctccatc ttggtcacat gactccatgt      720
catgtctcat atgcaatgag ctcctccatc attacatatt cacctataga ctaatctcct      780
gtgtatctca cataaaaact attagtccac ctaagttatt caattaccaa aaccaaacaa      840
gaacctttta gcgggtaact ttgacaaaaa gtttgaagac acaacagatg tcaatgatgt      900
gcatgatccg gatgactttg ccatgattt tcagtgagga agagaaaggc tatagaacat       960
agataaggca tgactgtgtt tgtgatcgag ggaggtagtt tagtaaagaa ttttggtgt      1020 atattataaa gaaagtagtg ataaaaagga tagttttggt tgtctacact aataaaattaa    1080 tcaagcatgc atggacccaa ctatatatcc taatcctaat ggtataatgg taaataatcc     1140
attcatggtc catgatcctt ggatttgggt ccatggcaat tcaaaaacta gctatctctc     1200
tctctctctc ttagtctctc tgccaaagat atttgaagca cattctgacg gcaataaaaa    1260
aagacgtaaa actagcgggc gatgaactca ttcaccatta caaccattaa atttaatgca    1320
aattaagtac cggtttaata tagaaaatta tgaataacat gttttgtgac atctgacatg    1380
tgcatgtgtg tacatgtttc taattatcat gattttaatc atagaaaaca aaggacggtt    1440
tgcaacaaca tacccaacga cactaaagct gacgctagtt gccatagagg ttgtctatgt    1500
agcacaacca agctaggatt tagtgagggg tctacctaga aggcgcatcc gacaaagaag    1560 acgaaaaga cgatgtggtg gcaagggagc ccctcctcgg atggctgcat gggaaggcgc     1620
tcacaacaag gatggtggtg gatggagacg aggaaaaagg tcgagccagg gaagaagaac   1680
ggagatggtg ccagacctcg actgtgaaat ctaggaccag tgcctcttgt gaaatcattt   1740
gtgcagcagt gttacttttc cgagctaaga aggttggtcc atgtggctca aattaaagtt   1800
gatggatagg ccagtgatca agcaatgtag acccaaaggt tgtgtccgaa attttcattt   1860
acgtttcaat gtggtttcta aaaaaataat ttcaatgcta caccaaaaca taagaattat   1920
agagttttgt cgtggctttg aaacttcttc caatcgtgct agtttaattt gtatatcagg   1980
accatgctat tcctctggcc ttggttcttg cgcatccatt ctaaatgagc acgcgccacg   2040
ccacacattc cttcttaatc accagctgct tcgctagctt gacatccaat gtcctgggca   2100
ccactccgtc ggatccgcca ggatgcccag ctgaaatgat gcctaatgat catatgaaaa   2160
caaatattag tatacgagct ggccatttgc ggagccaacc gaagtcgtcg tgcacaaaat   2220
atttgatacc gtatcacgga aaacactaaa tatacgatgt aggcaataat ctagaacgga   2280
ctcttcctca ccggtcgggt tcacctgtat atatttgaat atgatgactc ggttcatttg   2340
aacactatcg tgcctagtag tgcaccgatt tcttaatcct aaggctggac tataagtatc   2400
cctggtaaca ccccgtgatc aaagcatcgc aaactagctg ctaatcactt gtcaagagct   2460
ctctgaccat attagctcta gagtgatccg cgagctggtg tgatcgagca ata         2513
```

<210> SEQ ID NO 13
<211> LENGTH: 1673
<212> TYPE: DNA
<213> ORGANISM: Artificial Sequence
<220> FEATURE:
<223> OTHER INFORMATION: 2_23 terminator- SfiI)

<400> SEQUENCE: 13

```
tgagcgcctg gatctcagcg ccttgagaca tcttgtcttt taatttcagc tcggttttaa       60
```

```
tgatgcgttg ttatttgatt gcttttccac gtagtatgat gtacgactag tcagcataca      120
tgcatgcacg catggccggc cgtgctgtca aattgtattt ttttcatttg ttgaaaaaaa      180
gccggcgatc acttgtatgc cggtgctaag ttccaatcaa gtttggtttg cgatttattt      240
cacagtttcg catgcatgtt ctggttatat tctagtcgta cttgagcata tgaaaacgta      300
ctgtctacca cgtacttatt ctcttgagtg tcactgagaa ggaatgtgtg ttggtaagct      360
ttcttgaatc tgacaaatta tgtaaaataa atattatcaa tatttacatc ttcacgtagt      420
ttataataaa aatatattta ccgatctatc taatgatact aattttacac cataaatact      480
aatatttctg tatatatatt tagtcaaaat ttaaaatgtt taacttctca gaaggtgaga      540
atgatactat ttgtcagacg gtggtgcggg gtgtcggaca aaaatcagac ggtggcgcag      600
tgcatgcggc cactagcagc ggtgcgcgat ccacacttcc tccagcgcag cgtttggggc      660
aatcggcgat ggcacgcagg ccctatgtcg gtagtacgct gctcccttcc tctagtgagc      720
gtggatccga cgagcggatc cagcgacaat ggcagcacgt gaatgggctc ggcgggcctt      780
gtggataggc ttggagggcc tcatcgatgc gcatgccatt tcttattttg ttaacacaga      840
tgagcaagtg tccgcctgca taaatcttga tttatactgg tgttgaagga gaggcagacg      900
tactggctgc ccgactccaa aaccaatta tggtcaccta ggaaaattgc tattgtggtg       960
gtgttaaccg ataaaacatc taaagctatt ttttagaag ctactgcttt cacagtataa      1020
ttttcacacc ttgaacccta cttcttgctt tcagttattc aacttccaa atgggtggaa      1080 atatagcaac atttcataat catttcaaga gagattagat tggataggta tgaggggctc      1140
atcctcctta tcttttgcat ttagcaattt cttttaaact ttaatagcta caaacttata      1200
ggagaggctt tacatttcca atggcagtaa gagggggctcg acgccgctcg actacgtgct      1260
agatccaccc ctaataggtt ttgtagttgc tttaaccaaa caacttataa tttttctaga      1320
gcgcatagct cacatgagct ttttcatagt tatctggtga cagttgaact atacagaccc      1380
ggagttaagt cgtctgcgaa ctaagagcca ctcaactgcc tcctctcttc ctcatccatg      1440
catgagccac taatgcatca ctcttccgtc cccatggatg atgcacaccg cttcgccgcc      1500
tctgtccctc agccatgctt gtcttgcttt gccacctgtg tcttttctcc atgtgcgtta      1560
tacatgggcg gatccatata ggatctactg ggtgcggcca cacccagaca aaaatacaaa      1620
atatgctata ctttgcatgt ttctatggta ttcgcacccc ggccgccatg gcc            1673
```

<210> SEQ ID NO 14
<211> LENGTH: 5497
<212> TYPE: DNA
<213> ORGANISM: Artificial Sequence
<220> FEATURE:
<223> OTHER INFORMATION: 2_32 promoter::GUSPlus::2_32-3' cassette

<400> SEQUENCE: 14

```
ttagctagat cggatggtta agaacctagt aagaggaact taagttgtag gctagaacca       60
aaatttagta gacctagagc cagctctagt taaattgtaa gggtgcgcat aactccataa      120
tccataattc tagccaccca ttgtgtcgcc gacccagagt cccagactag gaatcgacgc      180
ggacaggcag gcagccctct ccgactccgt gggcaccgtc gtcgcagcta ctcgttgctc      240
cgtctacgaa agaatcaatt tttaaagttg ttctaagtca aactttttaa actttaacca      300
aatttctaga aaaaaatact aagatttatg gtatcaaatt agtatcatta gattcactat      360
agaatatatt ttcatatgat acgtatttta tatcatagat ttgttaccat tttctataaa      420
```

```
attagtcaaa cttaaaaaag tttgacggat acggattcta agaattgatt cttttatgga    480
cagagggagt acatacagca ggctgtgtct gtgcaaacgt ccggcttcta cgacgggcgg    540
ccaggttgag gtcttgttta gatccaaaaa gttttggat tttaacactc actttcattt    600
ttatttgaca acattgtcc aatcatagag taactagact taaaagattc gtctcgcaat    660
ttacagacaa attgtgcaat tagttttttt tatcatattt aatgctctat gaatatacca    720
taagattcga tgtgataaaa aatcttaaaa aaattgtttt tttagtaaac taaacaatgc    780
cgtgccgtgg gcgtgggcgt ggagaacatg caatgcattg catgggaac atcgatgaac    840
caaagttaat gggcacacta aactgcatgc cccagacaca gttttaaaat ttatttacta    900
atatagcaac aaaaaaaac aaatatatgc acgcccgcac gcacgtcctg tgcatatata    960
tatgcacgga cgctattcaa atcaacaggg agaggacagt ttggtcggtg gagtatctat   1020
ctacactaaa aaataccgcc ctcctctact cagctcgtcc ccgattttt taactcctcc   1080
tccaaatcac aatcagatat caaatcaaat caaatcattc taaatcgaaa aaaaagaaa   1140
atattaaatc aaatcaagaa aaaatataag tcaaatacac agaatatccc atcatgctca   1200
tcttgtcctt ggatattttg actctctcct ccaaatcaga atcggatatc aaatcaaatc   1260
aaatcgttct aaaaccgaat aaaaaaaaga aaatatcaaa ccaaatgaaa tgaaatcgag   1320
aaaaaaaaaa tcaaatatgc agggtatcgt agtaccatcc tactctgttc agctcatccc   1380
caaattttt ttgccttgct cctcgaaatc agaatcgaat atcaaatcat tctaaatcca   1440
aatcagaaaa agaaatatca aaccaaatta aatgaaatca taaaaaaata taagtcaaat   1500
atgcaaagta tcattttgac tcgctcctcc aaatgagatc gaatatcaaa atcgaatcaa   1560
attgtttgaa atctgaattt taaaaaataa aatatcaaac caaatcaaat gaaatcggaa   1620
aaaaatacaa gtaaaataca cagggtattg tcgtaccacc ctgctttact caacttgtcc   1680
ttggattttt ttgcatgtct cctccaaatc agaatcggat atcaaatcat atcgttccaa   1740
atccgaattg gaaagaagaa aatatcaaac caaatcaaat gaaatagaaa aaaaatacaa   1800
gttagtgtgt tgttgcaact gtattgaaac ttgacctctt gccgcctgcg cgagggctcg   1860
tgaactagca ggctgtcact gtaaaaataa tagtatcagg tacaataaca gtgtgattcg   1920
actgttatat cattcatata cacgtaaaag cggagagaga aagcaatgct tttgttgatg   1980
agcttgtgac gcatgtcaag acgctttttc taagcagagg ttaactcttc ccatcctatc   2040
cttgtatatt gaataagaaa acaatattta gactatagaa agggactaat tgttgtatgt   2100
gctagactct aaataaactt gtctaataat gacttggctt ggcttataga taaattttat   2160
taggcttgct ctaaaacctg ccctcacaca tgatccgaaa cttgtggggc aataaaaagc   2220
gaaactattc tgtatattaa gctcgtgctt tgtgctacct gaaaaaaaat acaaacaggt   2280
aagccattgc gtaacaaaaa aaaatgaaa agaacaaaga aacaattaag aaatccgcct   2340
acctgatcgt gcattgtgct cggttactaa tgtactttt aaaaattgga atggatggat   2400
ggtttcctc tgactggctg gctggctgcc tgctgcttat aggagtacta tataagtaga   2460
cgcatgcagt acccaaacga cgacgccgcc accaccgcaa aagcagcaaa accttagctt   2520
gttcaccacc acaaccgcca gccatggtag atctgagggt aaatttctag ttttctcct   2580
tcattttctt ggttaggacc ctttttctctt tttatttttt tgagctttga tctttcttta   2640
aactgatcta tttttaatt gattggttat ggtgtaaata ttacatagct ttaactgata   2700
atctgattac tttatttcgt gtgtctatga tgatgatgat agttacagaa ccgacgaact   2760
agtctgtacc cgatcaacac cgagacccgt ggcgtcttcg acctcaatgg cgtctggaac   2820
```

```
ttcaagctgg actacgggaa aggactggaa gagaagtggt acgaaagcaa gctgaccgac    2880
actattagta tggccgtccc aagcagttac aatgacattg gcgtgaccaa ggaaatccgc    2940
aaccatatcg gatatgtctg gtacgaacgt gagttcacgg tgccggccta tctgaaggat    3000
cagcgtatcg tgctccgctt cggctctgca actcacaaag caattgtcta tgtcaatggt    3060
gagctggtcg tggagcacaa gggcggattc ctgccattcg aagcggaaat caacaactcg    3120
ctgcgtgatg gcatgaatcg cgtcaccgtc gccgtggaca acatcctcga cgatagcacc    3180
ctcccggtgg ggctgtacag cgagcgccac gaagagggcc tcggaaaagt cattcgtaac    3240
aagccgaact tcgacttctt caactatgca ggcctgcacc gtccggtgaa aatctacacg    3300
accccgttta cgtacgtcga ggacatctcg gttgtgaccg acttcaatgg cccaaccggg    3360
actgtgacct atacggtgga ctttcaaggc aaagccgaga ccgtgaaagt gtcggtcgtg    3420
gatgaggaag gcaaagtggt cgcaagcacc gagggcctga gcggtaacgt ggagattccg    3480
aatgtcatcc tctgggaacc actgaacacg tatctctacc agatcaaagt ggaactggtg    3540
aacgacggac tgaccatcga tgtctatgaa gagccgttcg gcgtgcggac cgtggaagtc    3600
aacgacggca gttcctcat caacaacaaa ccgttctact tcaagggctt tggcaaacat    3660
gaggacactc ctatcaacgg ccgtggcttt aacgaagcga gcaatgtgat ggatttcaat    3720
atcctcaaat ggatcggcgc caacagcttc cggaccgcac actatccgta ctctgaagag    3780
ttgatgcgtc ttgcggatcg cgagggtctg gtcgtgatcg acgagactcc ggcagttggc    3840
gtgcacctca acttcatggc caccacggga ctcggcgaag gcagcgagcg cgtcagtacc    3900
tgggagaaga ttcggacgtt tgagcaccat caagacgttc tccgtgaact ggtgtctcgt    3960
gacaagaacc atccaagcgt cgtgatgtgg agcatcgcca acgaggcggc gactgaggaa    4020
gagggcgcgt acgagtactt caagccgttg gtggagctga ccaaggaact cgacccacag    4080
aagcgtccgg tcacgatcgt gctgtttgtg atggctaccc cggagacgga caaagtcgcc    4140
gaactgattg acgtcatcgc gctcaatcgc tataacggat ggtacttcga tggcggtgat    4200
ctcgaagcgg ccaaagtcca tctccgccag gaatttcacg cgtggaacaa gcgttgccca    4260
ggaaagccga tcatgatcac tgagtacggc gcagacaccg ttgcgggctt tcacgacatt    4320
gatccagtga tgttcaccga ggaatatcaa gtcgagtact accaggcgaa ccacgtcgtg    4380
ttcgatgagt ttgagaactt cgtggtgag caagcgtgga acttcgcgga cttcgcgacc    4440
tctcagggcg tgatgcgcgt ccaaggaaac aagaagggcg tgttcactcg tgaccgcaag    4500
ccgaagctcg ccgcgcacgt cttttcgcgag cgctggacca acattccaga tttcggctac    4560
aagaacgcta gccatcacca tcaccatcac gtgtgacttg catcattgct gggagggatc    4620
cattccatgc ctgcgctttg ccagctggga ataatgatag atgcccgtac gtacgtctcg    4680
atatgcatac ggttgatgtt ggtgttgaat acctcgcgct ctcgtattcg tatacggagt    4740
agtaggtgaa gtcagttggt gcaatgtatt ccatctgttc gtggcctata tattatgcaa    4800
aaaaataatg tcagaataat taaatcacat gtgtgagatt gaataaataa ccaatttctc    4860
cgcatcgttt atatattaat tgtacagtat atatagtagg atcaggagta atgcatgctt    4920
agctactcta tatacctctc aaaaacgatt gtgtactata aattcataat aggcgaagga    4980
cctgctgtat aaacgctgct ggggttaccg gccgggcata tacatatcct cctttcttat    5040
cagcaaggcc tgctgtacta aattcataat aaggaccca gcagcgtttc gatcgtcgac    5100
atacatatct cctacctaca gcttcttcga cggacaaaac ttggtgtctt gctgtggatt    5160
```

```
tataatgggc ttggcccata tacatttagt aaatcaataa actcggtgta taattaatac    5220
aatacgggat atattgataa aacattaact agacttatat ggttggattt tatccttcta    5280
tattgagaag ttgagaaaag tacaaaggcg tgccacacgt gcgcgcactg ccgccgccca    5340
ggccgtgccg ccaatcaaaa ctcataataa cgtgagtttc ttcttttgta ttatcacgat    5400
taatctttgt ctgttacgaa ctctttgctt gtttgtctgt ctcttgagtt gactgcgatc    5460
ccttctcctg cctctacctg cgagaataaa atctcga                             5497
```

<210> SEQ ID NO 15
<211> LENGTH: 5512
<212> TYPE: DNA
<213> ORGANISM: Artificial Sequence
<220> FEATURE:
<223> OTHER INFORMATION: HindIII-2_32 promoter::GUS-plus::2_32
      terminator- EcoRI cassette

<400> SEQUENCE: 15

```
cgcaagctta gctagatcgg atggttaaga acctagtaag aggaacttaa gttgtaggct      60
agaaccaaaa tttagtagac ctagagccag ctctagttaa attgtaaggg tgcgcataac     120
tccataatcc ataattctag ccacccattg tgtcgccgac ccagagtccc agactaggaa     180
tcgacgcgga caggcaggca gccctctccg actccgtggg caccgtcgtc gcagctactc     240
gttgctccgt ctacgaaaga atcattttt aaagttgttc taagtcaaac tttttaaact      300
ttaaccaaat ttctagaaaa aaatactaag atttatggta tcaaattagt atcattagat     360
tcactataga atatattttc atatgatacg tattttatat catagatttg ttaccatttt     420
ctataaaatt agtcaaactt aaaaaagttt gacggatacg gattctaaga attgattctt     480
ttatggacag agggagtaca tacagcaggc tgtgtctgtg caaacgtccg gcttctacga     540
cgggcggcca ggttgaggtc ttgtttagat ccaaaaagtt tttggatttt aacactcact     600
ttcattttta tttgacaaac attgtccaat catagagtaa ctagacttaa aagattcgtc     660
tcgcaattta cagacaaatt gtgcaattag tttttttttat catatttaat gctctatgaa    720
tataccataa gattcgatgt gataaaaaat cttaaaaaaa ttgttttttt agtaaactaa     780
acaatgccgt gccgtgggcg tgggcgtgga gaacatgcaa tgcattgcat ggggaacatc     840
gatgaaccaa agttaatggg cacactaaac tgcatgcccc agacacagtt ttaaaattta     900
tttactaata tagcaacaaa aaaaaacaaa tatatgcacg cccgcacgca cgtcctgtgc     960
atatatatat gcacggacgc tattcaaatc aacagggaga ggacagtttg gtcggtggag    1020
tatctatcta cactaaaaaa taccgccctc ctctactcag ctcgtcccg atttttttaa     1080 ctcctcctcc aaatcacaat cagatatcaa atcaaatcaa atcattctaa atcgaaaaaa    1140
aaagaaaata ttaaatcaaa tcaagaaaaa atataagtca aatacacaga atatcccatc    1200
atgctcatct tgtccttgga tattttgact ctctcctcca aatcagaatc ggatatcaaa    1260
tcaaatcaaa tcgttctaaa accgaataaa aaaagaaaa tatcaaacca atgaaatga     1320 aatcgagaaa aaaaaaatca atatgcaggg gtatcgtagt accatcctac tctgttcagc    1380
tcatccccaa attttttttg ccttgctcct cgaaatcaga atcgaatatc aaatcattct    1440
aaatccaaat cagaaaaaga aatatcaaac caattaaat gaaatcataa aaaatataa      1500 gtcaaatatg caagtatca ttttgactcg ctcctccaaa tgagatcgaa tatcaaaatc     1560
gaatcaaatt gtttgaaatc tgaattttaa aaaataaaat atcaaaccaa atcaaatgaa    1620
atcggaaaaa aatacaagta aaatacacag ggtattgtcg taccaccctg ctttactcaa    1680
```

```
cttgtccttg gattttttg catgtctcct ccaaatcaga atcggatatc aaatcatatc    1740
gttccaaatc cgaattggaa agaagaaaat atcaaaccaa atcaaatgaa atagaaaaaa    1800
aatacaagtt agtgtgttgt tgcaactgta ttgaaacttg acctcttgcc gcctgcgcga    1860
gggctcgtga actagcaggc tgtcactgta aaaataatag tatcaggtac aataacagtg    1920
tgattcgact gttatatcat tcatatacac gtaaaagcgg agagagaaag caatgctttt    1980
gttgatgagc ttgtgacgca tgtcaagacg cttttttctaa gcagaggtta actcttccca    2040
tcctatcctt gtatattgaa taagaaaaca atatttagac tatagaaagg gactaattgt    2100
tgtatgtgct agactctaaa taaacttgtc taataatgac ttggcttggc ttatagataa    2160
attttattag gcttgctcta aaacctgccc tcacacatga tccgaaactt gtggggcaat    2220
aaaaagcgaa actattctgt atattaagct cgtgctttgt gctacctgaa aaaaaataca    2280
aacaggtaag ccattgcgta acaaaaaaaa aatgaaaaga acaaagaaac aattaagaaa    2340
tccgcctacc tgatcgtgca ttgtgctcgg ttactaatgt acttttaaa aattggaatg    2400 gatggatggt tttcctctga ctggctggct ggctgcctgc tgcttatagg agtactatat    2460
aagtagacgc atgcagtacc caaacgacga cgccgccacc accgcaaaag cagcaaaacc    2520
ttagcttgtt caccaccaca accgccagcc atggtagatc tgagggtaaa tttctagttt    2580
ttctccttca ttttcttggt taggacccctt ttctctttt atttttttga gctttgatct    2640
ttctttaaac tgatctattt tttaattgat tggttatggt gtaaatatta catagcttta    2700
actgataatc tgattacttt atttcgtgtg tctatgatga tgatgatagt tacagaaccg    2760
acgaactagt ctgtacccga tcaacaccga gacccgtggc gtcttcgacc tcaatggcgt    2820
ctggaacttc aagctggact acgggaaagg actggaagag aagtggtacg aaagcaagct    2880
gaccgacact attagtatgg ccgtcccaag cagttacaat gacattggcg tgaccaagga    2940
aatccgcaac catatcggat atgtctggta cgaacgtgag ttcacggtgc cggcctatct    3000
gaaggatcag cgtatcgtgc tccgcttcgg ctctgcaact cacaaagcaa ttgtctatgt    3060
caatggtgag ctggtcgtgg agcacaaggg cggattcctg ccattcgaag cggaaatcaa    3120
caactcgctg cgtgatggca tgaatcgcgt caccgtcgcc gtggacaaca tcctcgacga    3180 tagcacccte ccggtggggc tgtacagcga gcgccacgaa gagggcctcg aaaagtcat    3240 tcgtaacaag ccgaacttcg acttcttcaa ctatgcaggc ctgcaccgtc cggtgaaaat    3300
ctacacgacc ccgtttacgt acgtcgagga catctcggtt gtgaccgact tcaatggccc    3360
aaccgggact gtgacctata cggtggactt tcaaggcaaa gccgagaccg tgaaagtgtc    3420
ggtcgtggat gaggaaggca agtggtcgc aagcaccgag ggcctgagcg gtaacgtgga    3480
gattccgaat gtcatcctct gggaaccact gaacacgtat ctctaccaga tcaaagtgga    3540
actggtgaac gacggactga ccatcgatgt ctatgaagag ccgttcggcg tgcggaccgt    3600
ggaagtcaac gacggcaagt tcctcatcaa caacaaaccg ttctacttca agggctttgg    3660
caaacatgag gacactccta tcaacggccg tggctttaac gaagcgagca atgtgatgga    3720
tttcaatatc ctcaaatgga tcggcgccaa cagcttccgg accgcacact atccgtactc    3780
tgaagagttg atgcgtcttg cggatcgcga gggtctggtc gtgatcgacg agactccggc    3840
agttggcgtg cacctcaact tcatggccac cacgggactc ggcgaaggca gcgagcgcgt    3900
cagtacctgg gagaagattc ggacgtttga gcaccatcaa gacgttctcc gtgaactggt    3960
gtctcgtgac aagaaccatc caagcgtcgt gatgtgagc atcgccaacg aggcggcgac    4020
tgaggaagag ggcgcgtacg agtacttcaa gccgttggtg gagctgacca aggaactcga    4080
```

```
cccacagaag cgtccggtca cgatcgtgct gtttgtgatg gctaccccgg agacggacaa    4140
agtcgccgaa ctgattgacg tcatcgcgct caatcgctat aacggatggt acttcgatgg    4200
cggtgatctc gaagcggcca aagtccatct ccgccaggaa tttcacgcgt ggaacaagcg    4260
ttgcccagga aagccgatca tgatcactga gtacggcgca gacaccgttg cgggctttca    4320
cgacattgat ccagtgatgt tcaccgagga atatcaagtc gagtactacc aggcgaacca    4380
cgtcgtgttc gatgagtttg agaacttcgt gggtgagcaa gcgtggaact cgcggactt     4440 cgcgacctct cagggcgtga tgcgcgtcca aggaaacaag aagggcgtgt tcactcgtga    4500
ccgcaagccg aagctcgccg cgcacgtctt tcgcgagcgc tggaccaaca ttccagattt    4560
cggctacaag aacgctagcc atcaccatca ccatcacgtg tgacttgcat cattgctggg    4620
agggatccat tccatgcctg cgcttttgcca gctgggaata atgatagatg cccgtacgta    4680
cgtctcgata tgcatacggt tgatgttggt gttgaatacc tcgcgctctc gtattcgtat    4740
acggagtagt aggtgaagtc agttggtgca atgtattcca tctgttcgtg gcctatatat    4800
tatgcaaaaa aataatgtca gaataattaa atcacatgtg tgagattgaa taaataacca    4860
atttctccgc atcgtttata tattaattgt acagtatata tagtaggatc aggagtaatg    4920
catgcttagc tactctatat acctctcaaa acgattgtg tactataaat tcataatagg      4980
cgaaggacct gctgtataaa cgctgctggg gttaccggcc gggcatatac atatcctcct    5040
ttcttatcag caaggcctgc tgtactaaat tcataataag gaccccagca gcgtttcgat    5100
cgtcgacata catatctcct acctacagct tcttcgacgg acaaaacttg gtgtcttgct    5160
gtggatttat aatgggcttg gcccatatac atttagtaaa tcaataaact cggtgtataa    5220
ttaatacaat acgggatata ttgataaaac attaactaga cttatatggt tggattttat    5280
ccttctatat tgagaagttg agaaaagtac aaaggcgtgc cacacgtgcg cgcactgccg    5340
ccgcccaggc cgtgccgcca atcaaaactc ataataacgt gagtttcttc ttttgtatta    5400
tcacgattaa tctttgtctg ttacgaactc tttgcttgtt tgtctgtctc ttgagttgac    5460
tgcgatccct tctcctgcct ctacctgcga gaataaaatc tcgagaattc gg            5512
```

<210> SEQ ID NO 16
<211> LENGTH: 2547
<212> TYPE: DNA
<213> ORGANISM: Artificial Sequence
<220> FEATURE:
<223> OTHER INFORMATION: HindIII - 2_32 promoter

<400> SEQUENCE: 16

```
aagcttagct agatcggatg gttaagaacc tagtaagagg aacttaagtt gtaggctaga      60
accaaaattt agtagaccta gagccagctc tagttaaatt gtaagggtgc gcataactcc     120
ataatccata attctagcca cccattgtgt cgccgaccca gagtcccaga ctaggaatcg     180
acgcggacag gcaggcagcc ctctccgact ccgtgggcac cgtcgtcgca gctactcgtt     240
gctccgtcta cgaaagaatc aattttttaaa gttgttctaa gtcaaacttt ttaaacttta    300
accaaatttc tagaaaaaaaa tactaagatt tatggtatca aattagtatc attagattca    360
ctatagaata tattttcata tgatacgtat tttatatcat agatttgtta ccattttcta    420
taaaattagt caaacttaaa aaagtttgac ggatacggat tctaagaatt gattcttta     480 tggacagagg gagtacatac agcaggctgt gtctgtgcaa acgtccggct tctacgacgg    540
gcggccaggt tgaggtcttg tttagatcca aaaagttttt ggattttaac actcactttc    600
```

```
attttttattt gacaaacatt gtccaatcat agagtaacta gacttaaaag attcgtctcg      660
caatttacag acaaattgtg caattagttt tttttatcat atttaatgct ctatgaatat      720
accataagat tcgatgtgat aaaaaatctt aaaaaaattg tttttttagt aaactaaaca      780
atgccgtgcc gtgggcgtgg gcgtggagaa catgcaatgc attgcatggg gaacatcgat      840
gaaccaaagt taatgggcac actaaactgc atgccccaga cacagtttta aaatttattt      900
actaatatag caacaaaaaa aaacaaatat atgcacgccc gcacgcacgt cctgtgcata      960
tatatatgca cggacgctat tcaaatcaac agggagagga cagtttggtc ggtggagtat     1020
ctatctacac taaaaaatac cgccctcctc tactcagctc gtccccgatt tttttaactc     1080
ctcctccaaa tcacaatcag atatcaaatc aaatcaaatc attctaaatc gaaaaaaaaa     1140 gaaatatta aatcaaatca agaaaaaata taagtcaaat acacagaata tcccatcatg     1200
ctcatcttgt ccttggatat tttgactctc tcctccaaat cagaatcgga tatcaaatca     1260
aatcaaatcg ttctaaaacc gaataaaaaa aagaaaatat caaaccaaat gaaatgaaat     1320
cgagaaaaaa aaaatcaaat atgcagggta tcgtagtacc atcctactct gttcagctca     1380
tccccaaatt ttttttgcct tgctcctcga aatcagaatc gaatatcaaa tcattctaaa     1440
tccaaatcag aaaagaaat atcaaaccaa attaaatgaa atcataaaaa aatataagtc     1500
aaatatgcaa agtatcattt tgactcgctc ctccaaatga gatcgaatat caaaatcgaa     1560
tcaaattgtt tgaaatctga attttaaaaa ataaaatatc aaaccaaatc aaatgaaatc     1620
ggaaaaaaat acaagtaaaa tacacagggt attgtcgtac caccctgctt tactcaactt     1680
gtccttggat ttttttgcat gtctcctcca aatcagaatc ggatatcaaa tcatatcgtt     1740
ccaaatccga attggaaaga agaaaatatc aaaccaaatc aaatgaaata gaaaaaaaat     1800
acaagttagt gtgttgttgc aactgtattg aaacttgacc tcttgccgcc tgcgcgaggg     1860
ctcgtgaact agcaggctgt cactgtaaaa ataatagtat caggtacaat aacagtgtga     1920
ttcgactgtt atatcattca tatacacgta aaagcggaga gagaaagcaa tgcttttgtt     1980
gatgagcttg tgacgcatgt caagacgctt tttctaagca gaggttaact cttcccatcc     2040
tatccttgta tattgaataa gaaaacaata tttagactat agaaagggac taattgttgt     2100
atgtgctaga ctctaaataa acttgtctaa taatgacttg gcttggctta tagataaatt     2160
ttattaggct tgctctaaaa cctgccctca cacatgatcc gaaacttgtg gggcaataaa     2220
aagcgaaact attctgtata ttaagctcgt gctttgtgct acctgaaaaa aaatacaaac     2280
aggtaagcca ttgcgtaaca aaaaaaaaat gaaaagaaca aagaaacaat taagaaatcc     2340
gcctacctga tcgtgcattg tgctcggtta ctaatgtact ttttaaaaat tggaatggat     2400
ggatggtttt cctctgactg gctggctggc tgcctgctgc ttataggagt actatataag     2460
tagacgcatg cagtacccaa acgacgacgc cgccaccacc gcaaaagcag caaaaccta     2520 gcttgttcac caccacaacc gccagcc                                        2547
```

<210> SEQ ID NO 17
<211> LENGTH: 907
<212> TYPE: DNA
<213> ORGANISM: Artificial Sequence
<220> FEATURE:
<223> OTHER INFORMATION: 2_32 terminator - EcoRI

<400> SEQUENCE: 17

```
cttgcatcat tgctgggagg gatccattcc atgcctgcgc tttgccagct gggaataatg       60
atagatgccc gtacgtacgt ctcgatatgc atacggttga tgttggtgtt gaataccctcg     120
```

```
cgctctcgta ttcgtatacg gagtagtagg tgaagtcagt tggtgcaatg tattccatct      180
gttcgtggcc tatatattat gcaaaaaaat aatgtcagaa taattaaatc acatgtgtga      240
gattgaataa ataaccaatt tctccgcatc gtttatatat taattgtaca gtatatatag      300
taggatcagg agtaatgcat gcttagctac tctatatacc tctcaaaaac gattgtgtac      360
tataaattca taataggcga aggacctgct gtataaacgc tgctggggtt accggccggg      420
catatacata tcctcctttc ttatcagcaa ggcctgctgt actaaattca taataaggac      480
cccagcagcg tttcgatcgt cgacatacat atctcctacc tacagcttct tcgacggaca      540
aaacttggtg tcttgctgtg gatttataat gggcttggcc catatacatt tagtaaatca      600
ataaactcgg tgtataatta atacaatacg ggatatattg ataaaacatt aactagactt      660
atatggttgg atttttatcct tctatattga gaagttgaga aaagtacaaa ggcgtgccac      720
acgtgcgcgc actgccgccg cccaggccgt gccgccaatc aaaactcata ataacgtgag      780
tttcttcttt tgtattatca cgattaatct ttgtctgtta cgaactcttt gcttgtttgt      840
ctgtctcttg agttgactgc gatcccttct cctgcctcta cctgcgagaa taaaatctcg      900
agaattc                                                                907

<210> SEQ ID NO 18
<211> LENGTH: 6015
<212> TYPE: DNA
<213> ORGANISM: Artificial Sequence
<220> FEATURE:
<223> OTHER INFORMATION: 2_35 promoter::GUSPlus::2_35-3' cassette

<400> SEQUENCE: 18
tctgggtact gctattgagg ccttgtctcc caaaatgggg cttgaatatg catgagtata       60
agaagacaga ataacttgaa cacatgtcaa caagggacca caatcaaag tattatattg      120 tattcaagta tactttgcta ttatatctta tagaatatat tatatattct ccaacgccat      180
aatttcataa tagatgggta gccacggttc atcctgggct aagtttcaac ccaactggaa      240
caatttgtaa ctttattgtg tcgtaattgt atcagcttat ggggttagcc attctaccct      300
atgtaataat atatgtttat atgttgcaat gcttatggtc ctaaggtttc actaagtgct      360
tatcattgtt ggctgcatca ccgccagtct gttagaaaaa aggacatcac gccaggttta      420 taaccaact gtagtgaata tagcgacata atttgagata tcattgggat ttacatatcg      480
tttctttttt ttttctttttc acaaagcact tagccactta ggacacttcc tttcttcctt      540
ccttccttta agctggacta ggaaacacaa agagtctggg ccttgacgat agcatggatt      600
gggacgactt tgtcttttgg gcttcttggt catcatcgtc tccatgcgtg tgccaccagc      660
gttcccgttg cctcctcat cctttctgac agatgccccc ttggtaccgt gacatttctc      720
tcttcttgag aaccggcttg acccaagcca gtgccaccgg aaaaatgagc ttcagcacgt      780
gctcattctc ctaggttgac gtacacaagt gcacgggcca ttctgaccaa tgaacaagaa      840
cttgattgaa acagaaactt catcattgcg tctacacact tagcataatg attagtccta      900
agatttcatt aattattaaa atcaaactag gctttcata tgggtacgta ccctatgtct      960
acttgaagca ggccttgaca caagagtcca agaaggcata ttccatagtt ctacgattgt     1020
cgtcggtgtc ctcttggtaa cagcgattcc ctccttggtc aatctgctgg tgatcgcgat     1080
gaccctgtca atgagatcgg aggagacatc gggcaacaac ctcctcttta agactcggtc     1140
acctgacctt tgttgagatc atcccaacac aaactgctaa aaatctcggt tcacgatttg     1200
```

-continued

```
atccatcatc tgaagcaagt gcaaacataa ttgctgattt tgtgtcaaat gagaaatata   1260
atgcaatagt gatgtgaagt atatacccct cttttttttt aggaaacgct aatggtttga   1320
tgacaatttt gttgtgcttt ttactttctt ttcacattta ttttgtactt ctgattttt    1380
aaagtgtaaa acacaattac tttgaagaat tgggaaacaa tcagctcatg actccagcag   1440
taaaaaaggt taaactcgaa aaaagggga aatgatggt ttcatccgtg actttgaaga     1500
ttcatgaatc ggagtaaaaa aagaagaatt gtgaatcaca aaccctttgg ctcttgtatt   1560
cgaaaaagtg ggtcctgtta ctcctgtagg tgtcatatgt gacaaaaatt atcatagctc   1620
aaagaaaaaa aactgtaaac aaaaatggct acccacctgt ttcgtgacgt ggtggctctt   1680
gtacatatat ataggggtg tttgagattg ctctgctcca aatttttta gctccgcttt      1740
atgtttttta gtcaaacagt ttcaggtcca cgcactcagt tttaaaaaaa tggtggagtt   1800
gtgagagcac ctagagaggt actctacaaa ctccggtttt ttgtgaagct gtttcatggt   1860
ggagtttgtg gagcagagtt cgtgaagcaa tgccaaacac ctagtaacat ggtgttgtac   1920
gtggccgaaa ccaccgtagt tgaaaaaaca aaaaccgtgg aagcaaaagc cgctataggg   1980
taacttaata agctcattaa catacggtaa cacaaacaaa gaagaagttt tcacacgtgt   2040
gtgttatatt tttctgttca gattacccaa gatcggagat acgttttga attaggattc     2100
ctttcggcgg agagacgttt ttgaattagt aaaaataaaa atataaaaga tacgctgccg   2160
atgcgtttc gatacatatt ggagaagtat cagaaaacaa aataaaaata acacaaaatc    2220
tgatagtcgt gagggatat gtatatcagc ctggtcaact cacgccggcc ggtactactc     2280
tgtgagggct gccactactg cttatcggag aagtattcat cagaaaataa aaacaaaaaa   2340
cctgatactc gaggatatgc tacgtatcac aactcacgca gatacgacgg ctagctgaac   2400
agcccacacc cacaccctct ttataaatgc atggctcatg cggcgctgct ccatattgct   2460
cccattcatc ctcgtcctcc acgagcctgg ctcacaggct gtacgtcgtg cgtcgtcgtc   2520
gatggtagat ctgagggtaa atttctagtt tttctccttc attttcttgg ttaggaccct   2580
tttctctttt tatttttttg agctttgatc tttctttaaa ctgatctatt ttttaattga   2640
ttggttatgg tgtaaatatt acatagcttt aactgataat ctgattactt tatttcgtgt   2700
gtctatgatg atgatgatag ttacagaacc gacgaactag tctgtacccg atcaacaccg   2760
agacccgtgg cgtcttcgac ctcaatggcg tctggaactt caagctggac tacgggaaag   2820
gactggaaga gaagtggtac gaaagcaagc tgaccgacac tattagtatg gccgtcccaa   2880
gcagttacaa tgcattggc gtgaccaagg aaatccgcaa ccatatcgga tatgtctggt     2940
acgaacgtga gttcacggtg ccggcctatc tgaaggatca gcgtatcgtg ctccgcttcg   3000
gctctgcaac tcacaaagca attgtctatg tcaatggtga gctggtcgtg gagcacaagg   3060
gcggattcct gccattcgaa gcggaaatca acaactcgct gcgtgatggc atgaatcgcg   3120
tcaccgtcgc cgtggacaac atcctcgacg atagcaccct cccggtgggg ctgtacagcg   3180
agcgccacga agagggcctc ggaaaagtca ttcgtaacaa gccgaacttc gacttcttca   3240
actatgcagg cctgcaccgt ccggtgaaaa tctacacgac cccgtttacg tacgtcgagg   3300
acatctcggt tgtgaccgac ttcaatggcc caaccgggac tgtgacctat acggtggact   3360
tcaaggcaa agccgagacc gtgaaagtgt cggtcgtgga tgaggaaggc aaagtggtcg   3420
caagcaccga gggcctgagc ggtaacgtgg agattccgaa tgtcatcctc tgggaaccac   3480
tgaacacgta tctctaccag atcaaagtgg aactggtgaa cgacggactg accatcgatg   3540
tctatgaaga gccgttcggc gtgcggaccg tggaagtcaa cgacggcaag ttcctcatca   3600
```

```
acaacaaacc gttctacttc aagggctttg gcaaacatga ggacactcct atcaacggcc   3660
gtggctttaa cgaagcgagc aatgtgatgg atttcaatat cctcaaatgg atcggcgcca   3720
acagcttccg gaccgcacac tatccgtact ctgaagagtt gatgcgtctt gcggatcgcg   3780
agggtctggt cgtgatcgac gagactccgg cagttggcgt gcacctcaac ttcatggcca   3840
ccacgggact cggcgaaggc agcgagcgcg tcagtacctg ggagaagatt cggacgtttg   3900
agcaccatca gacgttctc cgtgaactgg tgtctcgtga caagaaccat ccaagcgtcg   3960
tgatgtggag catcgccaac gaggcggcga ctgaggaaga gggcgcgtac gagtacttca   4020
agccgttggt ggagctgacc aaggaactcg acccacagaa gcgtccggtc acgatcgtgc   4080
tgtttgtgat ggctaccccg gagacggaca aagtcgccga actgattgac gtcatcgcgc   4140
tcaatcgcta taacgatgg tacttcgatg gcggtgatct cgaagcggcc aaagtccatc   4200
tccgccagga atttcacgcg tggaacaagc gttgcccagg aaagccgatc atgatcactg   4260 agtacgcgc agacaccgtt gcgggctttc acgacattga tccagtgatg ttcaccgagg   4320
aatatcaagt cgagtactac caggcgaacc acgtcgtgtt cgatgagttt gagaacttcg   4380
tgggtgagca agcgtggaac ttcgcggact tcgcgacctc tcagggcgtg atgcgcgtcc   4440
aaggaaacaa gaagggcgtg ttcactcgtg accgcaagcc gaagctcgcc gcgcacgtct   4500
ttcgcgagcg ctggaccaac attccagatt tcggctacaa gaacgctagc catcaccatc   4560
accatcacgt gtgatagcag aggaacttac tgtcacaacg cctctgccaa gtccaataat   4620
gtggatccgt ggccccatgg ccgtctactt atctatactg tacttgaatc aataatctcc   4680
ttggacatat ttgccatgac atgtcaaata atttctacac gacttttgat ttatggatca   4740
aaaaactgtt gcaaccttgc tcttcttgtt ttactctttt tttatctttt tttatttcct   4800
aagttgttgt actgtgtttt cctctttta atttcaataa atctcctata ggggctaagg   4860
cccctccagt tcttttttta aaaataatt tttaccactt gtggagatat tctaaattca   4920
ctgttcatag gcttccattt gtattgatcg agacattgag tggagtgccc tatccttcca   4980
ccccaccctc tgctggtcct ctttattaag ggatccgtct atatttgact tgagtgatgt   5040
ccgtgttttg taaactaaat agtgaattta tacgtatcgt gtagctttag gaagacgaca   5100
cttatagaca cgagggttat actggtcagg cggccgcagc cctacgtcta gtctcaaaga   5160
tggtttaagt ctgtgtttct cgattgaatg ctttgaagtt cttacgatag gttaagtaag   5220
ctaaggaaga gaggtaggag ggaggagtga ggtgaacgaa tgatgagtac atgcccgatc   5280
ttctgagagg taactggtaa gtttgatttg tggagatctc gacgttggcg atccggcttc   5340
aaaccagaca cgattcgaac cctgcaaccg ttacaccact gatccgttgg ttatcaacca   5400
agcacaactt gattgacctc gccaagaagg ctttcctgc aagcgaatcg aagaacacaa   5460
gcaagaaggt ttaaacatgc aatctgaaat tgcaaatatg aatgacacga atatcaatag   5520
agggttcaag aactcggttt caaaggacta atcgacgcag tggaggagat taagaacggg   5580
agcactggat cattgtaaaa ggatttgtca ccacagttac aatgaacgat tcagtttctc   5640
gatggaaaac taaactctaa acaaaaccca agtctcgaca gcttgcggct gcgtggaata   5700
taaaagagag gcgtcctagg attggaaggc gaccaggat ggtgcccaca acttgggctt   5760
aaggtctgac tcattacata gccaagttgg cttaaaatag atgacgcatc aacttatcgt   5820
agtcacacag attaatccac gtgtcatctg gagctgggac aagatccaaa acgatgacat   5880
cgtcgtcccc tttccaatga gtccaagatc tccctatttc gatgtcgtat gaagaagtta   5940
```

```
tgatcgaaac attaacgacg tgtctgctga attcgagggt gacgtgacag ctgagttgga    6000
gatgagttgc aactt                                                     6015

<210> SEQ ID NO 19
<211> LENGTH: 6045
<212> TYPE: DNA
<213> ORGANISM: Artificial Sequence
<220> FEATURE:
<223> OTHER INFORMATION: SfiI-2_35 promoter::GUS-plus::2_35 terminator-
      SfiI cassette

<400> SEQUENCE: 19
gcggccctta aggcctctgg gtactgctat tgaggccttg tctcccaaaa tggggcttga      60
atatgcatga gtataagaag acagaataac ttgaacacat gtcaacaagg gaccaacaat     120
caaagtatta tattgtattc aagtatactt tgctattata tcttatagaa tatattatat     180
attctccaac gccataattt cataatagat gggtagccac ggttcatcct gggctaagtt     240
tcaacccaac tggaacaatt tgtaacttta tgtgtcgta attgtatcag cttatggggt      300
tagccattct accctatgta ataatatatg tttatatgtt gcaatgctta tggtcctaag     360
gtttcactaa gtgcttatca ttgttggctg catcaccgcc agtctgttag aaaaaaggac     420
atcacgccag gtttataaac caactgtagt gaatatagcg ataatttg agatatcatt     480 gggatttaca tatcgtttct ttttttttc ttttcacaaa gcacttagcc acttaggaca     540
cttcctttct tccttccttc ctttaagctg gactaggaaa cacaagagt ctgggccttg     600 acgatagcat ggattgggac gactttgtct tttgggcttc ttggtcatca tcgtctccat     660
gcgtgtgcca ccagcgttcc cgttgccctc ctcatccttt ctgacagatg cccccttggt     720
accgtgacat ttctctcttc ttgagaaccg gcttgaccca agccagtgcc accggaaaaa     780
tgagcttcag cacgtgctca ttctcctagg ttgacgtaca caagtgcacg ggccattctg     840
accaatgaac aagaacttga ttgaaacaga aacttcatca ttgcgtctac acacttagca     900
taatgattag tcctaagatt tcattaatta ttaaaatcaa actagggctt tcatatgggt     960 acgtaccta tgtctacttg aagcaggcct tgacacaaga gtccaagaag gcatattcca    1020
tagttctacg attgtcgtcg gtgtcctctt ggtaacagcg attccctcct tggtcaatct    1080
gctggtgatc gcgatgaccc tgtcaatgag atcggaggag acatcgggca caacctcct    1140 ctttaagact cggtcacctg acctttgttg agatcatccc aacacaaact gctaaaaatc    1200
tcggttcacg atttgatcca tcatctgaag caagtgcaaa cataattgct gattttgtgt    1260
caaatgagaa atataatgca atagtgatgt gaagtatata cccttctttt tttttaggaa    1320
acgctaatgg tttgatgaca attttgttgt gctttttact ttcttttcac atttattttg    1380
tacttctgat tttttaaagt gtaaaacaca attactttga agaattggga acaatcagc     1440 tcatgactcc agcagtaaaa aaggttaaac tcgaaaaaaa ggggaaaatg atggtttcat    1500
ccgtgacttt gaagattcat gaatcggagt aaaaaaagaa gaattgtgaa tcacaaaccc    1560
tttggctctt gtattcgaaa aagtgggtcc tgttactcct gtaggtgtca tatgtgacaa    1620
aaattatcat agctcaaaga aaaaaaactg taaacaaaaa tggctaccca cctgtttcgt    1680
gacgtggtgg ctcttgtaca tatatatagg gggtgtttga gattgctctg ctccaaattt    1740
ttttagctcc gctttatgtt ttttagtcaa acagtttcag gtccacgcac tcagttttaa    1800
aaaaatggtg gagttgtgag agcacctaga gaggtactct acaaactccg gttttttgtg    1860
aagctgtttc atggtggagt ttgtggagca gagttcgtga agcaatgcca aacacctagt    1920
```

```
aacatggtgt tgtacgtggc cgaaaccacc gtagttgaaa aacaaaaac cgtggaagca      1980
aaagccgcta tagggtaact taataagctc attaacatac ggtaacacaa acaaagaaga    2040
agttttcaca cgtgtgtgtt atattttct gttcagatta cccaagatcg gagatacgtt    2100
tttgaattag gattcctttc ggcggagaga cgttttgaa ttagtaaaaa taaaaatata    2160
aaagatacgc tgccgatgcg ttttcgatac atattggaga agtatcagaa aacaaaataa   2220
aaataacaca aaatctgata gtcgtgaggg gatatgtata tcagcctggt caactcacgc   2280
cggccggtac tactctgtga gggctgccac tactgcttat cggagaagta ttcatcagaa   2340
aataaaaaca aaaaacctga tactcgagga tatgctacgt atcacaactc acgcagatac   2400
gacggctagc tgaacagccc acacccacac cctctttata aatgcatggc tcatgcggcg   2460
ctgctccata ttgctcccat tcatcctcgt cctccacgag cctggctcac aggctgtacg   2520
tcgtgcgtcg tcgtcgatgg tagatctgag ggtaaatttc tagttttct ccttcatttt    2580
cttggttagg accctttct cttttattt ttttgagctt tgatcttct ttaaactgat      2640
ctatttttta attgattggt tatggtgtaa atattacata gctttaactg ataatctgat   2700
tactttattt cgtgtgtcta tgatgatgat gatagttaca gaaccgacga actagtctgt   2760
acccgatcaa caccgagacc cgtggcgtct tcgacctcaa tggcgtctgg aacttcaagc   2820
tggactacgg gaaaggactg gaagagaagt ggtacgaaag caagctgacc gacactatta   2880
gtatggccgt cccaagcagt tacaatgaca ttggcgtgac caaggaaatc cgcaaccata   2940
tcggatatgt ctggtacgaa cgtgagttca cggtgccggc ctatctgaag gatcagcgta   3000
tcgtgctccg cttcggctct gcaactcaca aagcaattgt ctatgtcaat ggtgagctgg   3060
tcgtggagca aagggcgga ttcctgccat cgaagcgga aatcaacaac tcgctgcgtg     3120
atggcatgaa tcgcgtcacc gtcgccgtgg acaacatcct cgacgatagc accctcccgg   3180
tggggctgta cagcgagcgc cacgaagagg gcctcggaaa agtcattcgt aacaagccga   3240
acttcgactt cttcaactat gcaggcctgc accgtccggt gaaaatctac acgaccccgt   3300
ttacgtacgt cgaggacatc tcggttgtga ccgacttcaa tggcccaacc gggactgtga   3360
cctatacggg ggactttcaa ggcaaagccg agaccgtgaa agtgtcggtc gtggatgagg   3420
aaggcaaagt ggtcgcaagc accgagggcc tgagcggtaa cgtggagatt ccgaatgtca   3480
tcctctggga accactgaac acgtatctct accagatcaa agtggaactg gtgaacgacg   3540
gactgaccat cgatgtctat gaagagccgt tcggcgtgcg gaccgtggaa gtcaacgacg   3600
gcaagttcct catcaacaac aaaccgttct acttcaaggg cttttggcaaa catgaggaca   3660
ctcctatcaa cggccgtggc tttaacgaag cgagcaatgt gatggatttc aatatcctca   3720
aatggatcgg cgccaacagc ttccggaccg cacactatcc gtactctgaa gagttgatgc   3780
gtcttgcgga tcgcgagggt ctggtcgtga tcgacgagac tccggcagtt ggcgtgcacc   3840
tcaacttcat ggccaccacg ggactcggcg aaggcagcga gcgcgtcagt acctgggaga   3900
agattcggac gtttgagcac catcaagacg ttctccgtga actggtgtct cgtgacaaga   3960
accatccaag cgtcgtgatg tggagcatcg ccaacgaggc ggcgactgag aagagggcg    4020
cgtacgagta cttcaagccg ttggtggagc tgaccaagga actcgaccca cagaagcgtc   4080
cggtcacgat cgtgctgttt gtgatggcta ccccggagac ggacaaagtc gccgaactga   4140
ttgacgtcat cgcgctcaat cgctataacg gatggtactt cgatggcggt gatctcgaag   4200
cggccaaagt ccatctccgc caggaatttc acgcgtggaa caagcgttgc ccaggaaagc   4260
cgatcatgat cactgagtac ggcgcagaca ccgttgcggg cttcacgac attgatccag   4320
```

```
tgatgttcac cgaggaatat caagtcgagt actaccaggc gaaccacgtc gtgttcgatg   4380
agtttgagaa cttcgtgggt gagcaagcgt ggaacttcgc ggacttcgcg acctctcagg   4440
gcgtgatgcg cgtccaagga aacaagaagg gcgtgttcac tcgtgaccgc aagccgaagc   4500
tcgccgcgca cgtctttcgc gagcgctgga ccaacattcc agatttcggc tacaagaacg   4560
ctagccatca ccatcaccat cacgtgtgat agcagaggaa cttactgtca caacgcctct   4620
gccaagtcca ataatgtgga tccgtggccc catggccgtc tacttatcta tactgtactt   4680
gaatcaataa tctccttgga catatttgcc atgacatgtc aaataatttc tacacgactt   4740
ttgatttatg gatcaaaaaa ctgttgcaac cttgctcttc ttgttttact cttttttttat   4800 ctttttttat ttcctaagtt gttgtactgt gttttcctct ttttaatttc aataaatctc   4860
ctataggggc taaggcccct ccagttcttt ttttaaaaaa taattttttac cacttgtgga   4920 gatattctaa attcactgtt cataggcttc catttgtatt gatcgagaca ttgagtggag   4980
tgccctatcc ttccaccccca ccctctgctg gtcctcttta ttaagggatc cgtctatatt   5040
tgacttgagt gatgtccgtg ttttgtaaac taaatagtga atttatacgt atcgtgtagc   5100
tttaggaaga cgacacttat agacacgagg gttatactgg tcaggcggcc gcagccctac   5160
gtctagtctc aaagatggtt taagtctgtg tttctcgatt gaatgctttg aagttcttac   5220
gataggttaa gtaagctaag gaagagaggt aggagggagg agtgaggtga acgaatgatg   5280
agtacatgcc cgatcttctg agaggtaact ggtaagtttg atttgtggag atctcgacgt   5340
tggcgatccg gcttcaaacc agacacgatt cgaaccctgc aaccgttaca ccactgatcc   5400
gttggttatc aaccaagcac aacttgattg acctcgccaa gaaggctttt cctgcaagcg   5460
aatcgaagaa cacaagcaag aaggtttaaa catgcaatct gaaattgcaa atatgaatga   5520
cacgaatatc aatagagggt tcaagaactc ggtttcaaag gactaatcga cgcagtggag   5580
gagattaaga acgggagcac tggatcattg taaaaggatt tgtcaccaca gttacaatga   5640
acgattcagt ttctcgatgg aaaactaaac tctaaacaaa acccaagtct cgacagcttg   5700
cggctgcgtg gaatataaaa gagaggcgtc ctaggattgg aaggcgacca gggatggtgc   5760
ccacaacttg ggcttaaggt ctgactcatt acatagccaa gttggcttaa aatagatgac   5820
gcatcaactt atcgtagtca cacagattaa tccacgtgtc atctggagct gggacaagat   5880
ccaaaacgat gacatcgtcg tcccctttcc aatgagtcca agatctccct atttcgatgt   5940
cgtatgaaga agttatgatc gaaacattaa cgacgtgtct gctgaattcg agggtgacgt   6000
gacagctgag ttggagatga gttgcaactt ggccgccatg ccgc                   6045
```

<210> SEQ ID NO 20
<211> LENGTH: 2534
<212> TYPE: DNA
<213> ORGANISM: Artificial Sequence
<220> FEATURE:
<223> OTHER INFORMATION: SfiI-2_35 promoter

<400> SEQUENCE: 20

```
ggcccttaag gcctctgggt actgctattg aggccttgtc tcccaaaatg gggcttgaat    60
atgcatgagt ataagaagac agaataactt gaacacatgt caacaaggga ccaacaatca   120
aagtattata ttgtattcaa gtatactttg ctattatatc ttatagaata tattatatat   180
tctccaacgc cataatttca taatagatgg gtagccacgg ttcatcctgg gctaagtttc   240
aacccaactg gaacaatttg taactttatt gtgtcgtaat tgtatcagct tatggggtta   300
```

```
gccattctac cctatgtaat aatatatgtt tatatgttgc aatgcttatg gtcctaaggt      360
ttcactaagt gcttatcatt gttggctgca tcaccgccag tctgttagaa aaaaggacat      420
cacgccaggt ttataaacca actgtagtga atatagcgac ataatttgag atatcattgg      480
gatttacata tcgtttcttt tttttttctt ttcacaaagc acttagccac ttaggacact      540
tcctttcttc cttccttcct ttaagctgga ctaggaaaca caaagagtct gggccttgac      600
gatagcatgg attgggacga cttgtctttt tgggcttctt ggtcatcatc gtctccatgc      660
gtgtgccacc agcgttcccg ttgccctcct catcctttct gacagatgcc cccttggtac      720
cgtgacattt ctctcttctt gagaaccggc ttgacccaag ccagtgccac cggaaaaatg      780
agcttcagca cgtgctcatt ctcctaggtt gacgtacaca agtgcacggg ccattctgac      840
caatgaacaa gaacttgatt gaaacagaaa cttcatcatt gcgtctacac acttagcata      900
atgattagtc ctaagatttc attaattatt aaaatcaaac tagggctttc atatgggtac      960
gtaccctatg tctacttgaa gcaggccttg acacaagagt ccaagaaggc atattccata     1020
gttctacgat tgtcgtcggt gtcctcttgg taacagcgat tccctccttg gtcaatctgc     1080
tggtgatcgc gatgaccctg tcaatgagat cggaggagac atcgggcaac aacctcctct     1140
ttaagactcg gtcacctgac ctttgttgag atcatcccaa cacaaactgc taaaaatctc     1200
ggttcacgat ttgatccatc atctgaagca agtgcaaaca taattgctga ttttgtgtca     1260
aatgagaaat ataatgcaat agtgatgtga agtatatacc cttcttttt tttaggaaac      1320 gctaatggtt tgatgacaat tttgttgtgc ttttactttt cttttcacat ttattttgta     1380
cttctgattt tttaaagtgt aaaacacaat tactttgaag aattgggaaa caatcagctc     1440
atgactccag cagtaaaaaa ggttaaactc gaaaaaaagg ggaaaatgat ggtttcatcc     1500
gtgactttga agattcatga atcggagtaa aaaagaagaa attgtgaatc acaaacccctt     1560 tggctcttgt attcgaaaaa gtgggtcctg ttactcctgt aggtgtcata tgtgacaaaa     1620
attatcatag ctcaaagaaa aaaaactgta acaaaaatg gctacccacc tgtttcgtga      1680
cgtggtggct cttgtacata tatataggggg gtgtttgaga ttgctctgct ccaaattttt     1740
ttagctccgc tttatgtttt ttagtcaaac agtttcaggt ccacgcactc agttttaaaa     1800
aaatggtgga gttgtgagag cacctagaga ggtactctac aaactccggt ttttttgtgaa     1860 gctgtttcat ggtggagttt gtggagcaga gttcgtgaag caatgccaaa cacctagtaa     1920
catggtgttg tacgtggccg aaaccaccgt agttgaaaaa acaaaaaccg tggaagcaaa     1980
agccgctata gggtaactta ataagctcat taacatacgg taacacaaac aaagaagaag     2040
ttttcacacg tgtgtgttat atttttctgt tcagattacc caagatcgga gatacgtttt     2100
tgaattagga ttcctttcgg cggagagacg ttttgaatt agtaaaaata aaatataaaa      2160
agatacgctg ccgatgcgtt ttcgatacat attggagaag tatcagaaaa caaaataaaa     2220
ataacacaaa atctgatagt cgtgagggga tatgtatatc agcctggtca actcacgccg     2280
gccggtacta ctctgtgagg gctgccacta ctgcttatcg gagaagtatt catcagaaaa     2340
taaaaacaaa aaacctgata ctcgaggata tgctacgtat cacaactcac gcagatacga     2400
cggctagctg aacagcccac acccacaccc tctttataaa tgcatggctc atgcggcgct     2460
gctccatatt gctcccattc atcctcgtcc tccacgagcc tggctcacag gctgtacgtc     2520
gtgcgtcgtc gtcg                                                        2534

<210> SEQ ID NO 21
<211> LENGTH: 1454
```

```
<212> TYPE: DNA
<213> ORGANISM: Artificial Sequence
<220> FEATURE:
<223> OTHER INFORMATION: 2_35 terminator- SfiI

<400> SEQUENCE: 21
tagcagagga acttactgtc acaacgcctc tgccaagtcc aataatgtgg atccgtggcc      60
ccatggccgt ctacttatct atactgtact tgaatcaata atctccttgg acatatttgc     120
catgacatgt caaataattt ctacacgact tttgatttat ggatcaaaaa actgttgcaa     180
ccttgctctt cttgttttac tcttttttta tcttttttta tttcctaagt tgttgtactg     240
tgttttcctc tttttaattt caataaatct cctataggggg ctaaggcccc tccagttctt     300
tttttaaaaa ataattttta ccacttgtgg agatattcta aattcactgt tcataggctt     360
ccatttgtat tgatcgagac attgagtgga gtgccctatc cttccacccc accctctgct     420
ggtcctcttt attaagggat ccgtctatat ttgacttgag tgatgtccgt gttttgtaaa     480
ctaaatagtg aatttatacg tatcgtgtag ctttaggaag acgacactta tagacacgag     540
ggttatactg gtcaggcggc cgcagccctaa cgtctagtct caaagatggt ttaagtctgt     600
gtttctcgat tgaatgcttt gaagttctta cgataggtta agtaagctaa ggaagagagg     660
taggagggag gagtgaggtg aacgaatgat gagtacatgc ccgatcttct gagaggtaac     720
tggtaagttt gatttgtgga gatctcgacg ttggcgatcc ggcttcaaac cagacacgat     780 tcgaccctg caaccgttac accactgatc cgttggttat caaccaagca caacttgatt     840
gacctcgcca agaaggcttt tcctgcaagc gaatcgaaga acacaagcaa gaaggtttaa     900
acatgcaatc tgaaattgca aatatgaatg acacgaatat caatagaggg ttcaagaact     960
cggtttcaaa ggactaatcg acgcagtgga ggagattaag aacgggagca ctggatcatt    1020
gtaaaaggat ttgtcaccac agttacaatg aacgattcag tttctcgatg gaaaactaaa    1080
ctctaaacaa aacccaagtc tcgacagctt gcggctgcgt ggaatataaa agagaggcgt    1140
cctaggattg gaaggcgacc agggatggtg cccacaactt gggcttaagg tctgactcat    1200
tacatagcca agttggctta aaatagatga cgcatcaact tatcgtagtc acacagatta    1260
atccacgtgt catctggagc tgggacaaga tccaaaacga tgacatcgtc gtccccttttc   1320 caatgagtcc aagatctccc tatttcgatg tcgtatgaag aagttatgat cgaaacatta    1380
acgacgtgtc tgctgaattc gagggtgacg tgacagctga gttggagatg agttgcaact    1440
tggccgccat ggcc                                                     1454

<210> SEQ ID NO 22
<211> LENGTH: 6156
<212> TYPE: DNA
<213> ORGANISM: Artificial Sequence
<220> FEATURE:
<223> OTHER INFORMATION: 2_36 promoter::GUSPlus::2_36-3' cassette

<400> SEQUENCE: 22
caatatgcat cggcatcttg ccgatgaggc ggctgcggat ctggcacctg atggcgaacc      60
tccacgtgtc tgttcgggac gtgatctgta cggaacattg tattgatcac ctgtcctcca     120
atctgcggac caccaaactg ctgtccaccg attggctgtc ctccgaattg ctgtccaaaa     180
ttcattggct ggttgggaat ccctgacct tggaacccgg gatagacctg cccttgctgg      240
aaccctgtag tctggtaact ctgctgggc gattgtggaa aggcttgctg tccaaaccat     300
ccactattag cgttcatcgg catagatgct gccgatgatt ggtaattggg taccgtcgtt     360
```

```
gaattgacat accccgactg ggccgcagac ctctgttgta tcagcattga ctttgccgat      420 gcgtttgggca tctggaacat tgaatcttga ggatttccag tgtgaggcct tgcagtagtg    480
gttgtggtat accgaggact ctggttcatc ggcgcattgg gaggtgccga tgtcatagga    540
gttttgcccc tcatgtcagt tatctgtgat gttcccggtg tcacctctgg aggcataccg    600
taaccccacc agtgggagg aagagtcaac cctgacattg ccaatgccaa catatctgtt     660
gtcagtttat gctgcccaac tgaaatctgt gggttggttg ccatcggcat agatagtgca    720
ccagtagtcc ccgatgtact tggagggacg gcagattgtg cacttgcatt cgtcaaggca    780
gccgacggag ccgtgacctc tggtgccgtt ggctgatgat gggaggggcc cacatactct    840
ggtgggattt gtccttcctt gaaagtcctt gccacggcat tgaaaaccgt attagacagt    900
acaccagctt ggttaatcaa cgctcgattg atggcattgt caaccatatc ttgaagcttg    960
ccaggattgg cgtcaaaggt aacctgccgt ggtgccggca gcgcatcttt ctgaaccact   1020
tcgccgctcc tgtttatgct gaaagacctc aggcattgct gcttgaactc ttccatggct   1080
tgggcaatag cttgcttctg ctcatccttg aggttgccct ccgtcacggg gatgacgttc   1140
tcttgatcga ggtcagagat cgacatgttg atcttgatct tgaatctgtc ccaccgggcg   1200 tgccaaaga tgtgttgatg caaaagctga tctgcaaaca caagggcta atacccgatt     1260 tcaacgttaa ggcgtgccag ccgatttgac cttactatcg gcaaaggtga taactcgaat   1320
actttggtcc cgacaacagc gatgcgccca gatgccacgg ccaagaggta ttcacgcgga   1380
acttgagaac acgccgagct taagtcgacg aattcctaag aactcgtaat aaaaaggaaa   1440
aagtatgaca aagtcgtcga aatagtagat gctggaatat gagtaaaaac ttgtgtttga   1500
ttgattgata gatcattaca aggccctagg gtctatattt ataccctgct caaagagtta   1560
caaccagaca caattagaat tcgaattcca aattacacgg aatccgtata caaaacgatg   1620
taaataatta aggaaataac aaaactatcc cccgtgacaa actgaaactc ctccacacaa   1680
cgaccggcag cttccggact ccctcttttg catcatcggc agaccctttg ccatagtcat   1740
cggcagactt tcttatctag ccatcggcac aatcacatca ctgtctgtag acttagtcac   1800
gttcagcttc tccttcatcg gcaactatcc tcatcggcaa cccaccctgt agacagcata   1860
ctgccacctt atcctgccat cctagacaca tgcccaaaaa cggtgtcaac agtacttggt   1920
gtcttggtga ttaatacta tcagcgaatc aggtcaacga tctactagca attaacaata    1980
tatcatttct taatctttgg ctagttccgt ttcaattaga aaactatctc taccactcat   2040
ctgcatgcta ttgttcttaa ttaattactt gatatatatg gagcatatct ctaccactct   2100
catctgcaca tgctaatata atatatagtg atttgcacga ttcacaatca ataatttgca   2160
tgataatata ctggaacacg tgaaccagag gcacttacgg ccgcgtgttt attacttaat   2220
ttgccatata agatactata tgattccttt cacagattgg cagagatatg acatgtgtta   2280
tcttattctg tgattaacta tgtatatatg cccgggattt aattttttgcc tgatccgaaa   2340 caaatgggga accactactg cgtcgcattc ctcgcataag atatattcta cagtaataaa   2400
caacgacgtc tgcccacaga acgaaatcgc tcgaagcctc aaaacgacgg acggagtaac   2460
caatgcatgc ccaagctctc tatatatatt cgcttgaacg tctctccaat cacatcacac   2520
ggcgagctag ctaggaaaca acacacatc aacatacagc aaacattaga caagaatcaa    2580
acacgttcgc aggaaaagaa tagaagctag ggaggaggaa atggtagatc tgagggtaaa   2640
tttctagttt ttctccttca ttttcttggt taggacccctt ttctcttttt atttttttga   2700
gctttgatct ttctttaaac tgatctattt tttaattgat tggttatggt gtaaatatta   2760
```

```
catagcttta actgataatc tgattacttt atttcgtgtg tctatgatga tgatgatagt    2820
tacagaaccg acgaactagt ctgtacccga tcaacaccga dacccgtggc gtcttcgacc    2880
tcaatggcgt ctggaacttc aagctggact acgggaaagg actggaagag aagtggtacg    2940
aaagcaagct gaccgacact attagtatgg ccgtcccaag cagttacaat gacattggcg    3000
tgaccaagga aatccgcaac catatcggat atgtctggta cgaacgtgag ttcacggtgc    3060
cggcctatct gaaggatcag cgtatcgtgc tccgcttcgg ctctgcaact cacaaagcaa    3120
ttgtctatgt caatggtgag ctggtcgtgg agcacaaggg cggattcctg ccattcgaag    3180
cggaaatcaa caactcgctg cgtgatggca tgaatcgcgt caccgtcgcc gtggacaaca    3240
tcctcgacga tagcacccte ccggtggggc tgtacagcga gcgccacgaa gagggcctcg    3300
gaaaagtcat tcgtaacaag ccgaacttcg acttcttcaa ctatgcaggc ctgcaccgtc    3360
cggtgaaaat ctacacgacc ccgtttacgt acgtcgagga catctcggtt gtgaccgact    3420
tcaatggccc aaccgggact gtgacctata cggtggactt tcaaggcaaa gccgagaccg    3480
tgaaagtgtc ggtcgtggat gaggaaggca aagtggtcgc aagcaccgag ggcctgagcg    3540
gtaacgtgga gattccgaat gtcatcctct gggaaccact gaacacgtat ctctaccaga    3600
tcaaagtgga actggtgaac gacggactga ccatcgatgt ctatgaagag ccgttcggcg    3660
tgcggaccgt ggaagtcaac gacggcaagt tcctcatcaa caacaaaccg ttctacttca    3720
agggctttgg caaacatgag gacactccta tcaacggccg tggctttaac gaagcgagca    3780
atgtgatgga tttcaatatc ctcaaatgga tcggcgccaa cagcttccgg accgcacact    3840
atccgtactc tgaagagttg atgcgtcttg cggatcgcga gggtctggtc gtgatcgacg    3900
agactccggc agttggcgtg cacctcaact tcatggccac cacgggactc ggcgaaggca    3960
gcgagcgcgt cagtacctgg gagaagattc ggacgtttga gcaccatcaa gacgttctcc    4020
gtgaactggt gtctcgtgac aagaaccatc caagcgtcgt gatgtggagc atcgccaacg    4080
aggcggcgac tgaggaagag ggcgcgtacg agtacttcaa gccgttggtg gagctgacca    4140
aggaactcga cccacagaag cgtccggtca cgatcgtgct gtttgtgatg gctaccccgg    4200
agacggacaa agtcgccgaa ctgattgacg tcatcgcgct caatcgctat aacggatggt    4260
acttcgatgg cggtgatctc gaagcggcca aagtccatct ccgccaggaa tttcacgcgt    4320
ggaacaagcg ttgcccagga aagccgatca tgatcactga gtacgcgcca gacaccgttg    4380
cgggctttca cgacattgat ccagtgatgt tcaccgagga atatcaagtc gagtactacc    4440
aggcgaacca cgtcgtgttc gatgagtttg agaacttcgt gggtgagcaa gcgtggaact    4500
cgcggacttt cgcgacctct cagggcgtga tgcgcgtcca aggaaacaag aagggcgtgt    4560
tcactcgtga ccgcaagccg aagctcgccg cgcacgtctt tcgcgagcgc tggaccaaca    4620
ttccagattt cggctacaag aacgctagcc atcaccatca ccatcacgtg tgaaccaaca    4680
tactcgatcg gttcctatat atgctcgatg aaggtttacg tggtgccata tattgccgat    4740
tcagtgctcc tgttcgttcg tccttggtgc gatgttgttg cacgtgcggt atatgatctg    4800
tttagtttat tttatctact atgaggtgtg aaaaggctat tatgacctat gtgttttaga    4860
aaaatatgtt atgagctatg tggtgtggaa ataaagctc ttgtgagttt tgtgttgtgt    4920
tgtgaaaaaa gctataaact gtttctttgt aataaatatg aaacctgtcc ccttttttat    4980
ctcctttgaa acagctataa tacaaaatgc atctctattg caatgaataa tcctcttcaa    5040
agagagaggt gccctcagga atacaggtgg tgcatggctt tcgtcagctc atgccgtaag    5100
```

```
gtattgggtt aagtctcgca acgagcgtaa cccttgtgtt gatgtctagt ccagtgtagc    5160
tgacattgct aaaatgcatc aacttggtgc taaaaatagg agaacatata gcattataaa    5220
gactgcttac caaggggttt aatataatgt gtccaagaat aaaatttaca aacctcataa    5280
atgaccccgg ttatggtatt tgtcatggca attgcctgtt cgaggtatgc agattttctt    5340
atgcggccag ccttgagcgg tgaacagtac tgcgggttcg tcttcaaggg aagtttcata    5400
tttggagaca ataggttgga cagagacagc ctgtgctttg gaaccaggct cagcaagttg    5460
acttgtcgcc ttcacttgct caacttgggt gatgaggaca aggccgctat acatatagcc    5520
atgcttagag aatcacatgc agaccaagta gatcaacaag gggacctgaa tggagaagaa    5580
ggtctaaagc ttatacggtt tcagtcaccg gtggaagcct aaatcaagtt cgagtccacc    5640
tcggaatcta ggagcagtct gtagtaaaac ggatgcccag gaaacattct gattctgttt    5700
ttgatgatcc acatatggat gaaagataaa tttgataagc taactaatgg ctttagtttc    5760
acgtcaaaat tcatccgaag tcaacaggaa tcgtcaaaac aagttagcat ccagaatctg    5820
caagggtgct gcgtcactgt ttttggtccg ttgggttgtg tatcatcatt gagtccatta    5880
ggagaggcgt ccagggag tgacgaccct aacaccttat aatcagtaac cgccaccctc    5940
attaggattt gggttattct atttacaata gtttcactat cattggtttt taagacccca    6000
actttgtgag attaatcatt catttgcaaa tttagttgca ttttttgtt cttgcttgtg    6060 ttctttgatt tgcaggcaag gattagcctt cttggcgagg tcgaacgtgc agcgccggtc    6120
aataacctga gatgacgtgg tgctaaggtt gcatgg                               6156
```

<210> SEQ ID NO 23
<211> LENGTH: 6184
<212> TYPE: DNA
<213> ORGANISM: Artificial Sequence
<220> FEATURE:
<223> OTHER INFORMATION: SfiI-2_36 promoter::GUS-plus::2_36 terminator-
      SfiI cassette

<400> SEQUENCE: 23

```
gcggcccta aggcccaata tgcatcggca tcttgccgat gaggcggctg cggatctggc     60
acctgatggc gaacctccac gtgtctgttc gggacgtgat ctgtacgaa cattgtattg    120 atcacctgtc ctccaatctg cggaccacca aactgctgtc caccgattgg ctgtcctccg    180
aattgctgtc caaaattcat tggctggttg ggaatcccct gaccttggaa cccgggatag    240
acctgccctt gctggaaccc tgtagtctgg taactctgct ggggcgattg tggaaaggct    300
tgctgtccaa accatccact attagcgttc atcggcatag atgctgccga tgattggtaa    360
ttgggtaccg tcgttgaatt gacataccc gactgggccg cagacctctg ttgtatcagc    420
attgactttg ccgatgcgtt gggcatctgg aacattgaat cttgaggatt ccagtgtga    480 ggccttgcag tagtggttgt ggtataccga ggactctggt tcatcggcgc attgggaggt    540
gccgatgtca taggagtttt gcccctcatg tcagttatct gtgatgttcc cggtgtcacc    600
tctggaggca taccgtaacc ccaccagttg ggaggaagag tcaaccctga cattgccaat    660
gccaacatat ctgttgtcag tttatgctgc ccaactgaaa tctgtgggtt ggttgccatc    720
ggcatagata gtgcaccagt agtccccgat gtacttggag gacggcaga ttgtgcactt    780 gcattcgtca aggcagccga cggagccgtg acctctggtg ccgttggctg atgatgggag    840
gggcccacat actctggtgg gatttgtcct tccttgaaag tccttgccac ggcattgaaa    900
accgtattag acagtacacc agcttggtta atcaacgctc gattgatggc attgtcaacc    960
```

```
atatcttgaa gcttgccagg attggcgtca aaggtaacct gccgtggtgc cggcagcgca    1020
tctttctgaa ccacttcgcc gctcctgttt atgctgaaag acctcaggca ttgctgcttg    1080
aactcttcca tggcttgggc aatagcttgc ttctgctcat ccttgaggtt ggcctccgtc    1140
acggggatga cgttctcttg atcgaggtca gagatcgaca tgttgatctt gatcttgaat    1200
ctgtcccacc gggcgtgcca aagatgtgt tgatgcaaaa gctgatctgc aaacacaaag    1260
ggctaatacc cgatttcaac gttaaggcgt gccagccgat ttgaccttac tatcggcaaa    1320
ggtgataact cgaatacttt ggtcccgaca acagcgatgc cccagatgc cacggccaag     1380 aggtattcac gcggaacttg agaacacgcc gagcttaagt cgacgaattc ctaagaactc    1440
gtaataaaaa ggaaaaagta tgacaaagtc gtcgaaatag tagatgctgg aatatgagta    1500
aaaacttgtg tttgattgat tgatagatca ttacaaggcc ctagggtcta tatttatacc    1560
ctgctcaaag agttacaacc agacacaatt agaattcgaa ttccaaatta cacggaatcc    1620
gtatacaaaa cgatgtaaat aattaaggaa ataacaaaac tatcccccgt gacaaactga    1680
aactcctcca cacaacgacc ggcagcttcc ggactccctc ttttgcatca tcggcagacc    1740
ctttgccata gtcatcggca gactttctta tctagccatc ggcacaatca catcactgtc    1800
tgtagactta gtcacgttca gcttctcctt catcggcaac tatcctcatc ggcaacccac    1860
cctgtagaca gcatactgcc acctatcct gccatcctag acacatgccc aaaaacggtg     1920
tcaacagtac ttggtgtctt ggtgattgaa tactatcagc gaatcaggtc aacgatctac    1980
tagcaattaa caatatatca tttcttaatc ttttgctagt tccgtttcaa ttagaaaact    2040
atctctacca ctcatctgca tgctattgtt cttaattaat tacttgatat atatggagca    2100
tatctctacc actctcatct gcacatgcta ataatata tagtgatttg cacgattcac      2160
aatcaataat ttgcatgata atatactgga acacgtgaac cagaggcact tacggccgcg    2220
tgtttattac ttaatttgcc atataagata ctatatgatt cctttcacag attggcagag    2280
atatgacatg tgttatctta ttctgtgatt aactatgtat atatgcccgg gatttaattt    2340
ttgcctgatc cgaaacaaat ggggaaccac tactgcgtcg cattcctcgc ataagatata    2400
ttctacagta ataaacaacg acgtctgccc acagaacgaa atcgctcgaa gcctcaaaac    2460
gacggacgga gtaaccaatg catgcccaag ctctctatat atattcgctt gaacgtctct    2520
ccaatcacat cacacggcga gctagctagg aaacaaacac acatcaacat acagcaaaca    2580
ttagacaaga atcaaacacg ttcgcaggaa aagaatagaa gctagggagg aggaaatggt    2640
agatctgagg gtaaatttct agttttctc cttcattttc ttggttagga cccttttctc     2700
tttttatttt tttgagcttt gatctttctt taaactgatc tattttttaa ttgattggtt    2760
atggtgtaaa tattacatag ctttaactga taatctgatt actttatttc gtgtgtctat    2820
gatgatgatg atagttacag aaccgacgaa ctagtctgta cccgatcaac accgagaccc    2880
gtggcgtctt cgacctcaat ggcgtctgga acttcaagct ggactacggg aaaggactgg    2940
aagagaagtg gtacgaaagc aagctgaccg acactattag tatggccgtc caagcagtt    3000 acaatgacat tggcgtgacc aaggaaatcc gcaaccatat cggatatgtc tggtacgaac    3060
gtgagttcac ggtgccggcc tatctgaagg atcagcgtat cgtgctccgc ttcggctctg    3120
caactcacaa agcaattgtc tatgtcaatg gtgagctggt cgtggagcac aagggcggat    3180
tcctgccatt cgaagcggaa atcaacaact cgctgcgtga tggcatgaat cgcgtcaccg    3240
tcgccgtgga caacatcctc gacgatagca ccctcccggt ggggctgtac agcgagcgcc    3300
acgaagaggg cctcggaaaa gtcattcgta acaagccgaa cttcgacttc ttcaactatg    3360
```

-continued

```
caggcctgca ccgtccggtg aaaatctaca cgacccccgtt tacgtacgtc gaggacatct    3420
cggttgtgac cgacttcaat ggcccaaccg ggactgtgac ctatacggtg gactttcaag    3480
gcaaagccga gaccgtgaaa gtgtcggtcg tggatgagga aggcaaagtg gtcgcaagca    3540
ccgagggcct gagcggtaac gtggagattc cgaatgtcat cctctgggaa ccactgaaca    3600
cgtatctcta ccagatcaaa gtggaactgg tgaacgacgg actgaccatc gatgtctatg    3660
aagagccgtt cggcgtgcgg accgtggaag tcaacgacgg caagttcctc atcaacaaca    3720
aaccgttcta cttcaagggc tttggcaaac atgaggacac tcctatcaac ggccgtggct    3780
ttaacgaagc gagcaatgtg atggatttca atatcctcaa atggatcggc ccaacagct    3840 tccggaccgc acactatccg tactctgaag agttgatgcg tcttgcggat cgcgagggtc    3900
tggtcgtgat cgacgagact ccggcagttg gcgtgcacct caacttcatg ccaccacgg    3960 gactcggcga aggcagcgag cgcgtcagta cctgggagaa gattcggacg tttgagcacc    4020
atcaagacgt tctccgtgaa ctggtgtctc gtgacaagaa ccatccaagc gtcgtgatgt    4080
ggagcatcgc caacgaggcg gcgactgagg aagagggcgc gtacgagtac ttcaagccgt    4140
tggtggagct gaccaaggaa ctcgacccac agaagcgtcc ggtcacgatc gtgctgtttg    4200
tgatggctac cccggagacg gacaaagtcg ccgaactgat tgacgtcatc gcgctcaatc    4260
gctataacgg atggtacttc gatggcggtg atctcgaagc ggccaaagtc catctccgcc    4320
aggaatttca cgcgtggaac aagcgttgcc caggaaagcc gatcatgatc actgagtacg    4380
gcgcagacac cgttgcgggc tttcacgaca ttgatccagt gatgttcacc gaggaatatc    4440
aagtcgagta ctaccaggcg aaccacgtcg tgttcgatga gtttgagaac ttcgtgggtg    4500
agcaagcgtg gaacttcgcg gacttcgcga cctctcaggg cgtgatgcgc gtccaaggaa    4560
acaagaaggg cgtgttcact cgtgaccgca agccgaagct cgccgcgcac gtctttcgcg    4620
agcgctggac caacattcca gatttcggct acaagaacgc tagccatcac catcaccatc    4680
acgtgtgaac caacatactc gatcggttcc tatatatgct cgatgaaggt ttacgtggtg    4740
ccatatattg ccgattcagt gctcctgttc gttcgtcctt ggtgcgatgt tgttgcacgt    4800
gcggtatatg atctgtttag tttattttat ctactatgag gtgtgaaaag gctattatga    4860
cctatgtgtt ttagaaaaat atgttatgag ctatgtggtg tggaaaataa agctcttgtg    4920
agttttgtgt tgtgttgtga aaaagctat aaactgtttc tttgtaataa atatgaaacc    4980
tgtccccttt tttatctcct ttgaaacagc tataatacaa aatgcatctc tattgcaatg    5040
aataatcctc ttcaaagaga gaggtgccct caggaataca ggtggtgcat ggctttcgtc    5100
agctcatgcc gtaaggtatt gggttaagtc tcgcaacgag cgtaaccctt gtgttgatgt    5160
ctagtccagt gtagctgaca ttgctaaaat gcatcaactt ggtgctaaaa ataggagaac    5220
atatagcatt ataaagactg cttaccaagg ggtttaatat aatgtgtcca agaataaaat    5280
ttacaaacct cataaatgac cccgttatg gtatttgtca tggcaattgc ctgttcgagg    5340
tatgcagatt ttcttatgcg gccagccttg agcggtgaac agtactgcgg gttcgtcttc    5400
aagggaagtt tcatatttgg agacaatagg ttggacagag acagcctgtg ctttggaacc    5460
aggctcagca agttgacttg tcgccttcac ttgctcaact tgggtgatga ggacaaggcc    5520
gctatacata tagccatgct tagagaatca catgcagacc aagtagatca acaaggggac    5580
ctgaatggag aagaaggtct aaagcttata cggtttcagt caccggtgga agcctaaatc    5640
aagttcgagt ccacctcgga atctaggagc agtctgtagt aaaacggatg cccaggaaac    5700
```

| | |
|---|---:|
| attctgattc tgtttttgat gatccacata tggatgaaaa gataatttga taagctaact | 5760 |
| aatggcttta gtttcacgtc aaaattcatc cgaagtcaac aggaatcgtc aaaacaagtt | 5820 |
| agcatccaga atctgcaagg gtgctgcgtc actgttttg gtccgttggg ttgtgtatca | 5880 |
| tcattgagtc cattaggaga ggcgtccaga gggagtgacg accctaacac cttataatca | 5940 |
| gtaaccgcca ccctcattag gatttgggtt attctattta caatagtttc actatcattg | 6000 |
| gttttaaga ccccaacttt gtgagattaa tcattcattt gcaaatttag ttgcatttt | 6060 |
| ttgttcttgc ttgtgttctt tgatttgcag gcaaggatta gccttcttgg cgaggtcgaa | 6120 |
| cgtgcagcgc cggtcaataa cctgagatga cgtggtgcta aggttgcatg gccgccatgg | 6180 |
| ccgc | 6184 |

<210> SEQ ID NO 24
<211> LENGTH: 2633
<212> TYPE: DNA
<213> ORGANISM: Artificial Sequence
<220> FEATURE:
<223> OTHER INFORMATION: SfiI-2_36 promoter

<400> SEQUENCE: 24

| | |
|---|---:|
| ggcccttaag gcccaatatg catcggcatc ttgccgatga ggcggctgcg gatctggcac | 60 |
| ctgatggcga acctccacgt gtctgttcgg gacgtgatct gtacggaaca ttgtattgat | 120 |
| cacctgtcct ccaatctgcg gaccaccaaa ctgctgtcca ccgattggct gtcctccgaa | 180 |
| ttgctgtcca aaattcattg gctggttggg aatcccctga ccttggaacc cgggatagac | 240 |
| ctgcccttgc tggaaccctg tagtctggta actctgctgg ggcgattgtg gaaaggcttg | 300 |
| ctgtccaaac catccactat tagcgttcat cggcatagat gctgccgatg attggtaatt | 360 |
| gggtaccgtc gttgaattga catacccga ctgggccgca gacctctgtt gtatcagcat | 420 |
| tgactttgcc gatgcgttgg gcatctggaa cattgaatct tgaggatttc cagtgtgagg | 480 |
| ccttgcagta gtggttgtgg tataccgagg actctggttc atcggcgcat gggaggtgc | 540 |
| cgatgtcata ggagttttgc ccctcatgtc agttatctgt gatgttcccg gtgtcacctc | 600 |
| tggaggcata ccgtaacccc accagttggg aggaagagtc aaccctgaca ttgccaatgc | 660 |
| caacatatct gttgtcagtt tatgctgccc aactgaaatc tgtgggttgg ttgccatcgg | 720 |
| catagatagt gcaccagtag tccccgatgt acttggaggg acggcagatt gtgcacttgc | 780 |
| attcgtcaag gcagccgacg gagccgtgac ctctggtgcc gttggctgat gatgggaggg | 840 |
| gcccacatac tctggtggga tttgtccttc cttgaaagtc cttgccacgg cattgaaaac | 900 |
| cgtattagac agtacaccag cttggttaat caacgctcga ttgatggcat tgtcaaccat | 960 |
| atcttgaagc ttgccaggat tggcgtcaaa ggtaacctgc cgtggtgccg gcagcgcatc | 1020 |
| tttctgaacc acttcgccgc tcctgtttat gctgaaagac ctcaggcatt gctgcttgaa | 1080 |
| ctcttccatg gcttgggcaa tagcttgctt ctgctcatcc ttgaggttgg cctccgtcac | 1140 |
| ggggatgacg ttctcttgat cgaggtcaga gatcgacatg ttgatcttga tcttgaatct | 1200 |
| gtcccaccgg gcgtgccaaa agatgtgttg atgcaaaagc tgatctgcaa acacaaaggg | 1260 |
| ctaatacccg atttcaacgt taaggcgtgc cagccgattt gaccttacta tcggcaaagg | 1320 |
| tgataactcg aatactttgg tcccgacaac agcgatgcgc ccagatgcca cggccaagag | 1380 |
| gtattcacgc ggaacttgag aacacgccga gcttaagtcg acgaattcct aagaactcgt | 1440 |
| aataaaaagg aaaaagtatg acaaagtcgt cgaaatagta gatgctggaa tatgagtaaa | 1500 |
| aacttgtgtt tgattgattg atagatcatt acaaggccct aggtctata tttatacct | 1560 |

```
gctcaaagag ttacaaccag acacaattag aattcgaatt ccaaattaca cggaatccgt    1620
atacaaaacg atgtaaataa ttaaggaaat aacaaaacta tccccgtga caaactgaaa     1680 ctcctccaca caacgaccgg cagcttccgg actccctctt ttgcatcatc ggcagaccct    1740
ttgccatagt catcggcaga ctttcttatc tagccatcgg cacaatcaca tcactgtctg    1800
tagacttagt cacgttcagc ttctccttca tcggcaacta tcctcatcgg caacccaccc    1860
tgtagacagc atactgccac cttatcctgc catcctagac acatgcccaa aaacggtgtc    1920
aacagtactt ggtgtcttgg tgattgaata ctatcagcga atcaggtcaa cgatctacta    1980
gcaattaaca atatatcatt tcttaatctt ttgctagttc cgtttcaatt agaaaactat    2040
ctctaccact catctgcatg ctattgttct taattaatta cttgatatat atggagcata    2100
tctctaccac tctcatctgc acatgctaat ataatatata gtgatttgca cgattcacaa    2160
tcaataattt gcatgataat atactggaac acgtgaacca gaggcactta cggccgcgtg    2220
tttattactt aatttgccat ataagatact atatgattcc tttcacagat tggcagagat    2280
atgacatgtg ttatcttatt ctgtgattaa ctatgtatat atgcccggga tttaattttt    2340
gcctgatccg aaacaaatgg ggaaccacta ctgcgtcgca ttcctcgcat aagatatatt    2400
ctacagtaat aaacaacgac gtctgcccac agaacgaaat cgctcgaagc ctcaaaacga    2460
cggacggagt aaccaatgca tgcccaagct ctctatatat attcgcttga acgtctctcc    2520
aatcacatca cacggcgagc tagctaggaa acaaacacac atcaacatac agcaaacatt    2580
agacaagaat caaacacgtt cgcaggaaaa gaatagaagc tagggaggag gaa           2633
```

<210> SEQ ID NO 25
<211> LENGTH: 1494
<212> TYPE: DNA
<213> ORGANISM: Artificial Sequence
<220> FEATURE:
<223> OTHER INFORMATION: 2_36 terminator- SfiI

<400> SEQUENCE: 25

```
accaacatac tcgatcggtt cctatatatg ctcgatgaag gtttacgtgg tgccatatat     60
tgccgattca gtgctcctgt tcgttcgtcc ttggtgcgat gttgttgcac gtgcggtata    120
tgatctgttt agtttatttt atctactatg aggtgtgaaa aggctattat gacctatgtg    180
ttttagaaaa atatgttatg agctatgtgg tgtggaaaat aaagctcttg tgagttttgt    240
gttgtgttgt gaaaaaagct ataaactgtt tctttgtaat aaatatgaaa cctgtcccct    300
tttttatctc ctttgaaaca gctataatac aaaatgcatc tctattgcaa tgaataatcc    360
tcttcaaaga gagaggtgcc ctcaggaata caggtggtgc atggctttcg tcagctcatg    420
ccgtaaggta ttgggttaag tctcgcaacg agcgtaaccc ttgtgttgat gtctagtcca    480
gtgtagctga cattgctaaa atgcatcaac ttggtgctaa aaataggaga acatatagca    540
ttataaagac tgcttaccaa ggggtttaat ataatgtgtc caagaataaa atttacaaac    600
ctcataaatg accccggtta tggtatttgt catggcaatt gcctgttcga ggtatgcaga    660
ttttcttatg cggccagcct tgagcggtga acagtactgc gggttcgtct tcaagggaag    720
tttcatattt ggagacaata ggttggacag agacagcctg tgctttggaa ccaggctcag    780
caagttgact tgtcgccttc acttgctcaa cttgggtgat gaggacaagg ccgctataca    840
tatagccatg cttagagaat cacatgcaga ccaagtagat caacaagggg acctgaatgg    900
agaagaaggt ctaaagctta tacggtttca gtcaccggtg gaagcctaaa tcaagttcga    960
```

```
gtccacctcg gaatctagga gcagtctgta gtaaaacgga tgcccaggaa acattctgat   1020
tctgtttttg atgatccaca tatggatgaa aagataattt gataagctaa ctaatggctt   1080
tagtttcacg tcaaaattca tccgaagtca acaggaatcg tcaaaacaag ttagcatcca   1140
gaatctgcaa gggtgctgcg tcactgtttt tggtccgttg ggttgtgtat catcattgag   1200
tccattagga gaggcgtcca gagggagtga cgaccctaac accttataat cagtaaccgc   1260
caccctcatt aggatttggg ttattctatt tacaatagtt tcactatcat tggtttttaa   1320
gaccccaact ttgtgagatt aatcattcat ttgcaaattt agttgcattt ttttgttctt   1380
gcttgtgttc tttgatttgc aggcaaggat tagccttctt ggcgaggtcg aacgtgcagc   1440
gccggtcaat aacctgagat gacgtggtgc taaggttgca tggccgccat ggcc          1494
```

<210> SEQ ID NO 26
<211> LENGTH: 25
<212> TYPE: DNA
<213> ORGANISM: Sorghum bicolor

<400> SEQUENCE: 26
ttgccgattc agtgctcctg ttcgt                                           25

<210> SEQ ID NO 27
<211> LENGTH: 24
<212> TYPE: DNA
<213> ORGANISM: Sorghum bicolor

<400> SEQUENCE: 27
cgtgcaacaa catcgcacca agga                                            24

<210> SEQ ID NO 28
<211> LENGTH: 20
<212> TYPE: DNA
<213> ORGANISM: Sorghum bicolor

<400> SEQUENCE: 28
atccagggct acaagaaggg                                                 20

<210> SEQ ID NO 29
<211> LENGTH: 20
<212> TYPE: DNA
<213> ORGANISM: Sorghum bicolor

<400> SEQUENCE: 29
cgacaggtga tgatggcgaa                                                 20

<210> SEQ ID NO 30
<211> LENGTH: 22
<212> TYPE: DNA
<213> ORGANISM: Sorghum bicolor

<400> SEQUENCE: 30
atactaccgg gagccacaca ag                                              22

<210> SEQ ID NO 31
<211> LENGTH: 20
<212> TYPE: DNA
<213> ORGANISM: Sorghum bicolor

<400> SEQUENCE: 31
ccaaggaggt gaagtggcag                                                 20

```
<210> SEQ ID NO 32
<211> LENGTH: 26
<212> TYPE: DNA
<213> ORGANISM: Sorghum bicolor

<400> SEQUENCE: 32
aatgatgcgt tgttatttga ttgctt                                  26

<210> SEQ ID NO 33
<211> LENGTH: 22
<212> TYPE: DNA
<213> ORGANISM: Sorghum bicolor

<400> SEQUENCE: 33
tggtgactgc tgtactatgt gg                                      22

<210> SEQ ID NO 34
<211> LENGTH: 22
<212> TYPE: DNA
<213> ORGANISM: Sorghum bicolor

<400> SEQUENCE: 34
ggctcgaaga cgatcagata cc                                      22

<210> SEQ ID NO 35
<211> LENGTH: 18
<212> TYPE: DNA
<213> ORGANISM: Sorghum bicolor

<400> SEQUENCE: 35
tcggcatcgt ttatggtt                                           18

<210> SEQ ID NO 36
<211> LENGTH: 23
<212> TYPE: DNA
<213> ORGANISM: Sorghum bicolor

<400> SEQUENCE: 36
gccggagcca cccgtcatgg agc                                     23

<210> SEQ ID NO 37
<211> LENGTH: 27
<212> TYPE: DNA
<213> ORGANISM: Sorghum bicolor

<400> SEQUENCE: 37
ggctggcggt tgtggtggtg aacaagc                                 27

<210> SEQ ID NO 38
<211> LENGTH: 23
<212> TYPE: DNA
<213> ORGANISM: Sorghum bicolor

<400> SEQUENCE: 38
tgacttgcat cattgctggg agg                                     23

<210> SEQ ID NO 39
<211> LENGTH: 22
<212> TYPE: DNA
<213> ORGANISM: Sorghum bicolor

<400> SEQUENCE: 39
aagaggacga cgtcggcggc gt                                      22
```

<210> SEQ ID NO 40
<211> LENGTH: 23
<212> TYPE: DNA
<213> ORGANISM: Sorghum bicolor

<400> SEQUENCE: 40
cctctacctt tcatcaagct tcc                                             23

<210> SEQ ID NO 41
<211> LENGTH: 23
<212> TYPE: DNA
<213> ORGANISM: Sorghum bicolor

<400> SEQUENCE: 41
gcccgatgaa gtatatgtag acg                                             23

<210> SEQ ID NO 42
<211> LENGTH: 26
<212> TYPE: DNA
<213> ORGANISM: Sorghum bicolor

<400> SEQUENCE: 42
tagcagagga acttactgtc acaacg                                          26

<210> SEQ ID NO 43
<211> LENGTH: 22
<212> TYPE: DNA
<213> ORGANISM: Sorghum bicolor

<400> SEQUENCE: 43
aagttgcaac tcatctccaa ct                                              22

<210> SEQ ID NO 44
<211> LENGTH: 23
<212> TYPE: DNA
<213> ORGANISM: Sorghum bicolor

<400> SEQUENCE: 44
acagtctgat ctgaccttcc tga                                             23

<210> SEQ ID NO 45
<211> LENGTH: 23
<212> TYPE: DNA
<213> ORGANISM: Sorghum bicolor

<400> SEQUENCE: 45
catttcctcc tccctagctt cta                                             23

<210> SEQ ID NO 46
<211> LENGTH: 26
<212> TYPE: DNA
<213> ORGANISM: Sorghum bicolor

<400> SEQUENCE: 46
tgaaccaaca tactcgatcg gttcct                                          26

<210> SEQ ID NO 47
<211> LENGTH: 24
<212> TYPE: DNA
<213> ORGANISM: Sorghum bicolor

<400> SEQUENCE: 47
ccatgcaacc ttagcaccac gtca                                            24

<210> SEQ ID NO 48
<211> LENGTH: 20
<212> TYPE: DNA
<213> ORGANISM: Sorghum bicolor

<400> SEQUENCE: 48
gtatggcgaa tgcaaaccac                                            20

<210> SEQ ID NO 49
<211> LENGTH: 22
<212> TYPE: DNA
<213> ORGANISM: Sorghum bicolor

<400> SEQUENCE: 49
tattgctcga tcacaccagc tc                                         22

<210> SEQ ID NO 50
<211> LENGTH: 24
<212> TYPE: DNA
<213> ORGANISM: Sorghum bicolor

<400> SEQUENCE: 50
gatctcagcc tcatcctcaa ctac                                       24

<210> SEQ ID NO 51
<211> LENGTH: 22
<212> TYPE: DNA
<213> ORGANISM: Sorghum bicolor

<400> SEQUENCE: 51
ctggctgata ttgggctatg tg                                         22

<210> SEQ ID NO 52
<211> LENGTH: 30
<212> TYPE: DNA
<213> ORGANISM: Artificial Sequence
<220> FEATURE:
<223> OTHER INFORMATION: 2_32_pFH primer

<400> SEQUENCE: 52
cgcaagctta gctagatcgg atggttaaga                                 30

<210> SEQ ID NO 53
<211> LENGTH: 39
<212> TYPE: DNA
<213> ORGANISM: Artificial Sequence
<220> FEATURE:
<223> OTHER INFORMATION: 2_32_pgR primer

<400> SEQUENCE: 53
ttaccctcag atctaccatg gctggcggtt gtggtggtg                       39

<210> SEQ ID NO 54
<211> LENGTH: 39
<212> TYPE: DNA
<213> ORGANISM: Artificial Sequence
<220> FEATURE:
<223> OTHER INFORMATION: 2_32_pgF primer

<400> SEQUENCE: 54
caccaccaca accgccagcc atggtagatc tgagggtaa                       39

<210> SEQ ID NO 55

<210> SEQ ID NO 55
<211> LENGTH: 39
<212> TYPE: DNA
<213> ORGANISM: Artificial Sequence
<220> FEATURE:
<223> OTHER INFORMATION: 2_32_gtR primer

<400> SEQUENCE: 55
cctcccagca atgatgcaag tcacacgtga tggtgatgg         39

<210> SEQ ID NO 56
<211> LENGTH: 39
<212> TYPE: DNA
<213> ORGANISM: Artificial Sequence
<220> FEATURE:
<223> OTHER INFORMATION: 2_32_gtF primer

<400> SEQUENCE: 56
ccatcaccat cacgtgtgac ttgcatcatt gctgggagg         39

<210> SEQ ID NO 57
<211> LENGTH: 38
<212> TYPE: DNA
<213> ORGANISM: Artificial Sequence
<220> FEATURE:
<223> OTHER INFORMATION: 2_32_tRE primer

<400> SEQUENCE: 57
ccgaattctc gagattttat tctcgcaggt agaggcag         38

<210> SEQ ID NO 58
<211> LENGTH: 34
<212> TYPE: DNA
<213> ORGANISM: Artificial Sequence
<220> FEATURE:
<223> OTHER INFORMATION: 2_35_pFA primer

<400> SEQUENCE: 58 gcggcccta aggcctctgg gtactgctat tgag              34

<210> SEQ ID NO 59
<211> LENGTH: 45
<212> TYPE: DNA
<213> ORGANISM: Artificial Sequence
<220> FEATURE:
<223> OTHER INFORMATION: 2_35_pgR primer

<400> SEQUENCE: 59
gaaatttacc ctcagatcta ccatcgacga cgacgcacga cgtac    45

<210> SEQ ID NO 60
<211> LENGTH: 45
<212> TYPE: DNA
<213> ORGANISM: Artificial Sequence
<220> FEATURE:
<223> OTHER INFORMATION: 2_35_pgF primer

<400> SEQUENCE: 60
gtacgtcgtg cgtcgtcgtc gatggtagat ctgagggtaa atttc    45

<210> SEQ ID NO 61
<211> LENGTH: 45
<212> TYPE: DNA
<213> ORGANISM: Artificial Sequence
<220> FEATURE:
<223> OTHER INFORMATION: 2_35_gtR primer

<400> SEQUENCE: 61
cgttgtgaca gtaagttcct ctgctatcac acgtgatggt gatgg        45

<210> SEQ ID NO 62
<211> LENGTH: 45
<212> TYPE: DNA
<213> ORGANISM: Artificial Sequence
<220> FEATURE:
<223> OTHER INFORMATION: 2_35_gtF primer

<400> SEQUENCE: 62
ccatcaccat cacgtgtgat agcagaggaa cttactgtca caacg        45

<210> SEQ ID NO 63
<211> LENGTH: 38
<212> TYPE: DNA
<213> ORGANISM: Artificial Sequence
<220> FEATURE:
<223> OTHER INFORMATION: 2_35_tRB primer

<400> SEQUENCE: 63
gcggccatgg cggccaagtt gcaactcatc tccaactc        38

<210> SEQ ID NO 64
<211> LENGTH: 35
<212> TYPE: DNA
<213> ORGANISM: Artificial Sequence
<220> FEATURE:
<223> OTHER INFORMATION: 2_36_pFA primer

<400> SEQUENCE: 64
gcggccctta aggcccaata tgcatcggca tcttg        35

<210> SEQ ID NO 65
<211> LENGTH: 45
<212> TYPE: DNA
<213> ORGANISM: Artificial Sequence
<220> FEATURE:
<223> OTHER INFORMATION: 2_36_pgR primer

<400> SEQUENCE: 65
tttaccctca gatctaccat ttcctcctcc ctagcttcta ttctt        45

<210> SEQ ID NO 66
<211> LENGTH: 45
<212> TYPE: DNA
<213> ORGANISM: Artificial Sequence
<220> FEATURE:
<223> OTHER INFORMATION: 2_36_pgF primer

<400> SEQUENCE: 66
aagaatagaa gctagggagg aggaaatggt agatctgagg gtaaa        45

<210> SEQ ID NO 67
<211> LENGTH: 45
<212> TYPE: DNA
<213> ORGANISM: Artificial Sequence
<220> FEATURE:
<223> OTHER INFORMATION: 2_36_gtR primer

<400> SEQUENCE: 67
aggaaccgat cgagtatgtt ggttcacacg tgatggtgat ggtga        45

<210> SEQ ID NO 68
<211> LENGTH: 45
<212> TYPE: DNA

<213> ORGANISM: Artificial Sequence
<220> FEATURE:
<223> OTHER INFORMATION: 2_36_gtF primer

<400> SEQUENCE: 68
tcaccatcac catcacgtgt gaaccaacat actcgatcgg ttcct        45

<210> SEQ ID NO 69
<211> LENGTH: 37
<212> TYPE: DNA
<213> ORGANISM: Artificial Sequence
<220> FEATURE:
<223> OTHER INFORMATION: 2_36_tRB primer

<400> SEQUENCE: 69
gcggccatgg cggccatgca accttagcac cacgtca            37

<210> SEQ ID NO 70
<211> LENGTH: 38
<212> TYPE: DNA
<213> ORGANISM: Artificial Sequence
<220> FEATURE:
<223> OTHER INFORMATION: 2_23_pFA primer

<400> SEQUENCE: 70 gcggcccttta aggccacact agaatcactc tcccactc            38

<210> SEQ ID NO 71
<211> LENGTH: 45
<212> TYPE: DNA
<213> ORGANISM: Artificial Sequence
<220> FEATURE:
<223> OTHER INFORMATION: 2_23_pgR primer

<400> SEQUENCE: 71
aaatttaccc tcagatctac cattattgct cgatcacacc agctc        45

<210> SEQ ID NO 72
<211> LENGTH: 45
<212> TYPE: DNA
<213> ORGANISM: Artificial Sequence
<220> FEATURE:
<223> OTHER INFORMATION: 2_23_pgF primer

<400> SEQUENCE: 72
gagctggtgt gatcgagcaa taatggtaga tctgagggta aattt        45

<210> SEQ ID NO 73
<211> LENGTH: 45
<212> TYPE: DNA
<213> ORGANISM: Artificial Sequence
<220> FEATURE:
<223> OTHER INFORMATION: 2_23_gtR primer

<400> SEQUENCE: 73
gcgctgagat ccaggcgctc atcacacgtg atggtgatgg tgatg        45

<210> SEQ ID NO 74
<211> LENGTH: 45
<212> TYPE: DNA
<213> ORGANISM: Artificial Sequence
<220> FEATURE:
<223> OTHER INFORMATION: 2_23_gtF primer

<400> SEQUENCE: 74
catcaccatc accatcacgt gtgatgagcg cctggatctc agcgc        45

```
<210> SEQ ID NO 75
<211> LENGTH: 37
<212> TYPE: DNA
<213> ORGANISM: Artificial Sequence
<220> FEATURE:
<223> OTHER INFORMATION: 2_23_tRB primer

<400> SEQUENCE: 75
gcggccatgg cggccggggt gcgaatacca tagaaac                              37
```